US008186355B2

(12) United States Patent
van der Burg et al.

(10) Patent No.: US 8,186,355 B2
(45) Date of Patent: May 29, 2012

(54) GLOSSOPLASTY USING TISSUE ANCHOR GLOSSOPEXY WITH VOLUMETRIC TONGUE REDUCTION

(75) Inventors: Erik van der Burg, Los Gatos, CA (US); Beverly Tucker Woodson, Menominee Falls, WI (US); Michael Dineen, Portola Valley, CA (US); Mark Hirotsuka, San Jose, CA (US); Jasper Jackson, Newark, CA (US); Andrew Frazier, Sunnyvale, CA (US); Chad Roue, San Jose, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1090 days.

(21) Appl. No.: 11/598,220

(22) Filed: Nov. 9, 2006

(65) Prior Publication Data

US 2007/0144539 A1    Jun. 28, 2007

Related U.S. Application Data

(60) Provisional application No. 60/734,931, filed on Nov. 9, 2005, provisional application No. 60/735,565, filed on Nov. 10, 2005, provisional application No. 60/813,231, filed on Jun. 13, 2006.

(51) Int. Cl.
*A61F 5/56* (2006.01)
*A61B 17/04* (2006.01)

(52) U.S. Cl. .................................. 128/848; 606/300

(58) Field of Classification Search .............. 602/902; 600/37; 128/897, 898, 848, 831, 348, 887; 606/232, 60, 300–301, 310, 313, 77, 78, 606/151, 153–156, 193, 198, 75, 326, 327, 606/329, 330, 331; 623/1.36
See application file for complete search history.

(56) References Cited

U.S. PATENT DOCUMENTS

| 4,676,240 A | 6/1987 | Gardy |
| 5,460,524 A | 10/1995 | Anderson |
| 5,573,540 A | 11/1996 | Yoon |

(Continued)

FOREIGN PATENT DOCUMENTS

DE    1 242 322    6/1967

(Continued)

OTHER PUBLICATIONS

Cozzi, D.A., et al., *Recurrent Apparent Life-Threatening Event Relieved by Glossopexy*, Journal of Pediatric Surgery, vol. 31, No. 12, Dec. 1996, pp. 1715-1718.

(Continued)

*Primary Examiner* — Patricia Bianco
*Assistant Examiner* — Tarla Patel

(57) ABSTRACT

Methods and devices are disclosed for remodeling the tongue. One or more spaces or cavities are formed in the tongue using, for example, surgical or RF ablative techniques. The cavities can be closed or collapsed by inserting a tethered soft tissue anchor into the tongue and attaching the tethered portion of the soft tissue anchor to a bony structure such as the mandible or hyoid bone in order to exert a collapsing force on the one or more spaces or cavities. The insertion pathway of the tethered soft tissue anchor may pass adjacent to or even through one or more cavities. Also disclosed herein is a tongue remodeling system that includes means for creating a space in the tongue, and a tissue anchor configured to close the space. The tissue anchor may be tethered or expandable.

10 Claims, 46 Drawing Sheets

U.S. PATENT DOCUMENTS

| | | | |
|---|---|---|---|
| 5,893,856 | A | 4/1999 | Jacob et al. |
| 5,897,491 | A | 4/1999 | Kastenbauer et al. |
| 5,954,057 | A | 9/1999 | Li |
| 5,988,171 | A | 11/1999 | Sohn et al. |
| 6,042,534 | A | 3/2000 | Gellman et al. |
| 6,408,851 | B1 | 6/2002 | Karell |
| 7,090,672 | B2 | 8/2006 | Underwood |
| 7,213,599 | B2 * | 5/2007 | Conrad et al. ............... 128/897 |
| 2001/0050084 | A1 | 12/2001 | Knudson et al. |
| 2002/0087051 | A1 | 7/2002 | Levisman |
| 2002/0188297 | A1 * | 12/2002 | Dakin et al. ................ 606/72 |
| 2004/0045555 | A1 | 3/2004 | Nelson et al. |
| 2004/0078054 | A1 | 4/2004 | Biggs et al. |
| 2004/0122474 | A1 | 6/2004 | Gellman et al. |
| 2004/0138585 | A1 | 7/2004 | Dematteis et al. |
| 2005/0055027 | A1 * | 3/2005 | Yeung et al. ................ 606/75 |
| 2005/0092332 | A1 | 5/2005 | Conrad et al. |
| 2005/0092334 | A1 | 5/2005 | Conrad et al. |
| 2005/0234439 | A1 * | 10/2005 | Underwood ................ 606/32 |
| 2006/0235264 | A1 | 10/2006 | Vassallo |
| 2006/0235380 | A1 * | 10/2006 | Vassallo ..................... 606/45 |
| 2006/0266369 | A1 * | 11/2006 | Atkinson et al. ............ 128/848 |

FOREIGN PATENT DOCUMENTS

| | | |
|---|---|---|
| DE | 10 2005 000 702 A1 | 7/2006 |
| EP | 0 702 934 | 3/1996 |
| WO | WO 00/66050 | 11/2000 |
| WO | WO 2005/044158 A1 | 5/2005 |
| WO | WO 2005/122954 | 12/2005 |
| WO | WO 2006/072571 | 1/2006 |

OTHER PUBLICATIONS

J. Ramba, *Fixation of the Tongue Bellow Mandible in Pierre Robin Syndrome*, Department for Maxillofacial Surgery, Clinic of Paediatric Stomatology, 2nd Medical Faculty, Charles University, Prague, Czech Republic, ACTA Chirurgiae Plasticae 38, 2, 1996, pp. 54-56.

Hawkins, Donald B., M.D., et al., *Micrognathia and Glossoptosis in the Newborn*, Surgical Tacking of the Tongue in Small Jaw Syndromes, Clinical Pediatrics, vol. 13, No. 12, Dec. 1974, pp. 1066-1073.

Bath, A.P., et al., *Management of Upper Airway Obstruction in Pierre Robin Sequence*, The Journal of Laryngology and Otology, vol. 111, Dec. 1997, pp. 1155-1157.

Schatten, William E., M.D., et al., *Airway Management in Patients with Pierre Robin Syndrome*, Plastic and Reconstructive Surgery, vol. 38, No. 4, Oct. 1966, pp. 309-311.

Oegonomopoulos, Chris, T., M.D., *The Value of Glossopexy in Pierre-Robin Syndrome*, The New England Journal of Medicine, vol. 262, No. 25, Jun. 23, 1960, pp. 1267-1268.

Lapidot, Abraham, M.D., *A New Functional Approach to the Surgical Management of Pierre Robin Syndrome: Experimental and Clinical Report*, The Laryngoscope, A Medical Journal for Clinical and Research Contributions In: Otoloaryngology, Broncho-Esophagology, Communicative Disorders, Maxillofacial Surgery, Head and Neck Surgery, Facial Plastic and Reconstructive Surgery, vol. LXXXVI, No. 7, Jul. 1976, pp. 979-983.

Hadley, R.C., M.D., et al., *Utilization of the Kirschner Wire in Pierre Robin Syndrome*, Plastic and Reconstructive Surgery, vol. 31, No. 6, Jun. 1963, pp. 587-596.

Douglas, Beverly, M.D., *A Further Report on the Treatment of Micrognathia with Obstruction by a Plastic Procedure*, Plastic and Reconstructive Surgery, vol. 5, No. 2, Feb. 1950, pp. 113-122.

Douglas, B., M.D., *The Treatment of Micrognathia with Obstruction by a Plastic Operation*, Department of Surgery, School of Medicine, Vanderbilt University, pp. 420-431.

Douglas, Beverly, M.D., *The Treatment of Micrognathia Associated with Obstruction by a Plastic Operation, A Twenty Year Follow-Up Report*, Journal of the American Medical Women's Association, vol. 21, No. 12, Dec. 1966, pp. 1027-1033.

Lewis, Stephen R., M.D., et al., *Fascial Slings for Tongue Stabilization in the Pierre Robin Syndrome*, Plastic and Reconstructive Surgery, vol. 42, No. 3, Sep. 1968, pp. 237-241.

Lapidot, Abraham, M.D., et al., *Fastening the Base of the Tongue Forward to the Hyoid for Relief of Respiratory Distress in Pierre Robin Syndrome*, Plastic and Reconstructive Surgery, vol. 56, No. 1, Jul. 1975, pp. 89-91.

Rawashdeh, Ma'amon A., BDS, MScD, FDSRCS(En), *Surgical Strategies, Transmandibular K-Wire in the Management of Airway Obstruction in Pierre Robin Sequence*, The Journal of Craniofacial Surgery, vol. 15, No. 3, May 2004, pp. 450.

Argamaso, Ravelo, M.D., *Glossopexy for Upper Airway Obstruction in Robin Sequence*, Cleft Palate-Craniofacial Journal, vol. 29, No. 3, May 1992, pp. 232-238.

Omur, Mehmet, M.D., et al., *Tongue Base Suspension Combined with UPPP in Severe OSA Patients*, Otolaryngology-Head and Neck Surgery, vol. 133, No. 2, Aug. 2055, pp. 218-223.

DeRowe, Ari, M.D., et al., *Tongue-Base Suspension with a Soft Tissue-to-Bone Anchor for Obstructive Sleep Apnea: Preliminary Clinical Results of a New Minimally Invasive Technique*, Otolaryngology—Head and Neck Surgery, vol. 122, No. 1, Jan. 2000, pp.

Faye-Lund, H., et al., *Glossopexia—Evaluation of a new Surgical Method for Treating Obstructive Sleep Apnea Syndrome*, ACTA Otolaryngol (Stockh), 1992, Suppl. 492: pp. 46-49.

\* cited by examiner

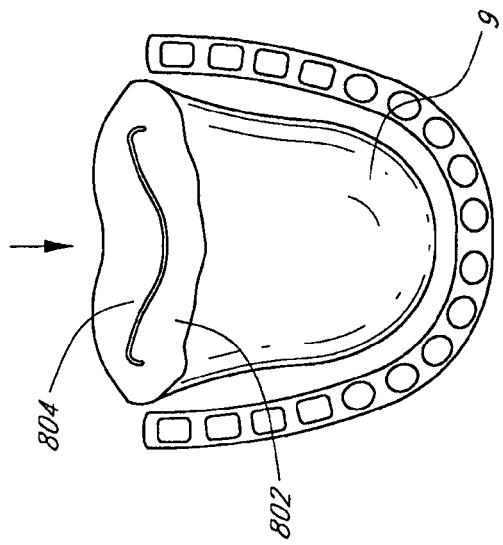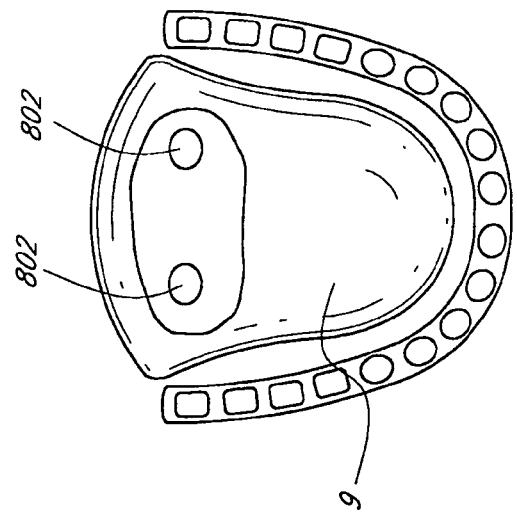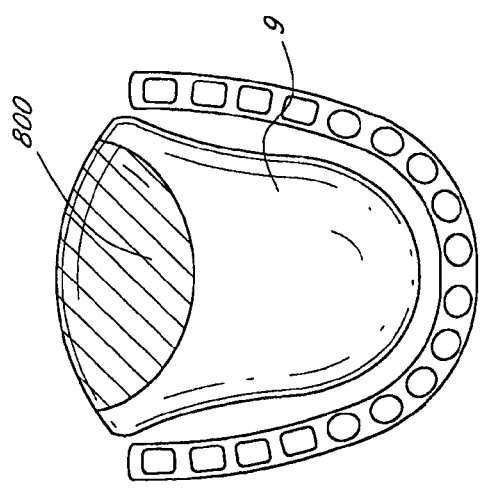

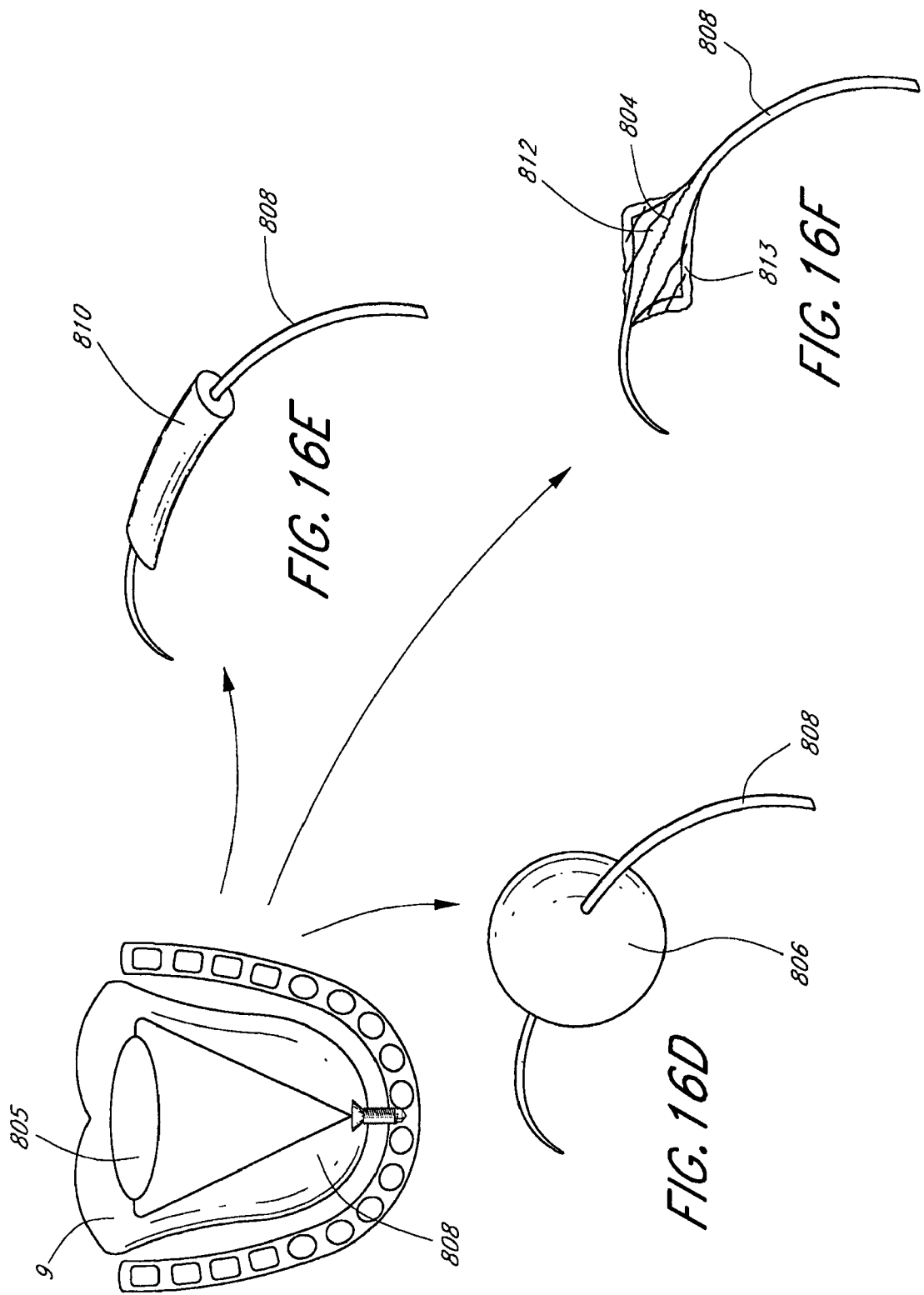

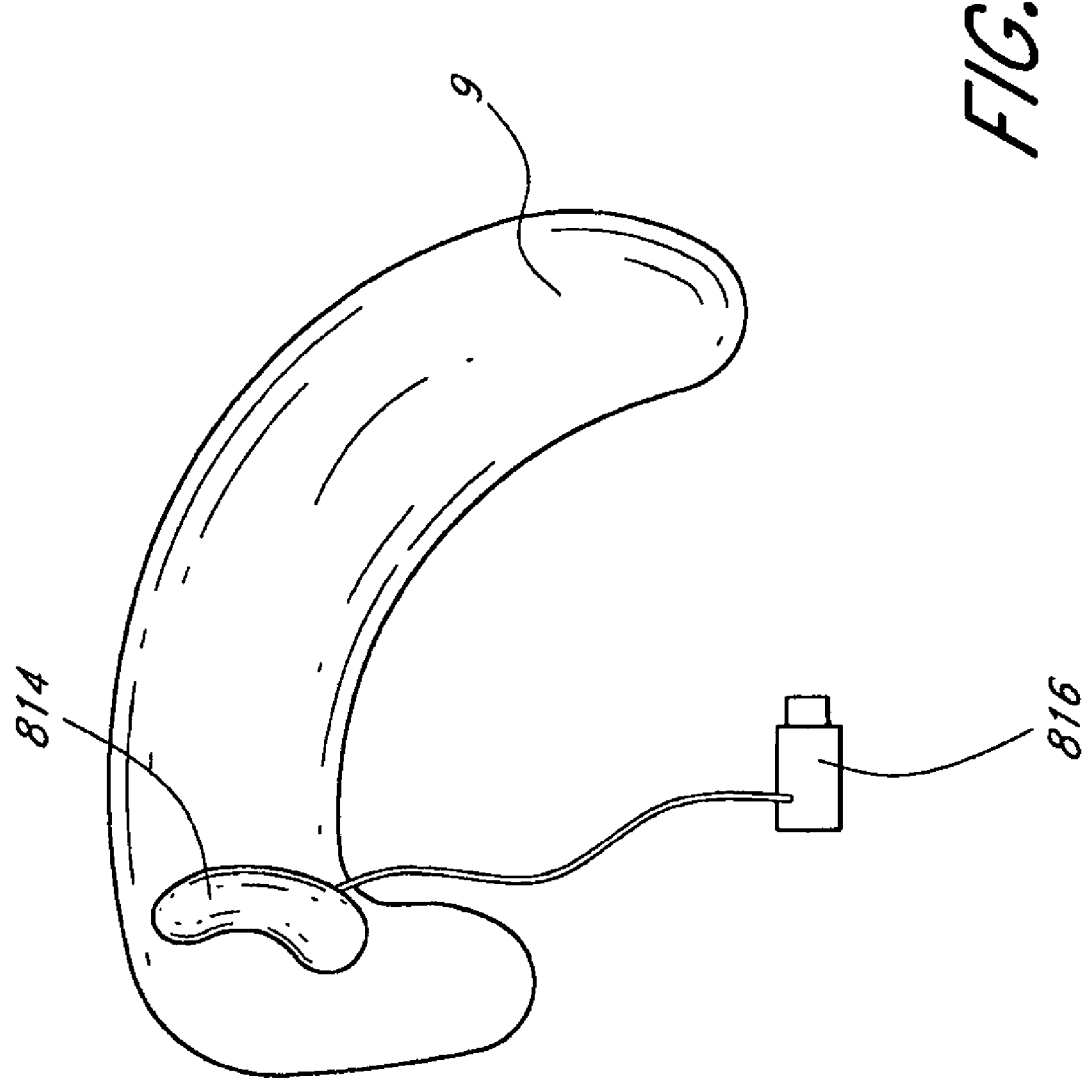

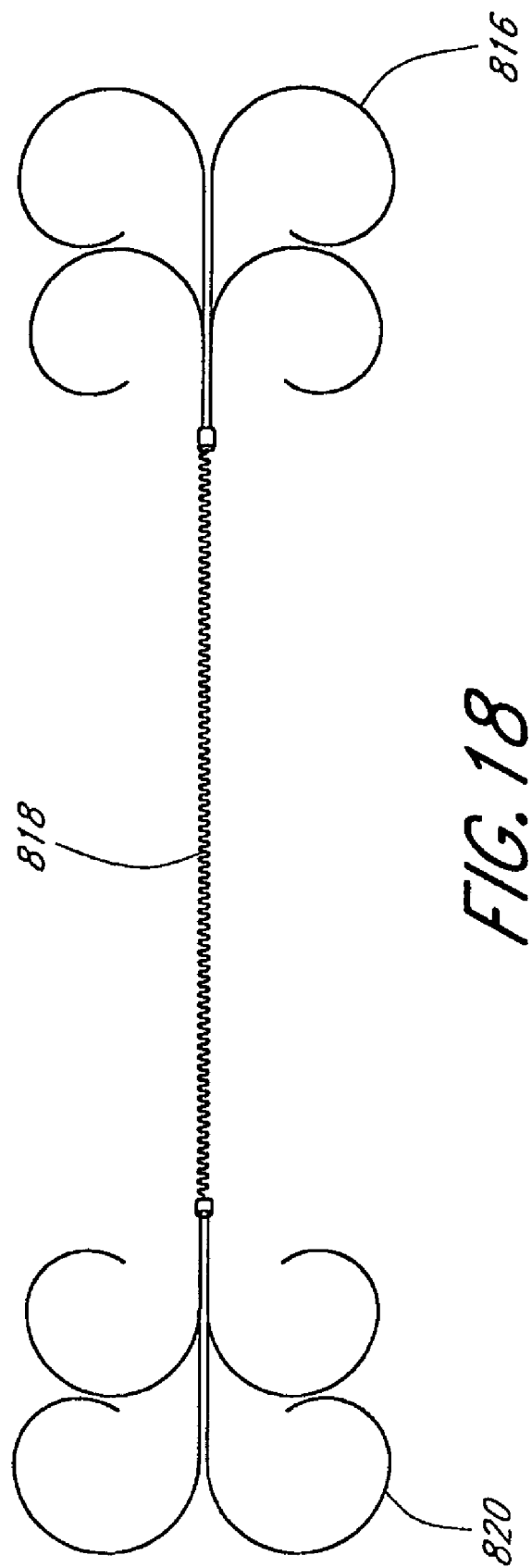

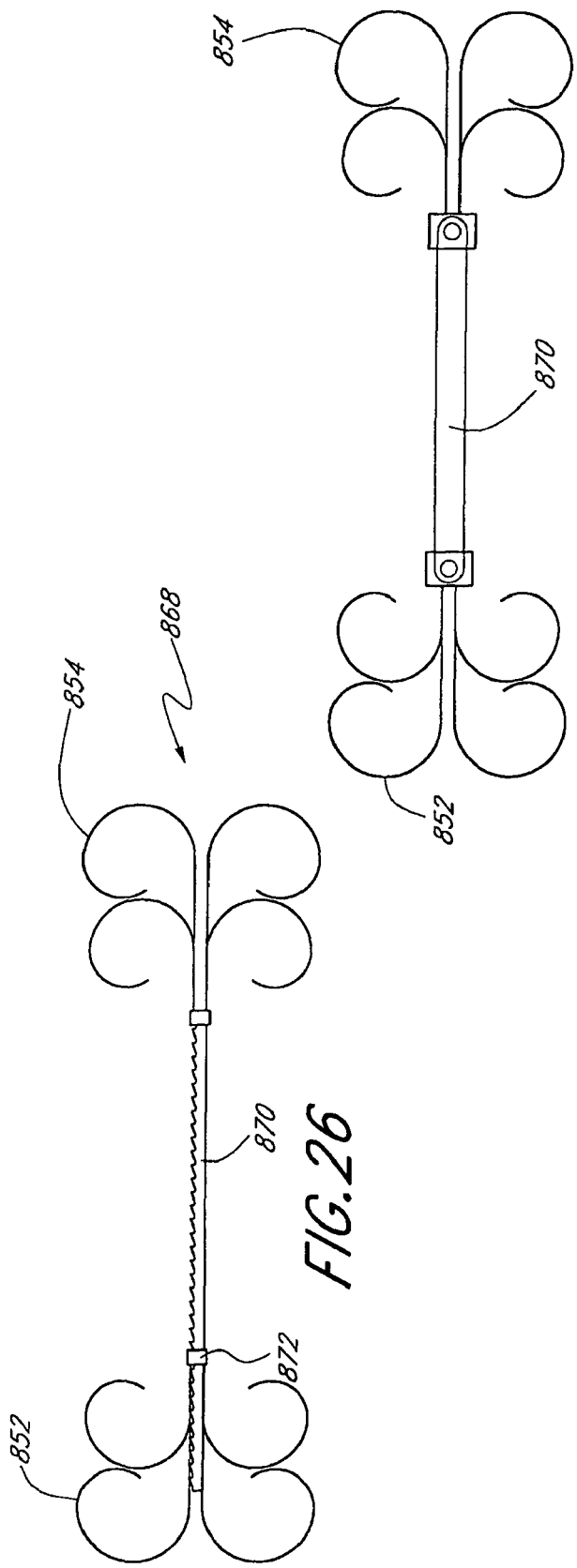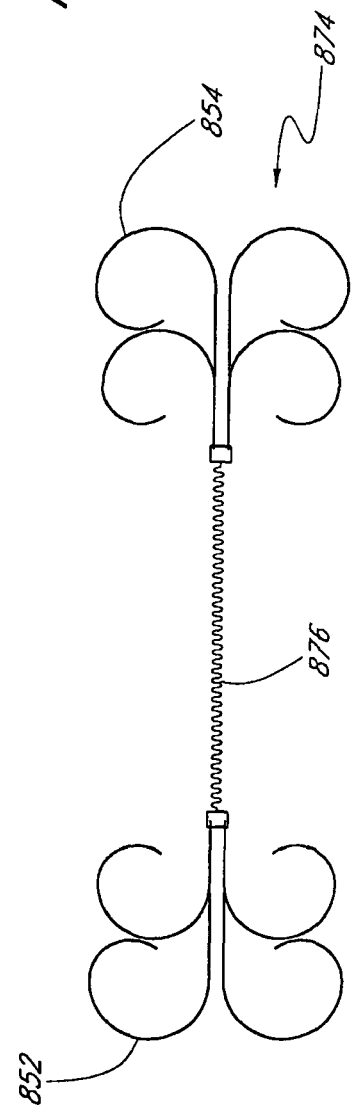

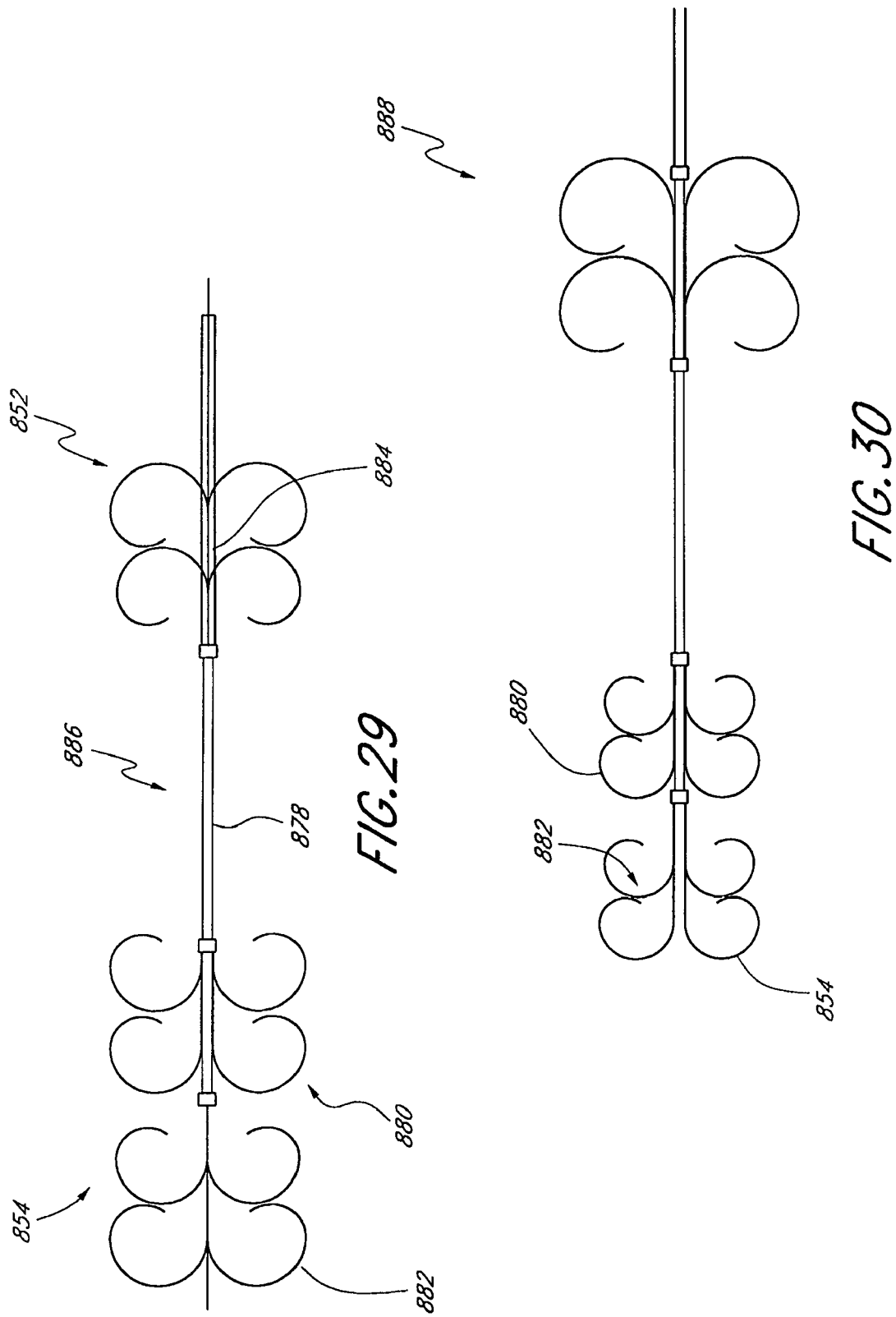

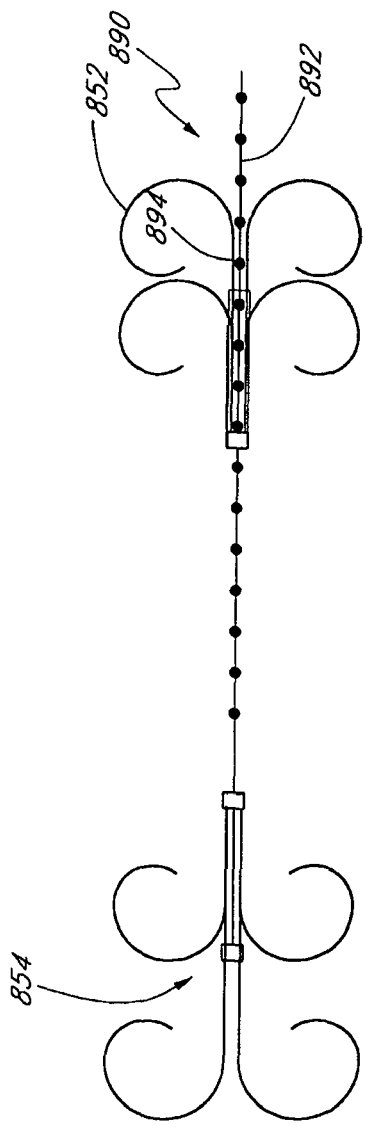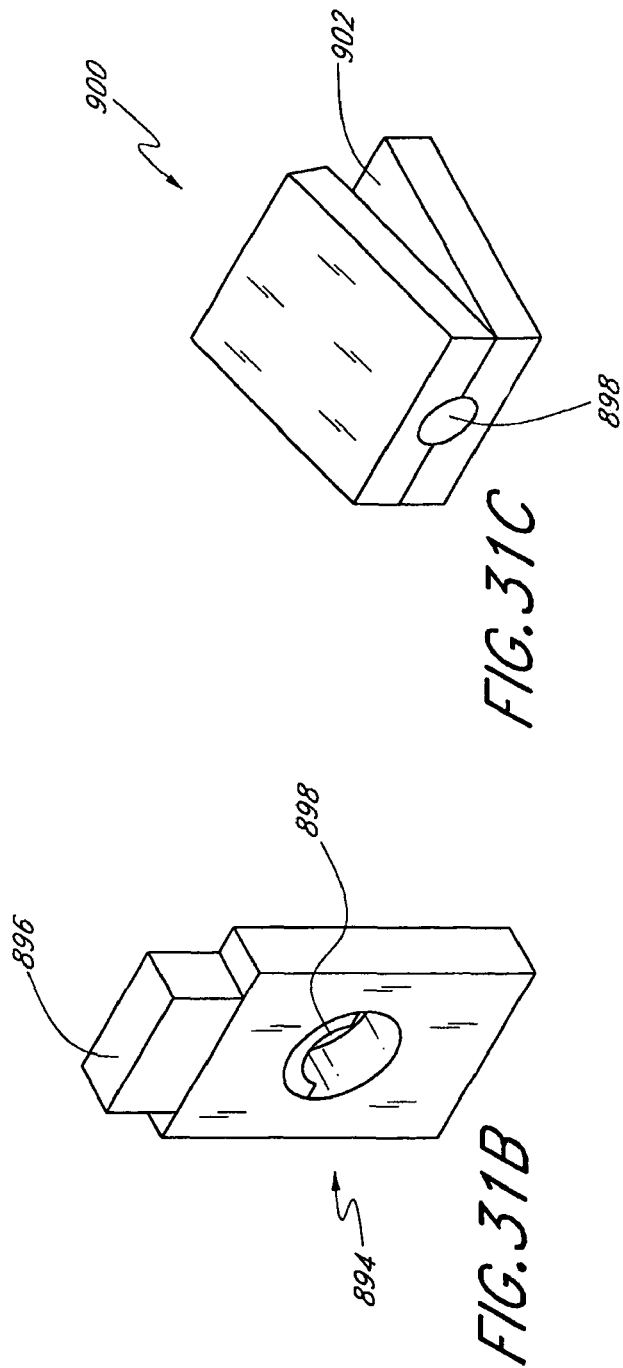

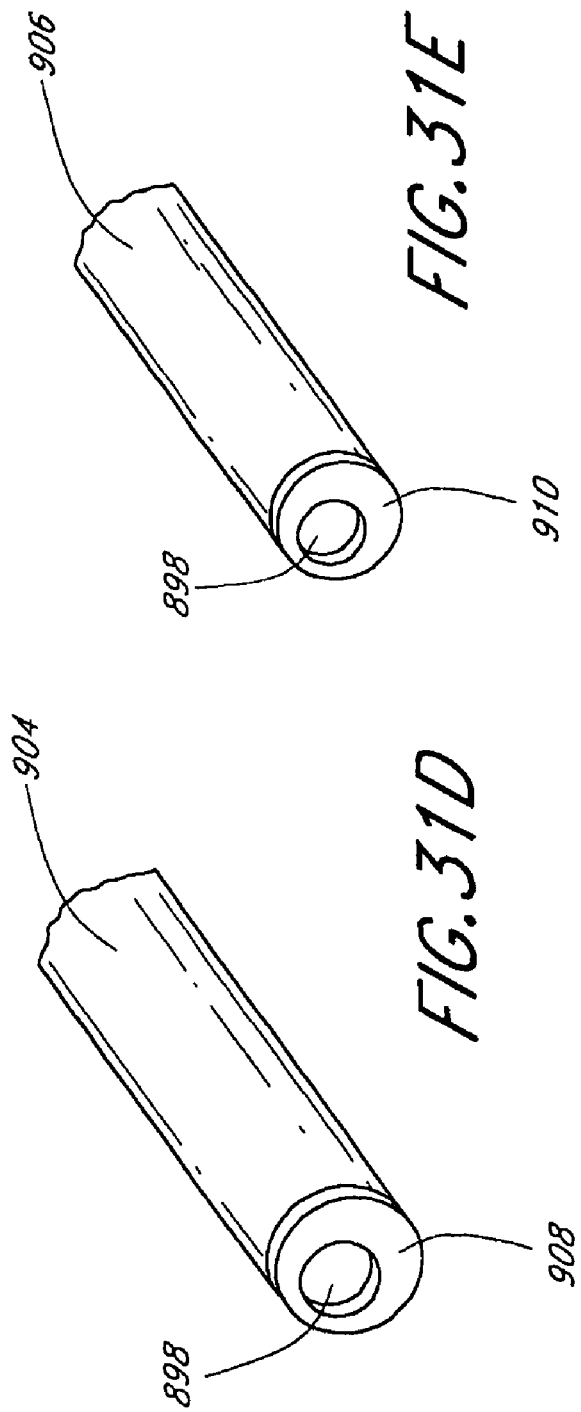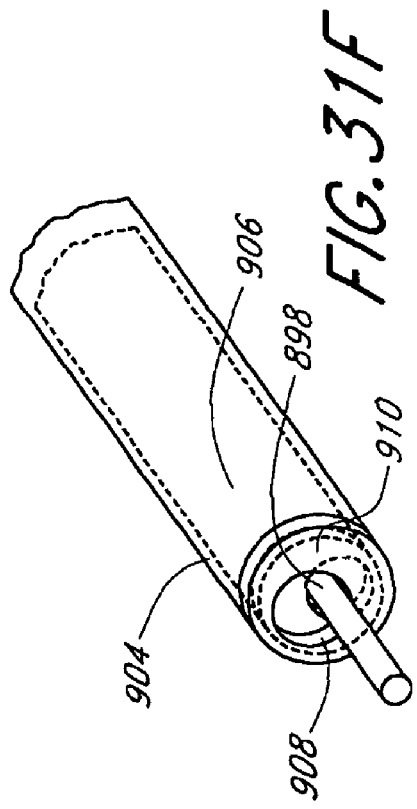

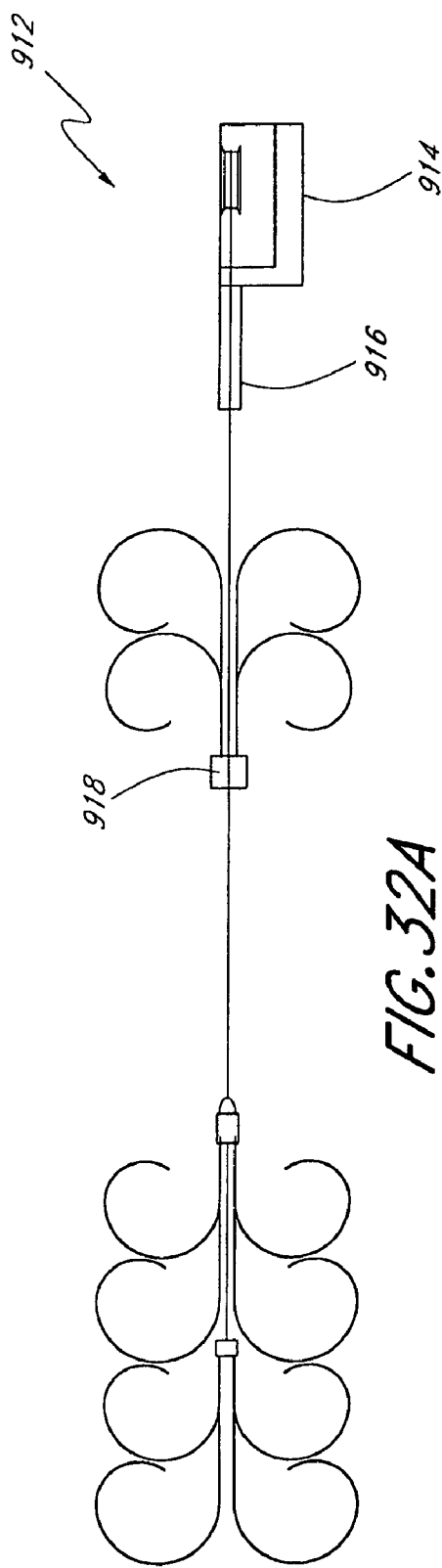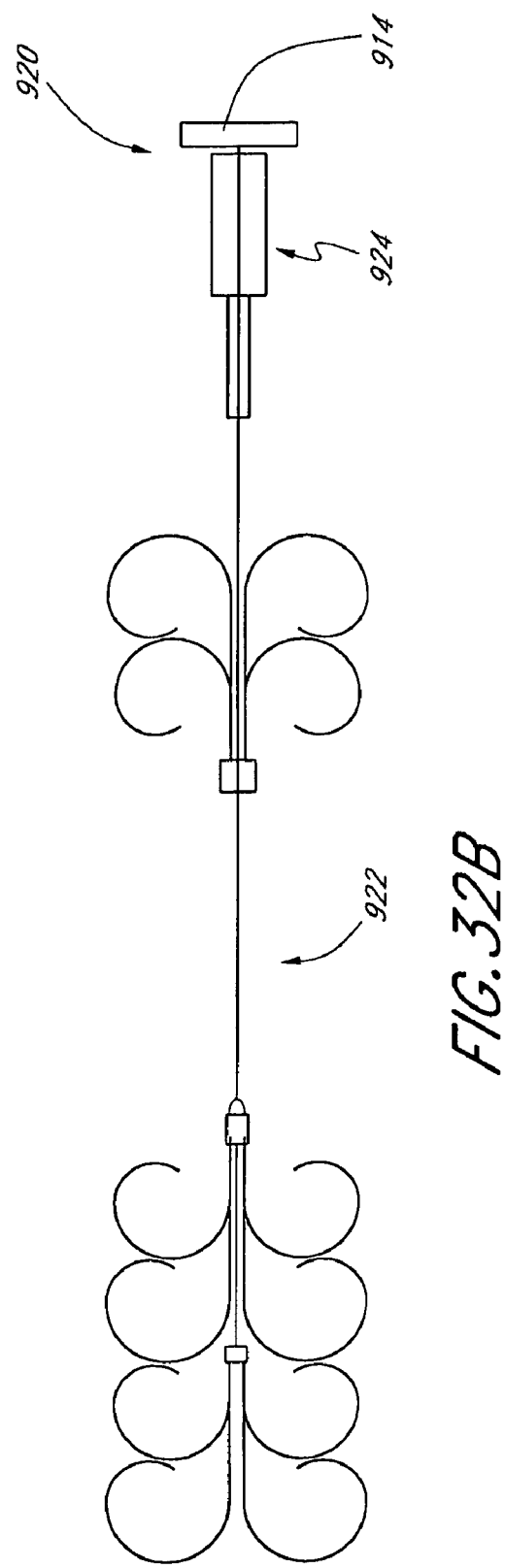
FIG.32A
FIG.32B

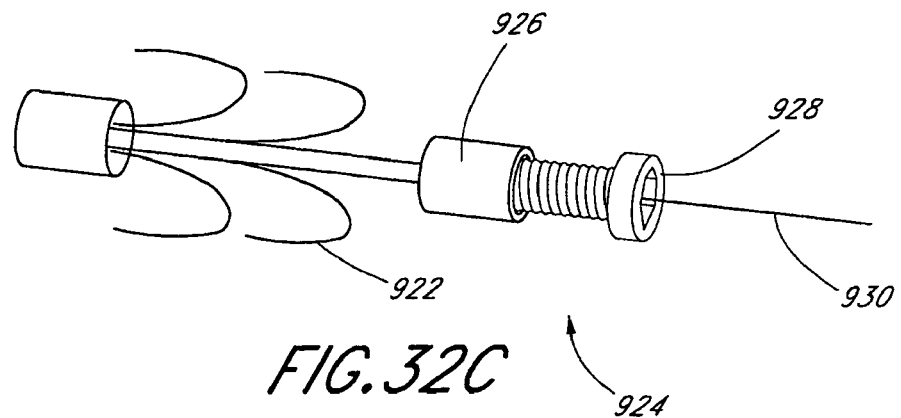
FIG.32C
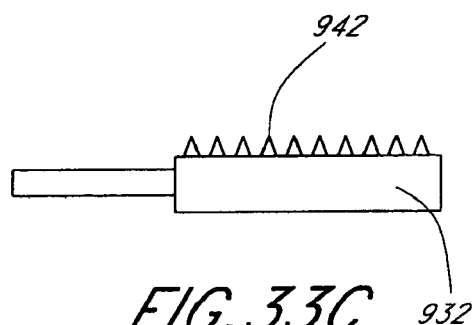
FIG.33C
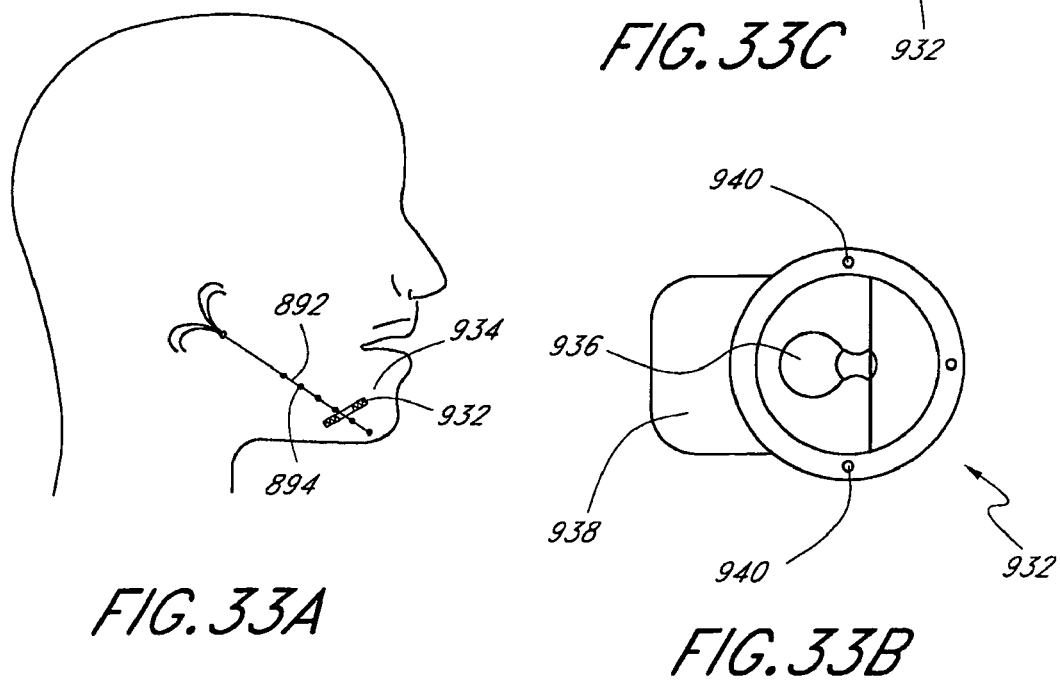
FIG.33A
FIG.33B

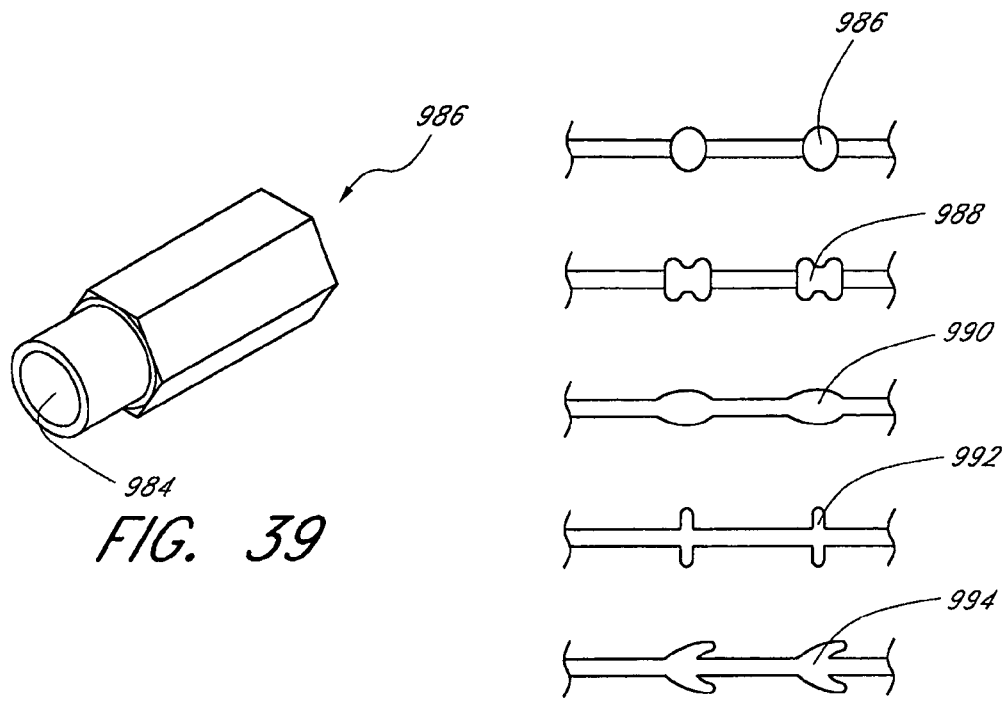
FIG. 39
FIG. 40A
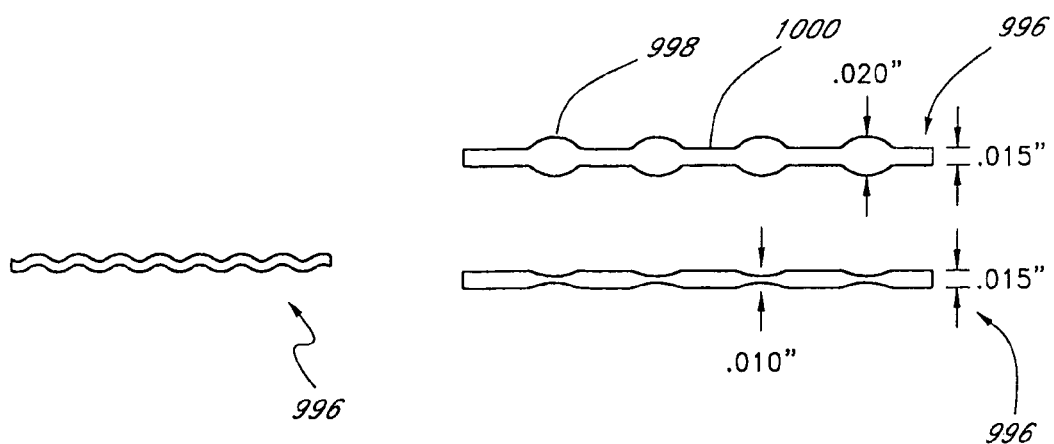
FIG. 40B

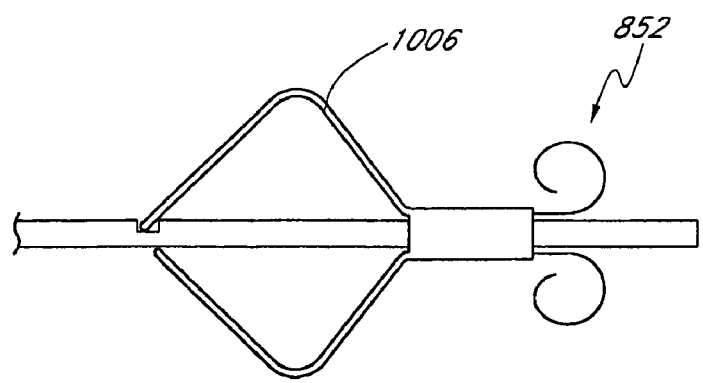
FIG. 41D
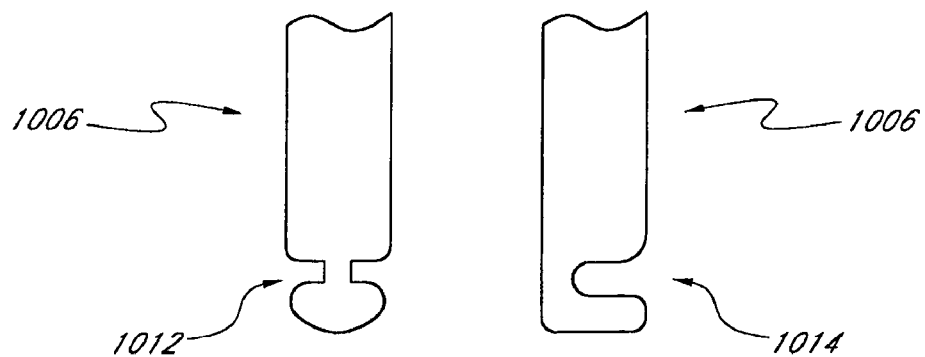
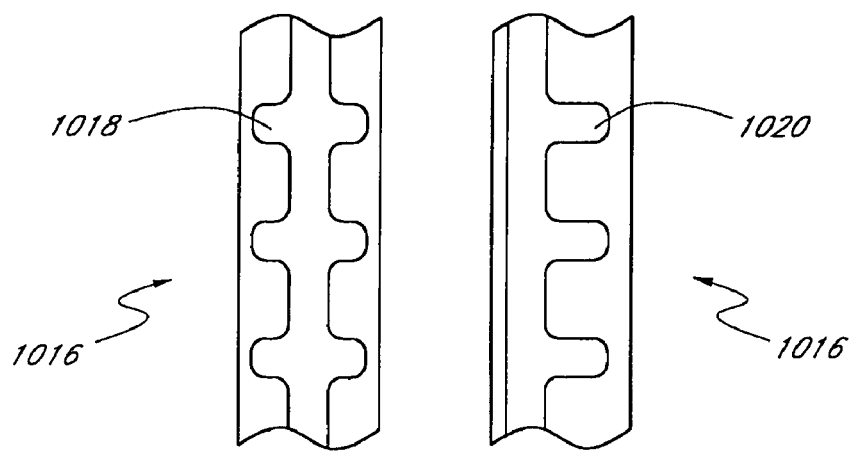
FIG. 41E

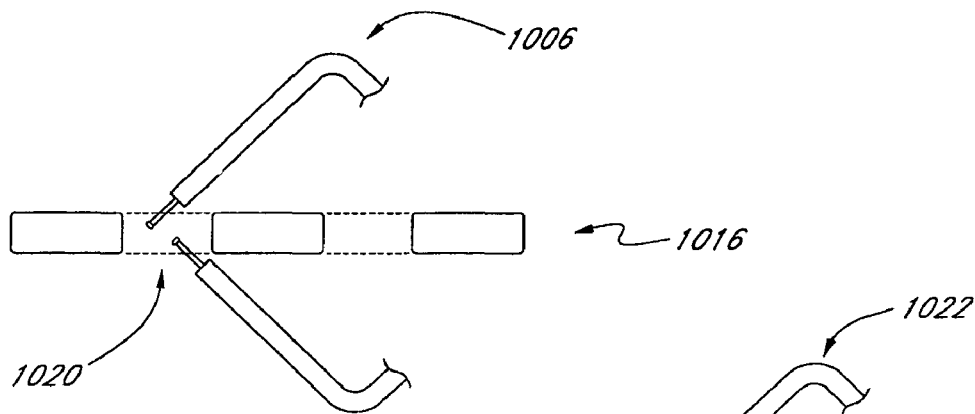
FIG.41F
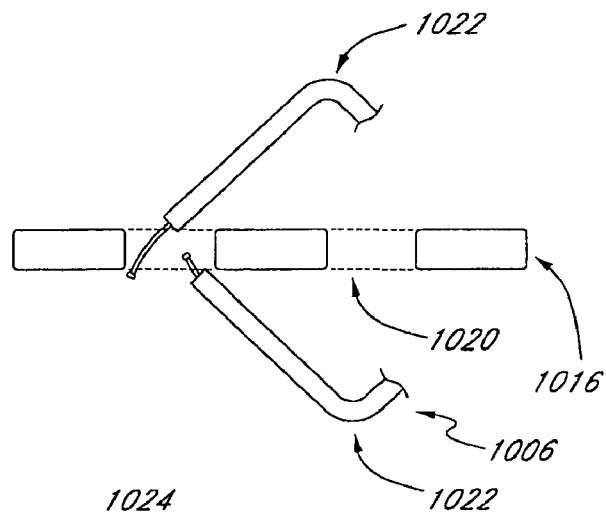
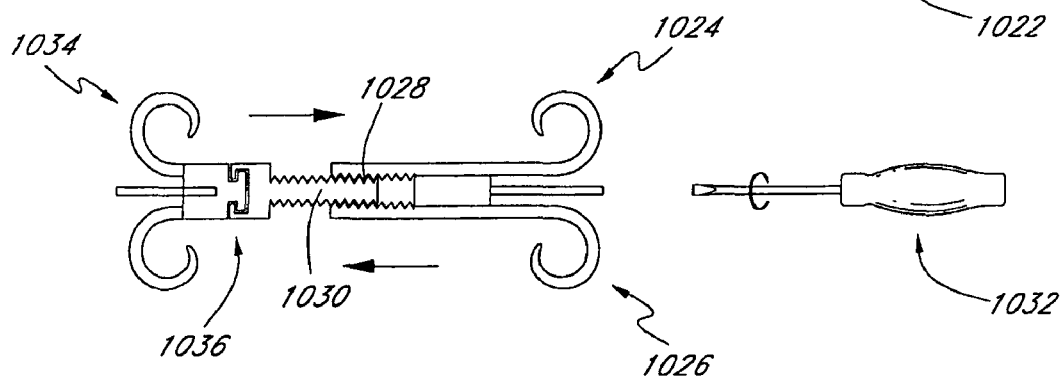
FIG.42
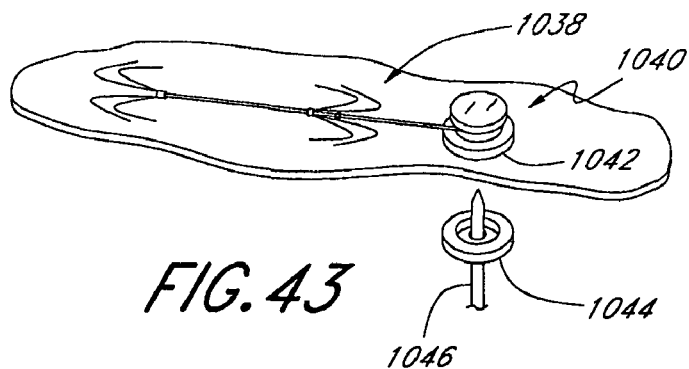
FIG.43

GLOSSOPLASTY USING TISSUE ANCHOR GLOSSOPEXY WITH VOLUMETRIC TONGUE REDUCTION

RELATED APPLICATIONS

This application claims the benefit under 35 U.S.C. §119 of U.S. Provisional Application Ser. No. 60/734,931, filed Nov. 9, 2005; Provisional Application Ser. No. 60/735,565 filed Nov. 10, 2005; and Provisional Application Ser. No. 60/813,231, filed Jun. 13, 2006. Also incorporated by reference in their entirety are the disclosures of each of the following: Provisional Application Ser. No. 60/650,867 filed Feb. 8, 2005, Provisional Application Ser. No. 60/726,028 filed Oct. 12, 2005, and Utility application Ser. No. 11/349,067 filed Feb. 7, 2006, currently pending, and published as U.S. Patent Publication No. 2006-0207608 A1 on Sep. 21, 2006.

BACKGROUND OF THE INVENTION

1. Field of the Invention

This invention relates generally to a system and method for treating upper airway obstruction, sleep disordered breathing, upper airway resistance syndrome and snoring by manipulating the structures of the oropharynx, including the tongue.

2. Description of the Related Art

Respiratory disorders during sleep are recognized as a common disorder with significant clinical consequences. During the various stages of sleep, the human body exhibits different patterns of brain and muscle activity. In particular, the REM sleep stage is associated with reduced or irregular ventilatory responses to chemical and mechanical stimuli and a significant degree of muscle inhibition. This muscle inhibition may lead to relaxation of certain muscle groups, including but not limited to muscles that maintain the patency of the upper airways, and create a risk of airway obstruction during sleep. Because muscle relaxation narrows the lumen of the airway, greater inspiratory effort may be required to overcome airway resistance. This increased inspiratory effort paradoxically increases the degree of airway resistance and obstruction through a Bernoulli effect on the flaccid pharyngeal walls during REM sleep.

Obstructive Sleep Apnea (OSA) is a sleep disorder that affects up to 2 to 4% of the population in the United States. OSA is characterized by an intermittent cessation of airflow in the presence of continued inspiratory effort. When these obstructive episodes occur, an affected person will transiently arouse, regain muscle tone and reopen the airway. Because these arousal episodes typically occur 10 to 60 times per night, sleep fragmentation occurs which produces excessive daytime sleepiness. Some patients with OSA experience over 100 transient arousal episodes per hour.

In addition to sleep disruption, OSA may also lead to cardiovascular and pulmonary disease. Apnea episodes of 60 seconds or more have been shown to decrease the partial pressure of oxygen in the lung alveoli by as much as 35 to 50 mm Hg. Some studies suggest that increased catecholamine release in the body due to the low oxygen saturation causes increases in systemic arterial blood pressure, which in turn causes left ventricular hypertrophy and eventually left heart failure. OSA is also associated with pulmonary hypertension, which can result in right heart failure.

Radiographic studies have shown that the site of obstruction in OSA is isolated generally to the supralaryngeal airway, but the particular site of obstruction varies with each person and multiple sites may be involved. A small percentage of patients with OSA have obstructions in the nasopharynx caused by deviated septums or enlarged turbinates. These obstructions may be treated with septoplasty or turbinate reduction procedures, respectively. More commonly, the oropharynx and the hypopharynx are implicated as sites of obstruction in OSA. Some studies have reported that the occlusion begins with the tongue falling back in an anterior-posterior direction (A-P) to contact with the soft palate and posterior pharyngeal wall, followed by further occlusion of the lower pharyngeal airway in the hypopharynx. This etiology is consistent with the physical findings associated with OSA, including a large base of tongue, a large soft palate, shallow palatal arch and a narrow mandibular arch. Other studies, however, have suggested that increased compliance of the lateral walls of the pharynx contributes to airway collapse. In the hypopharynx, radiographic studies have reported that hypopharyngeal collapse is frequently caused by lateral narrowing of the pharyngeal airway, rather than narrowing in the A-P direction.

OSA is generally diagnosed by performing overnight polysomnography in a sleep laboratory. Polysomnography typically includes electroencephalography to measure the stages of sleep, an electro-oculogram to measure rapid eye movements, monitoring of respiratory effort through intercostal electromyography or piezoelectric belts, electrocardiograms to monitor for arrhythmias, measurement of nasal and/or oral airflow and pulse oximetry to measure oxygen saturation of the blood.

Following the diagnosis of OSA, some patients are prescribed weight loss programs as part of their treatment plan, because of the association between obesity and OSA. Weight loss may reduce the frequency of apnea in some patients, but weight loss and other behavioral changes are difficult to achieve and maintain. Therefore, other modalities have also been used in the treatment of OSA, including pharmaceuticals, non-invasive devices and surgery.

Among the pharmaceutical treatments, respiratory stimulants and drugs that reduce REM sleep have been tried in OSA. Progesterone, theophylline and acetozolamide have been used as respiratory stimulants, but each drug is associated with significant side effects and their efficacy in OSA is not well studied. Protriptyline, a tricyclic antidepressant that reduces the amount of REM sleep, has been shown to decrease the frequency of apnea episodes in severe OSA, but is associated with anti-cholinergic side effects such as impotence, dry mouth, urinary retention and constipation.

Other modalities are directed at maintaining airway patency during sleep. Oral appliances aimed at changing the position of the soft palate, jaw or tongue are available, but patient discomfort and low compliance have limited their use. Continuous Positive Airway Pressure (CPAP) devices are often used as first-line treatments for OSA. These devices use a sealed mask which produce airflow at pressures of 5 to 15 cm of water and act to maintain positive air pressure within the pharyngeal airway and thereby maintain airway patency. Although CPAP is effective in treating OSA, patient compliance with these devices is low for several reasons. Sleeping with a sealed nasal mask is uncomfortable for patients. Smaller sealed nasal masks may be more comfortable to patients but are ineffective in patients who sleep with their mouths open, as the air pressure will enter the nasopharynx and then exit the oropharynx. CPAP also causes dry nasal passages and congestion.

Surgical treatments for OSA avoid issues with patient compliance and are useful for patients who fail conservative treatment. One surgery used for OSA is uvulopalatopharyngoplasty (UPPP). UPPP attempts to improve airway patency in the oropharynx by eliminating the structures that contact the tongue during sleep. This surgery involves removal of the uvula and a portion of the soft palate, along with the tonsils and portions of the tonsillar pillars. Although snoring is reduced in a majority of patients who undergo UPPP, the percentage of patients who experience reduced frequency of apnea episodes or improved oxygen saturation is substantially lower. Postoperatively, many patients that have undergone UPPP continue to exhibit oropharyngeal obstruction or concomitant hypopharyngeal obstruction. Nonresponders often have physical findings of a large base of tongue, an omega-shaped epiglottis and redundant aryepiglottic folds. UPPP is not a treatment directed at these structures. UPPP also exposes patients to the risks of general anesthesia and postoperative swelling of the airway that will require a tracheostomy. Excessive tissue removal may also cause velopharyngeal insufficiency where food and liquids enter into the nasopharynx during swallowing.

Laser-assisted uvulopalatopharyngoplasty (LAUP) is a similar procedure to UPPP that uses a CO2 laser to remove the uvula and portions of the soft palate, but the tonsils and the lateral pharyngeal walls are not removed.

For patients who fail UPPP or LAUP, other surgical treatments are available but these surgeries entail significantly higher risks of morbidity and mortality. In genioglossal advancement with hyoid myotomy (GAHM), an antero-inferior portion of the mandible, which includes the attachment point of the tongue musculature, is repositioned forward and in theory will pull the tongue forward and increase airway diameter. The muscles attached to the inferior hyoid bone are severed to allow the hyoid bone to move superiorly and anteriorly. Repositioning of the hyoid bone expands the retrolingual airspace by advancing the epiglottis and tongue base anteriorly. The hyoid bone is held in its new position by attaching to the mandible using fascia. Variants of this procedure attach the hyoid bone inferiorly to the thyroid cartilage.

A laser midline glossectomy (LMG) has also been tried in some patients who have failed UPPP and who exhibit hypopharyngeal collapse on radiographic studies. In this surgery, a laser is used to resect the midline portion of the base of the tongue. This involves significant morbidity and has shown only limited effectiveness.

In some patients with craniofacial abnormalities that include a receding mandible, mandibular or maxillomandibular advancement surgeries may be indicated for treatment of OSA. These patients are predisposed to OSA because the posterior mandible position produces posterior tongue displacement that causes airway obstruction. In a mandibular advancement procedure, the mandible is cut bilaterally posterior to the last molar and advanced forward approximately 10 to 14 mm. Bone grafts are used to bridge the bone gap and the newly positioned mandible is wire fixated to the maxilla until healing occurs. Mandibular advancement may be combined with a Le Fort I maxillary osteotomy procedure to correct associated dental or facial abnormalities. These procedures have a high morbidity and are indicated only in refractory cases of OSA.

Experimental procedures described in the clinical literature for OSA include the volumetric radiofrequency or electromagnetic tissue ablation and hyoidplasty, where the hyoid bone is cut into several segments and attached to a brace that widens the angle of the U-shaped hyoid bone. The latter procedure has been used in dogs to increase the pharyngeal airway lumen at the level of the hyoid bone. The canine hyoid bone, however, is unlike a human hyoid bone because the canine hyoid bone comprises nine separate and jointed bones, while the human hyoid bone comprises five bones that are typically fused together.

Notwithstanding the foregoing, there remains a need for improved methods and devices for treating obstructive sleep apnea.

SUMMARY OF THE INVENTION

Methods and devices are disclosed for remodeling the tongue. One or more spaces or cavities can be formed in the tongue using, for example, surgical, RF or electromagnetic ablative techniques. In one embodiment, the cavities are closed or collapsed by inserting a tethered soft tissue anchor into the tongue and attaching the tethered portion of the soft tissue anchor to a bony structure such as the mandible or hyoid bone in order to exert a collapsing force on the one or more spaces or cavities. The insertion pathway of the tethered soft tissue anchor may pass adjacent to or even through one or more cavities. The insertion pathway may be linear or non-linear.

In one embodiment, a method for treating a patient is provided, comprising inserting a tissue anchor into a tongue along an insertion pathway, the tongue comprising a space; and creating a force along the insertion pathway to deform the space. The insertion pathway may pass through the space or in proximity to the space. The space may be formed by tissue ablation or surgical tissue removal. The tissue ablation may be radiofrequency or electromagnetic tissue ablation. The tongue may further comprise a second space and the insertion pathway may pass through the second space. The space may be contiguous with the external surface of the tongue or may be within the tongue. The method may further comprise anchoring the tethered tissue anchor to a bony structure. The tissue anchor may be a tethered tissue anchor and/or an expandable tissue anchor. The tissue anchor may include a first tissue-engaging member and a second tissue-engaging member. The bony structure may be a mandible or a hyoid bone. The tethered tissue anchor may comprise a tether having a distal end and a proximal end, a distal tissue anchor and a proximal tissue anchor. The deformation of the space may be a collapse of the space or a reduced dimension of the space in one direction. The reduced dimension of the space in one direction may also involve an expanded dimension in another direction transverse to the one direction. Anchoring the tethered tissue anchor to a bony structure may be performed using a bone screw and/or may be performed using an adjustment assembly. The method may further comprise adjusting the force along the insertion pathway by manipulating the adjustment assembly and/or adjusting the deformation of the space by manipulating the adjustment assembly. The tissue anchor may comprise a distal tissue-engaging member and a proximal tissue-engaging member, and may further comprise a flexible member between the distal tissue-engaging member and the proximal tissue-engaging member.

In another embodiment, a method for treating a patient is provided, comprising inserting a tongue-engaging member into a tongue along an insertion pathway, the tongue comprising a space; anchoring the tongue-engaging member to a bony structure using an adjustment assembly; and creating a force along the insertion pathway to deform the space. The method may further comprise manipulating the adjustment assembly to alter the force along the insertion pathway. The tongue-engaging member may remain anchored to the bony structure when manipulating the adjustment assembly. The tongue-engaging member may comprise a tissue anchor or a suture loop.

In one embodiment, a method for treating a patient may be provided, comprising inserting a tethered tissue anchor along an insertion pathway into a space in the tongue; and creating a force along the insertion pathway to deform the space. The space may be pre-formed in the tongue.

In one embodiment, a method of treating a patient may be provided, comprising inserting an implant along an insertion pathway into a space in the tongue, and creating a force along the insertion pathway to deform the space. The implant may be a tethered tissue anchor. Creating a force along the insertion pathway to deform the space may be caused by transforming an implant from a first configuration to a second configuration. The implant may be a balloon. Transforming an implant from a first configuration to a second configuration may deform the space sufficiently to prevent the tongue from collapsing against a posterior pharyngeal wall during sleep.

In another embodiment, a method of treating a patient may be provided, comprising inserting a first tethered tissue anchor along an insertion pathway into a space in the tongue, inserting a second tissue anchor tethered to the first tissue anchor along an insertion pathway into the tongue to a position proximal to the first tethered tissue anchor, and creating a force along the insertion pathway to deform the space into a first shape. Adjusting the tension of the tether after implantation of the first and second tissue anchors may create a force to deform the space into a second shape.

In yet another embodiment, disclosed is a tongue remodeling system, comprising means for creating a space in a tongue, and a tissue anchor configured to close the space. The tissue anchor may be a tethered tissue anchor or an expandable tissue anchor. The tissue anchor may comprise a distal tissue-engaging member and a proximal tissue-engaging member. The tongue remodeling system may further comprise an adjustment assembly. The tongue remodeling system may also comprise means for adjusting at least one of the tension between the distal and proximal tissue-engaging members or the spacing between the distal and proximal tissue-engaging members. The adjustment assembly may be configured for attachment to a bony structure.

According to another aspect, disclosed is use of a device for closing a pre-formed space in the tongue, the device including a tissue anchor configured to close the space in the tongue. The tissue anchor may be a tethered tissue anchor, or an expandable tissue anchor in some embodiments. In some aspects, the tissue anchor may include a first tissue-engaging member and a second tissue-engaging member. In some aspects, the device further includes an adjustment assembly for anchoring the tissue anchor to a bony structure. The bony structure may be a mandible or a hyoid bone in some embodiments.

According to another aspect, also disclosed is use of a system for remodeling of a tongue, including means for creating a space in the tongue and a tissue anchor configured to close the space. The tissue anchor may be a tethered tissue anchor or an expandable tissue anchor. The tissue anchor may include a distal tissue-engaging member and a proximal tissue-engaging member. In some aspects, the system also includes an adjustment assembly. The adjustment assembly may be configured to adjust at least one of the tension or the spacing between the distal and proximal tissue-engaging members. In some aspects, the adjustment assembly is configured for attachment to a bony structure.

One of ordinary skill in the art will recognize that many of the embodiments disclosed herein are not limited to the purpose of deforming a space in the tongue. For example, in some embodiments, an anchor with a first and second tongue-engaging member and an adjustment mechanism to selectively adjust the distance and/or tension between the anchors can be used to manipulate the tongue and/or soft palate, as described in, for example, U.S. application Ser. No. 11/349,067 (published Sep. 21, 2006 as U.S. Patent Publication No. 2006/0201519 A1)(incorporated by reference in its entirety).

BRIEF DESCRIPTION OF THE DRAWINGS

The structure and method of using the invention will be better understood with the following detailed description of embodiments of the invention, along with the accompanying illustrations, in which:

FIGS. 16A-C illustrate another embodiment of a tongue-reshaping device.

FIGS. 16D-16F show top views of other various embodiments of tongue-reshaping devices that are surface area-increasing elements for connecting to tether loops at the tongue base.

FIG. 17 illustrates another embodiment of a tongue-reshaping device that comprises a chronically adjustable implant.

FIG. 18 illustrates another embodiment of a tongue-reshaping device comprising a plurality of tissue anchors connected therebetween by an elastic member.

FIGS. 26-27 illustrate embodiments of a double-ended grappling hook anchoring device comprising various adjustment elements.

FIG. 28 illustrates another embodiment of a tongue-reshaping device comprising a plurality of tissue anchors connected therebetween by an elastic member.

FIGS. 29-30 depict embodiments of an adjustment mechanism with a plurality of tissue anchors connected therebetween by a tether.

FIGS. 31A-F illustrate various embodiments and components of adjustment mechanisms that may be used in conjunction with a tongue remodeling system that is not secured to a bony structure.

FIGS. 32A-B illustrate an embodiment of an adjustment mechanism that comprises a spool.

FIG. 32C illustrates an embodiment of an adjustment mechanism with a threaded screw locking mechanism.

FIGS. 33A-C show embodiments of adjustment mechanisms that may be engaged within tissue.

FIG. 39 illustrates an element of an adjustment mechanism with a lumen in which a tether line may pass therethrough, according to some embodiments of the invention.

FIGS. 40A-B illustrate embodiments of adjustment mechanisms comprising a beaded tether.

FIGS. 41A-F various show embodiments of adjustment mechanisms that comprise a sleeve that may be part of a tissue anchor.

FIGS. 42-43 illustrate embodiments of adjustment mechanisms as part of a double-ended anchor.

DETAILED DESCRIPTION OF THE PREFERRED EMBODIMENTS

A. Anatomy of the Pharynx

Figure 1A:
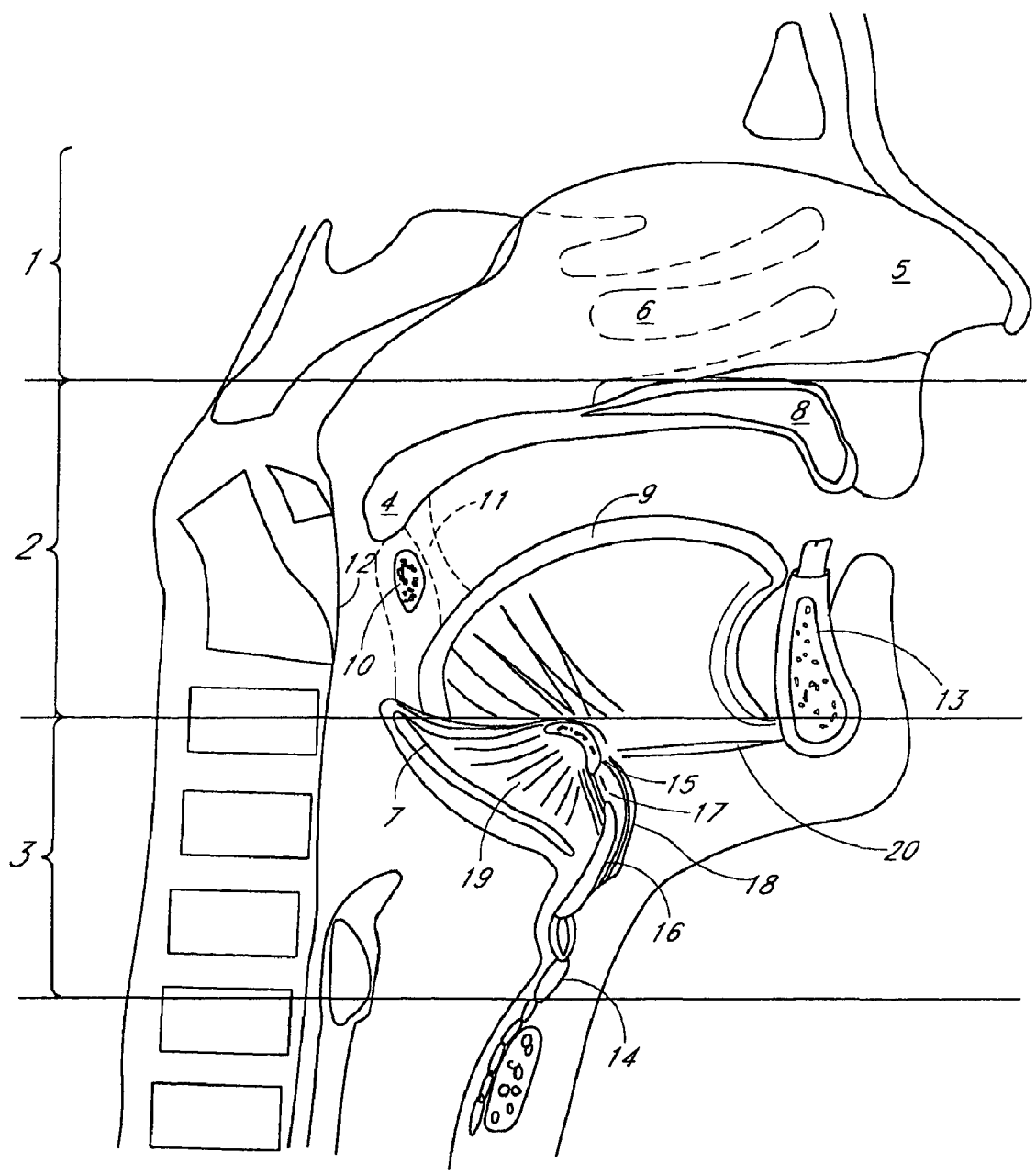
FIGS. 1A and 1B are schematic sagittal views of the pharynx before and during volumetric tongue ablation using an RF electrode.

FIG. 1A is a sagittal view of the structures that comprise the pharyngeal airway and may be involved in obstructive sleep apnea. The pharynx is divided, from superior to inferior, into the nasopharynx 1, the oropharynx 2 and the hypopharynx 3. The nasopharynx 1 is a less common source of obstruction in OSA. The nasopharynx is the portion of the pharynx above the soft palate 4. In the nasopharynx, a deviated nasal septum 5 or enlarged nasal turbinates 6 may occasionally contribute to upper airway resistance or blockage. Only rarely, a nasal mass, such as a polyp, cyst or tumor may be a source of obstruction.

The oropharynx 2 comprises structures from the soft palate 4 to the upper border of the epiglottis 7 and includes the hard palate 8, tongue 9, tonsils 10, palatoglossal arch 11, the posterior pharyngeal wall 12 and the mandible 13. The mandible typically has a bone thickness of about 5 mm to about 10 mm anteriorly with similar thicknesses laterally. An obstruction in the oropharynx 2 may result when the tongue 9 is displaced posteriorly during sleep as a consequence of reduced muscle activity during REM sleep. The displaced tongue 9 may push the soft palate 4 posteriorly and may seal off the nasopharynx 1 from the oropharynx 2. The tongue 9 may also contact the posterior pharyngeal wall 12, which causes further airway obstruction.

The hypopharynx 3 comprises the region from the upper border of the epiglottis 7 to the inferior. border of the cricoid cartilage 14. The hypopharynx 3 further comprises the hyoid bone 15, a U-shaped, free floating bone that does not articulate with any other bone. The hyoid bone 15 is attached to surrounding structures by various muscles and connective tissues. The hyoid bone 15 lies inferior to the tongue 9 and superior to the thyroid cartilage 16. A thyrohyoid membrane 17 and a thyrohyoid muscle 18 attaches to the inferior border of the hyoid 15 and the superior border of the thyroid cartilage 16. The epiglottis 7 is infero-posterior to the hyoid bone 15 and attaches to the hyoid bone by a median hyoepiglottic ligament 19. The hyoid bone attaches anteriorly to the infero-posterior aspect of the mandible 13 by the geniohyoid muscle 20.

B. Tongue Remodeling

Embodiments of the present invention provide methods and devices for manipulating the airway. It is hypothesized that the laxity in pharyngeal structures contributes to the pathophysiology of obstructive sleep apnea, snoring, upper airway resistance and sleep disordered breathing. This laxity may be intrinsic to the oropharyngeal structures and/or may be affected by interrelationships between pharyngeal structures and other body structures. For example, in some studies, the cure rates in selected patients undergoing UPPP is as low as 5% to 10%. (Sher A E et al., "The efficacy of surgical modifications of the upper airway in adults with obstructive sleep apnea syndrome" Sleep, 1996 February; 19(2):156-77, herein incorporated by reference). These low cure rates may be affected by continued occlusion of the airway by structures unaffected by the surgery, such as the tongue. By biasing at least a portion of the posterior tongue or base of the tongue in at least a generally anterior and/or lateral direction, functional occlusion of the oropharynx may be prevented or reduced. Typically, this bias may be created by altering a distance or tension between a location in the tongue and an anchoring site, such as the mandible. In other instances, the bias may be created by altering the length or amount of a structure located in the tongue. In some instances, the bias provided to the tongue may only affect the mechanical characteristics tongue during tongue movement or in specific positions or situations. Thus, the dynamic response of the tongue tissue to mechanical forces or conditions may or may not occur with static changes, although static changes typically will affect the dynamic response of the tongue tissue. The embodiments of the invention described herein, however, are not limited to this hypothesis.

Although surgical and non-surgical techniques for biasing the tongue anteriorly are currently available, these techniques suffer from several limitations. For example, the Repose® system (InfluENT® Medical, New Hampshire) utilizes a bone screw attached to the lingual cortex of the mandible and a proline suture looped through the posterior tongue and bone screw, where the suture ends are tied together at some point along the suture loop to prevent posterior tongue displacement. In one study of 43 patients, four patients developed infections of the floor of the mouth and required antibiotics. One patient developed dehydration caused by painful swallowing, requiring intravenous fluids, and another patient developed delayed GI bleeding requiring hospitalization. (Woodson BT, "A tongue suspension suture for obstructive sleep apnea and snorers", Otolaryngol Head Neck Surg. 2001 March; 124(3):297-303). In another study of 19 patients undergoing combined UPPP and Repose® implantation, two patients developed submandibular infection requiring antibiotics, and one patient developed a hematoma in the floor of the mouth requiring drainage. In addition, one patient extruded the suture four weeks after implantation and another patient developed a persistent lump/globus sensation at the base of the tongue requiring removal of the Repose® system. (Miller FR et al., "Role of the tongue base suspension suture with The Repose® System bone screw in the multilevel surgical management of obstructive sleep apnea", Otolaryngol Head Neck Surg. 2002 April; 126(4):392-8).

By developing a tongue remodeling system that can be adjusted before, during and/or after the initial implantation procedure, a device and method for treating a patient with breathing problems may be better tolerated and less prone to treatment failure. For example, by adjusting the tension or bias of the implant, suture migration, suture extrusion, and/or dysphagia may be avoided or corrected. In another embodiment of the invention, the tongue remodeling system alters the structural characteristics of the tongue with an anterior or lateral bias force rather than a fixed length anchoring of the tongue to a body structure. This bias may reduce dysphagia or odynophagia associated with existing tongue suspension devices and procedures. In other embodiments, the tongue may be remodeled by altering the tissue compliance of at least a portion of the tongue. By inserting a prosthesis into the tongue tissue, tongue tissue compliance is changed and may alter the tongue response to forces acting during obstructive sleep apnea. The change in compliance may or may not be associated with a change in the position of the tongue. In some instances, embodiments of the tongue remodeling system can be implanted through an antero-inferior access site of the mandible. Implantation of the system that avoids the transoral route may improve infection rates that occur with other tongue related devices and procedures.

U.S. Provisional Application No. 60/650,867, U.S. Provisional Application No. 60/726,028, and U.S. Utility patent application Ser. No. 11/349,067, all of which are herein incorporated by reference in their entirety, disclose many embodiments for a tongue remodeling system comprising a soft tissue anchor implanted into the tongue and attached by a tether to an anchoring site. The anchoring site typically is a bony structure adjacent to the tongue, such as the mandible or hyoid bone, but in other embodiments may be another soft tissue site when using a tether having a soft tissue anchor at each end. By exerting a force or otherwise altering the mechanical tissue characteristics between the soft tissue anchor and the anchoring site, tongue remodeling may be achieved to reduce the risk of airway obstruction.

Figure 2A:
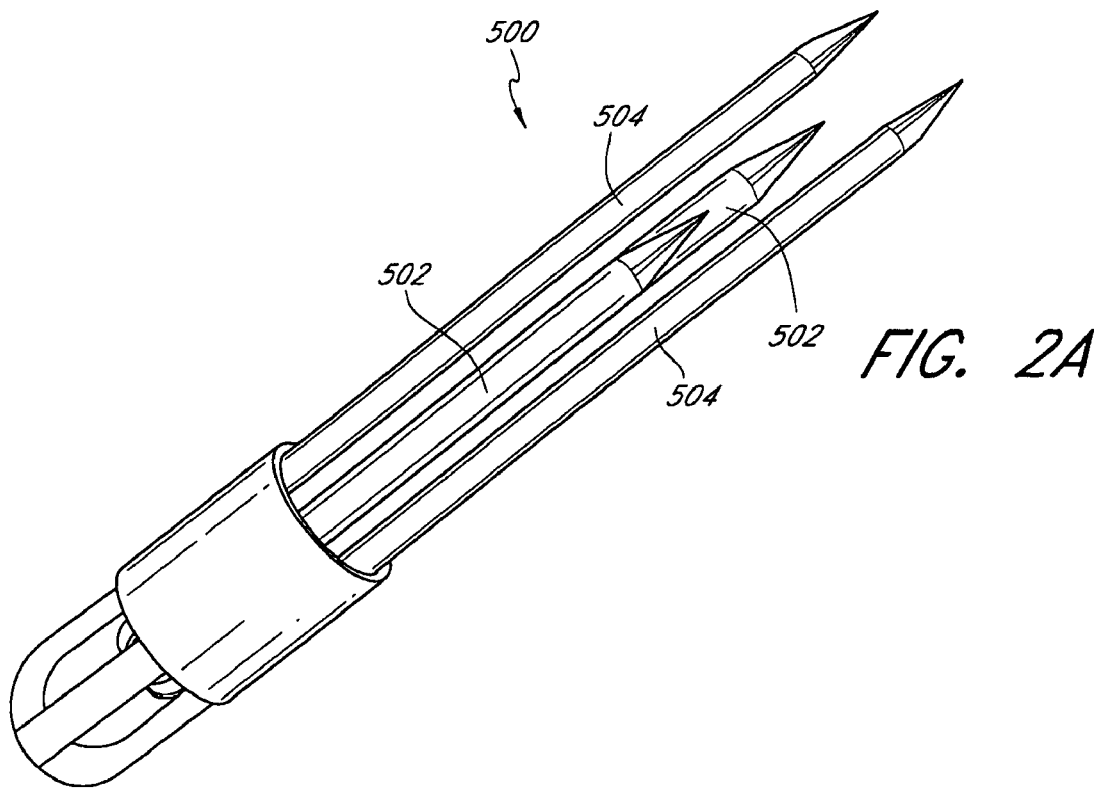
FIGS. 2A and 2B are perspective views of the preferred embodiment of a distal anchor in the delivery and deployed configurations, respectively.
Figure 2B:
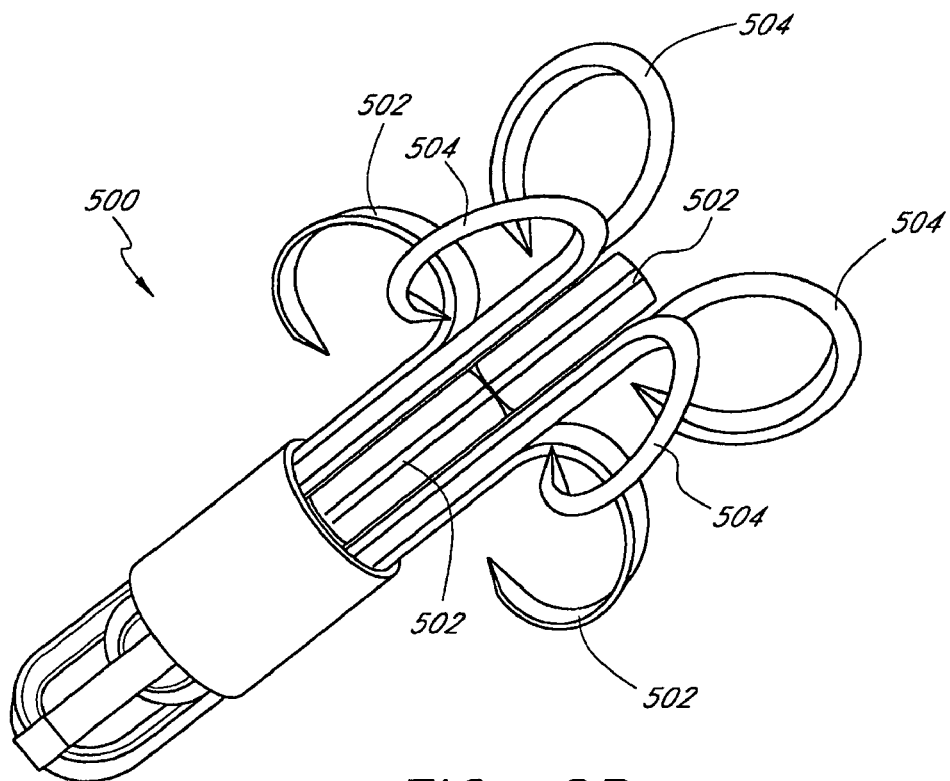

FIGS. 2A and 2B illustrate a preferred embodiment of the soft tissue anchor 500 comprising a plurality of expandable hook elements 502, 504. U.S. Pat. No. 5,988,171 and U.S. Pat. No. 6,161,541, both herein incorporated by reference in their entirety, disclose additional methods of performing glossopexy, or tongue anchoring.

Figure 1B:
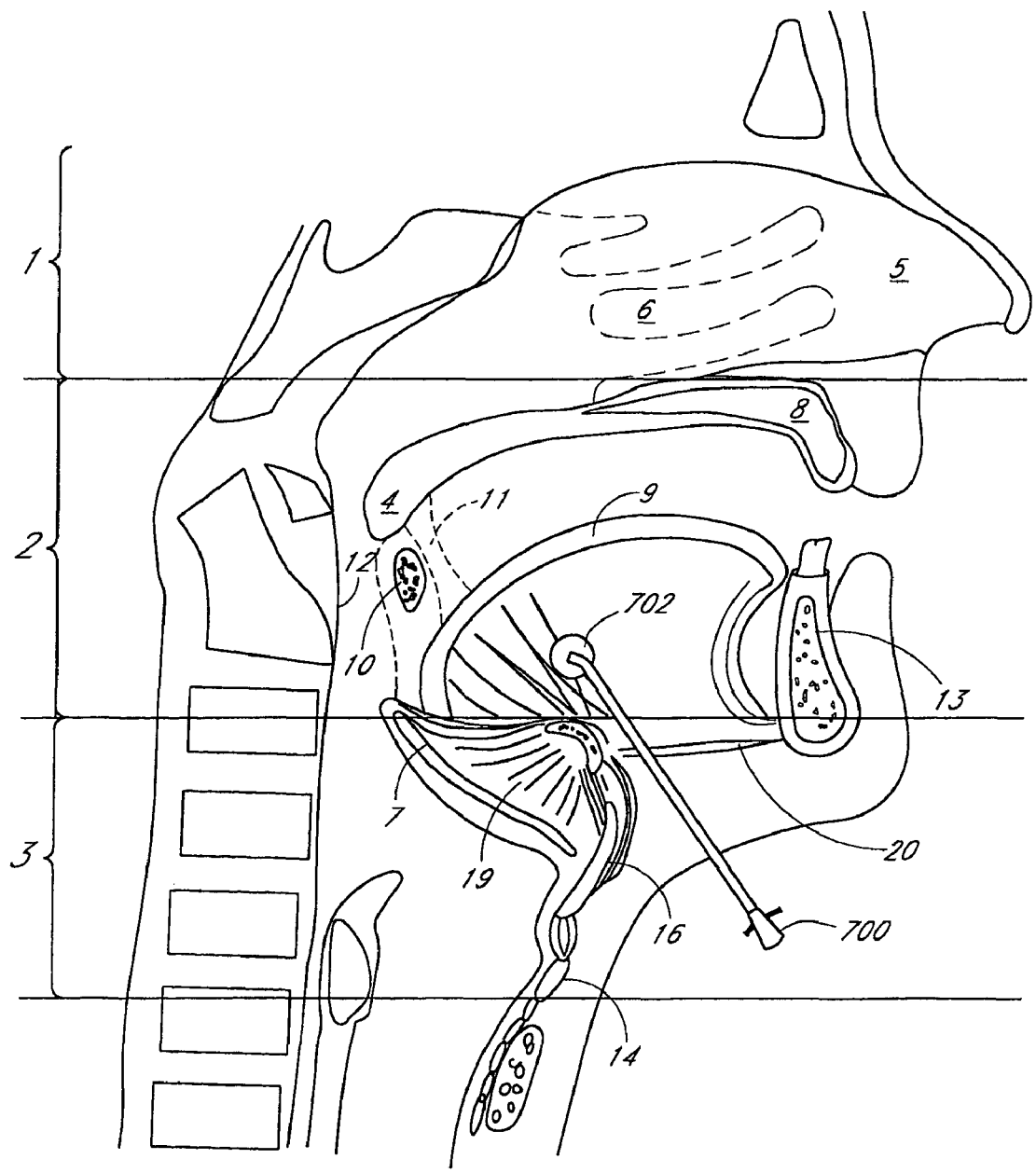

The results achieved by the above tongue remodeling systems may be further enhanced by reducing the mass of the tongue in combination with glossopexy. Although volumetric tongue reduction may be performed using any of a variety of known surgical techniques used to treat macroglossia, or enlarged tongue, preferred embodiments of volumetric tongue reduction involve the use of a variety of ablation techniques and devices such as those disclosed in U.S. Pat. No. 5,624,439, U.S. Pat. No. 5,738,114, U.S. Pat. No. 6,159,208, U.S. Pub. No. 2005/0234439 and U.S. Provisional Application No. 60/556,611, all herein incorporated by reference in their entirety. FIG. 1B depicts the use of an ablation electrode 700 to form a cavity 702 in the tongue 9. The cavity 702, however, need not be completely surrounded by tongue tissue and need not be limited to a single cavity. In other embodiments, one or more cavities formed may be exposed to the anterior, posterior, or lateral surfaces of the tongue.

U.S. Pub. No. 2005/0234439 and U.S. Provisional Application No. 60/556,611 also describe the use of sutures or staples to close a cavity or space formed in the tongue following tongue ablation, and also describe the anchoring of the suture at a sublingual site. The various closure and anchoring techniques disclosed in these references, however, involve unwieldy suturing procedures that are difficult and time-consuming to use. Instead, by combining volumetric tongue reduction with tongue anchoring using a tethered soft tissue anchor, closure and/or anchoring of an ablation cavity may be achieved using a simple insertion and withdrawal procedure.

Figure 3A:
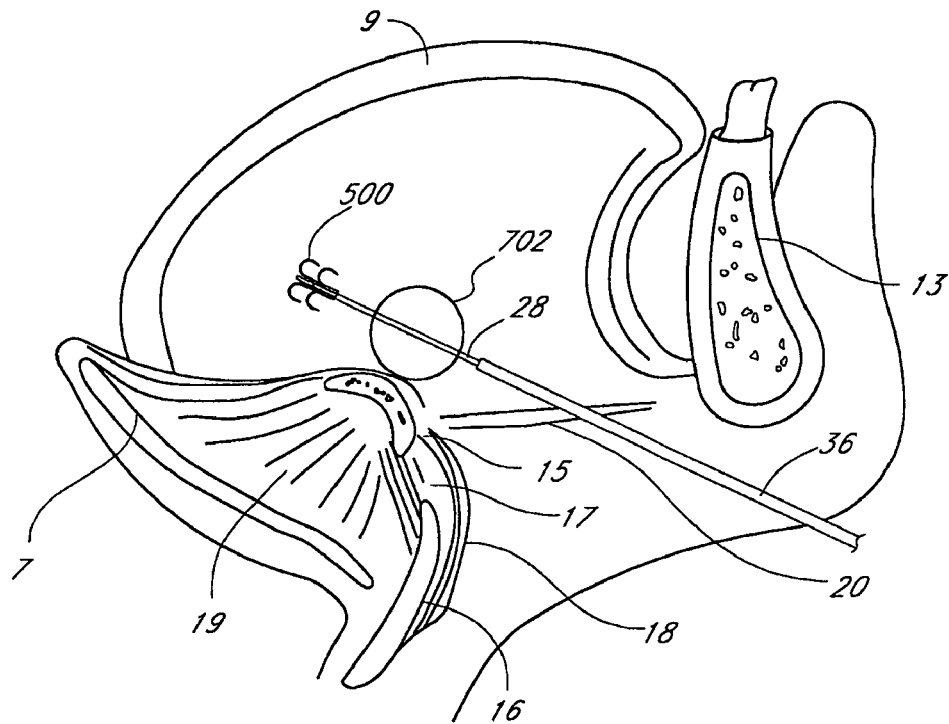
FIGS. 3A and 3B are schematic sagittal views of an ablation cavity during and after glossopexy.

Referring to FIG. 3A, in one embodiment of the invention, following the formation of a space or cavity 702 in the tongue, a soft tissue anchor delivery tool 36 is inserted into the tongue 9 and through the space 702 and the tethered tissue anchor 500 is deployed distal to the space 702 with respect to the anchoring site 704 for the tether portion 28 of the tethered tissue anchor 500. Upon tensioning of the tether 28, as depicted in FIG. 3B, the tension causes collapse of the cavity 702 and reduces the volume of the tongue 9.

Figure 3B:
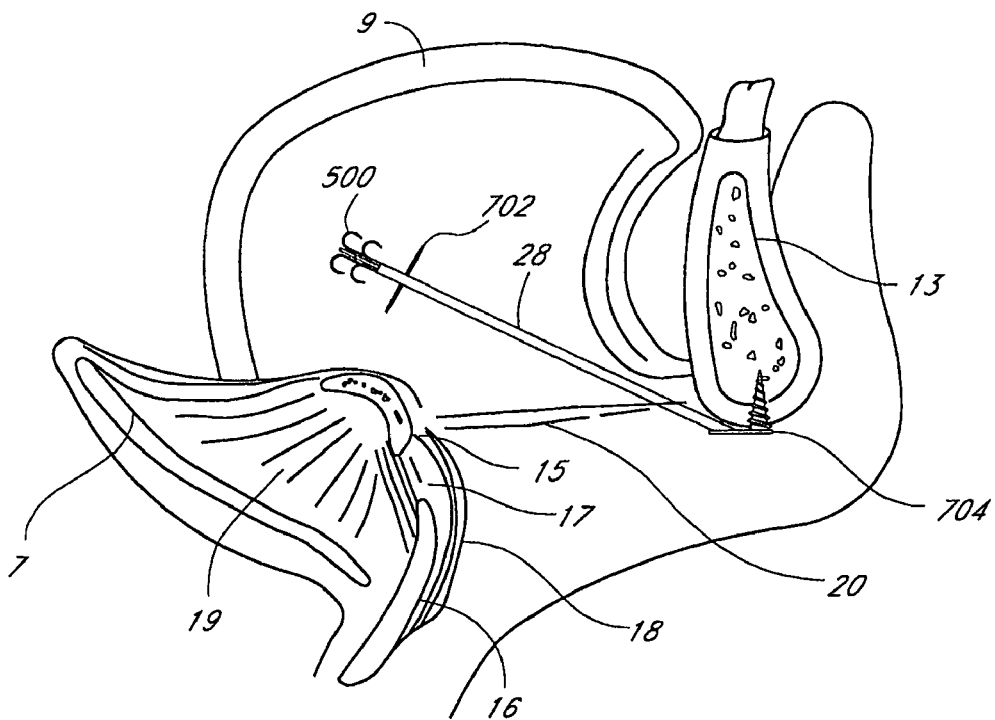
Figure 4A:
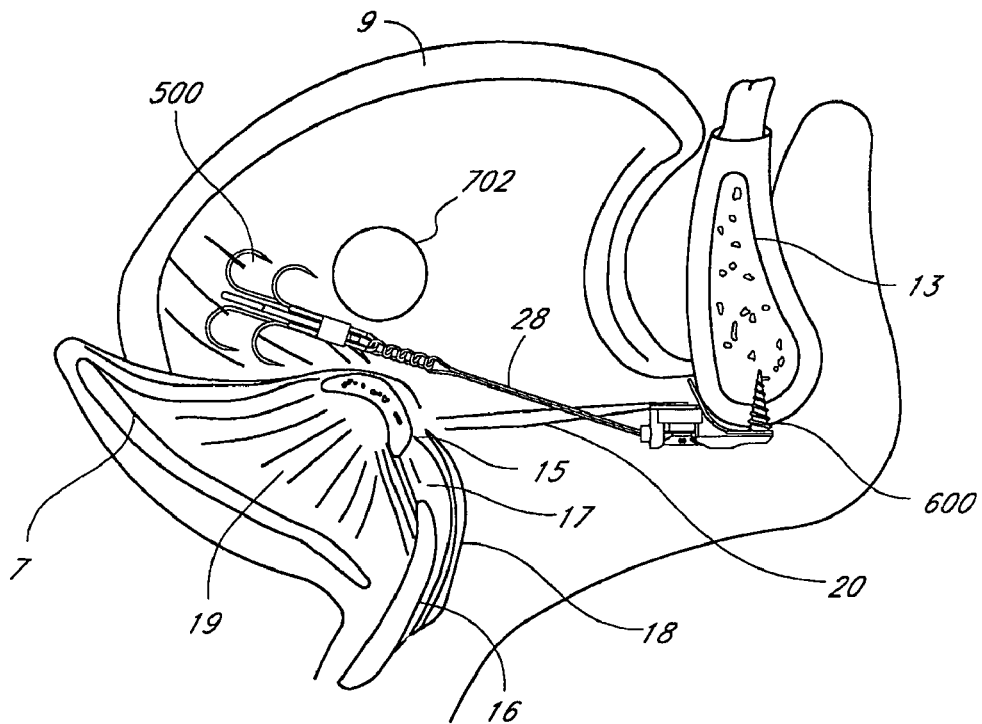
FIGS. 4A and 4B are schematic sagittal views of another embodiment of the invention illustrating tongue remodeling.
Figure 4B:
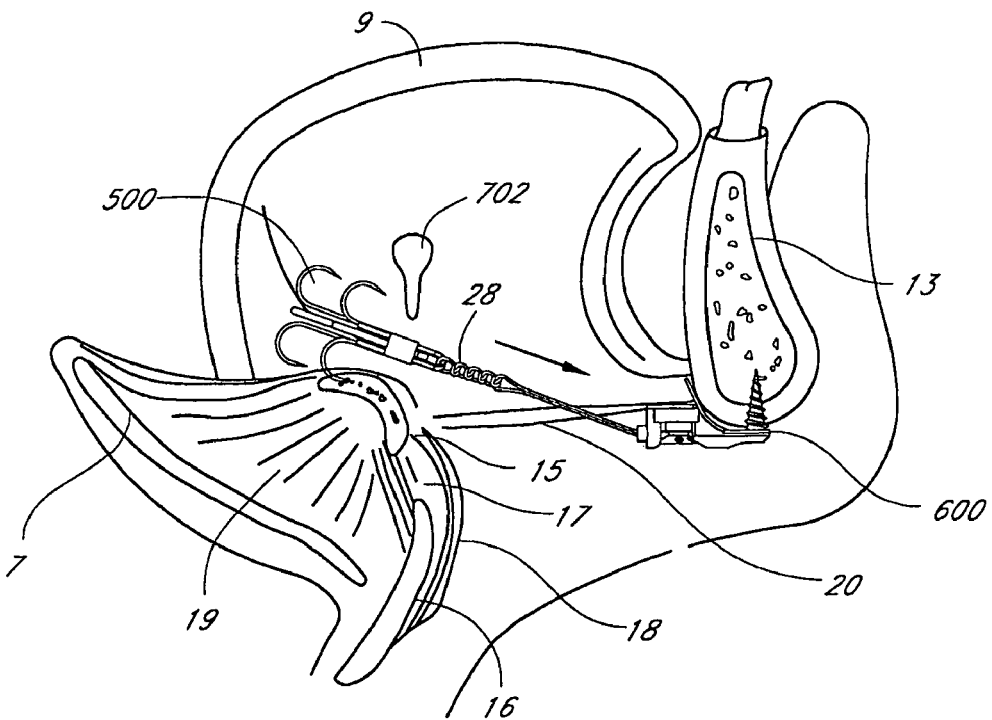

Although the procedure depicted in the FIGS. 3A and 3B show the insertion pathway, as occupied by the tether portion 28 of the tethered tissue anchor 500, as intersecting the space 702 formed in the tongue 9, in other embodiments of the invention, the insertion pathway of the tethered tissue anchor 500 need only be proximate to a cavity 702 to cause collapse or deformation of the cavity 702 and need not intersect the cavity 702. The insertion pathway may be linear, non-linear, curved and/or angled. Non-linear insertion pathways may be formed, for example, by using non-linear delivery tools or by changing the angulation of the delivery tool during insertion. The spacing between the tissue anchor 500 and the cavity 702 may also vary. In some instances, one or more hooks elements 502, 504 may protrude into the cavity 702. FIGS. 4A and 4B, for example, depict a tissue anchor 500 inserted adjacent to a cavity 702 which can still reduce the volume of the tongue 9 upon deployment. FIGS. 4A and 4B further illustrate the optional use of an adjustment assembly 600 at a mandibular anchoring site 704. An adjustment assembly may also be used in conjunction with non-tissue anchor glossopexy procedures, including procedures using sutures to engage the tongue tissue.

One of skill in the art will understand that numerous variations of tongue anchoring with volumetric tongue reduction are possible by combining one or more different tether types and/or implantation sites with a variety of tongue ablation patterns.

Figure 5A:
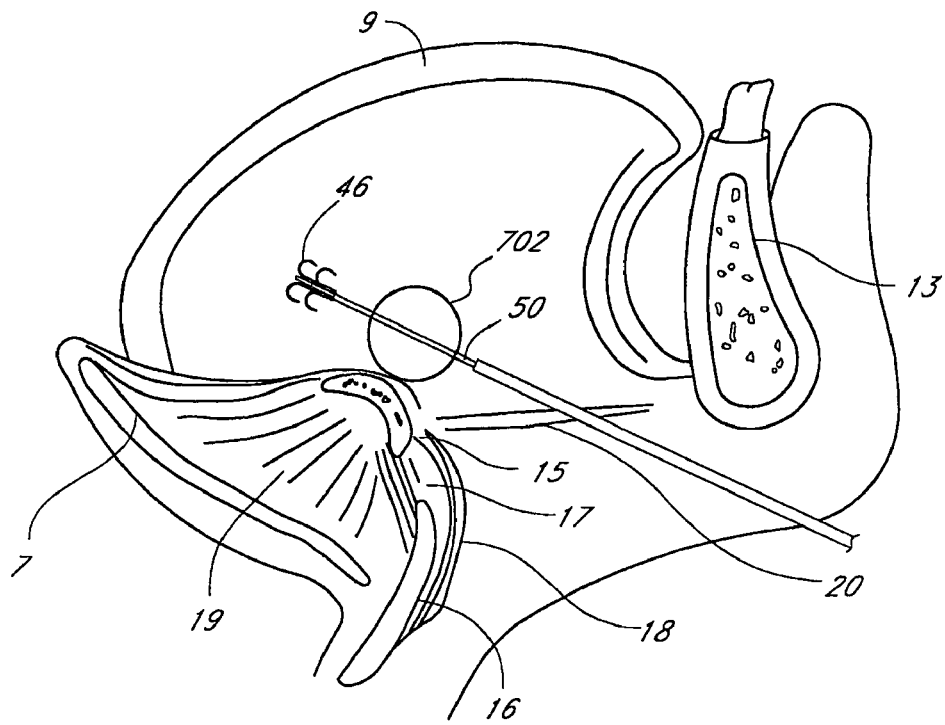
FIGS. 5A and 5B are schematic sagittal views of another embodiment of the invention illustrating tongue remodeling.
Figure 5B:
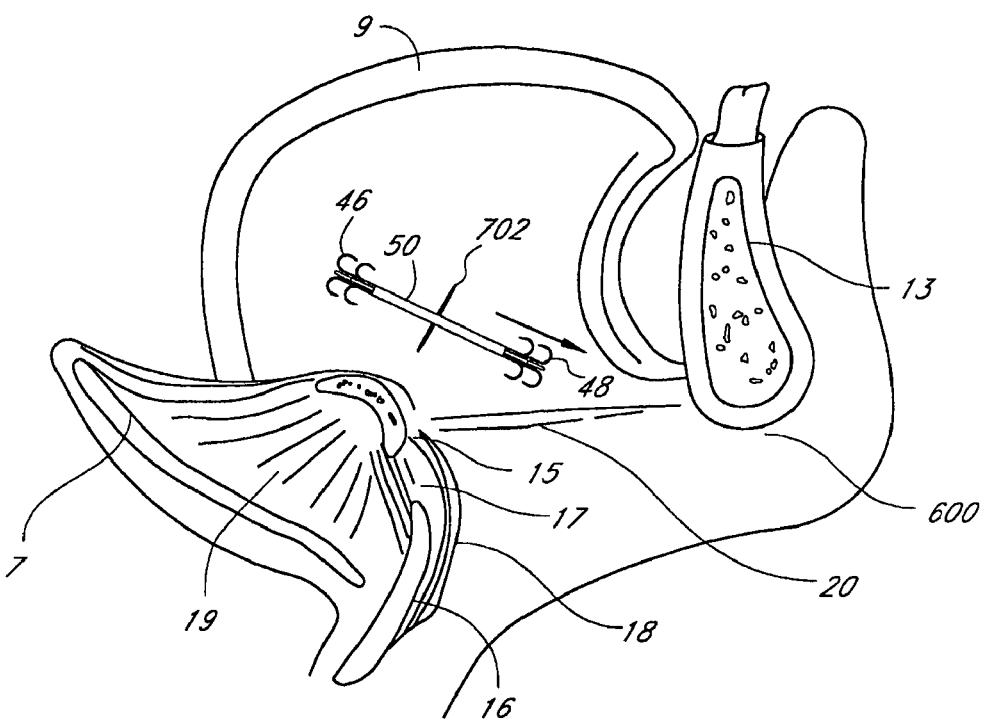
Figure 14:
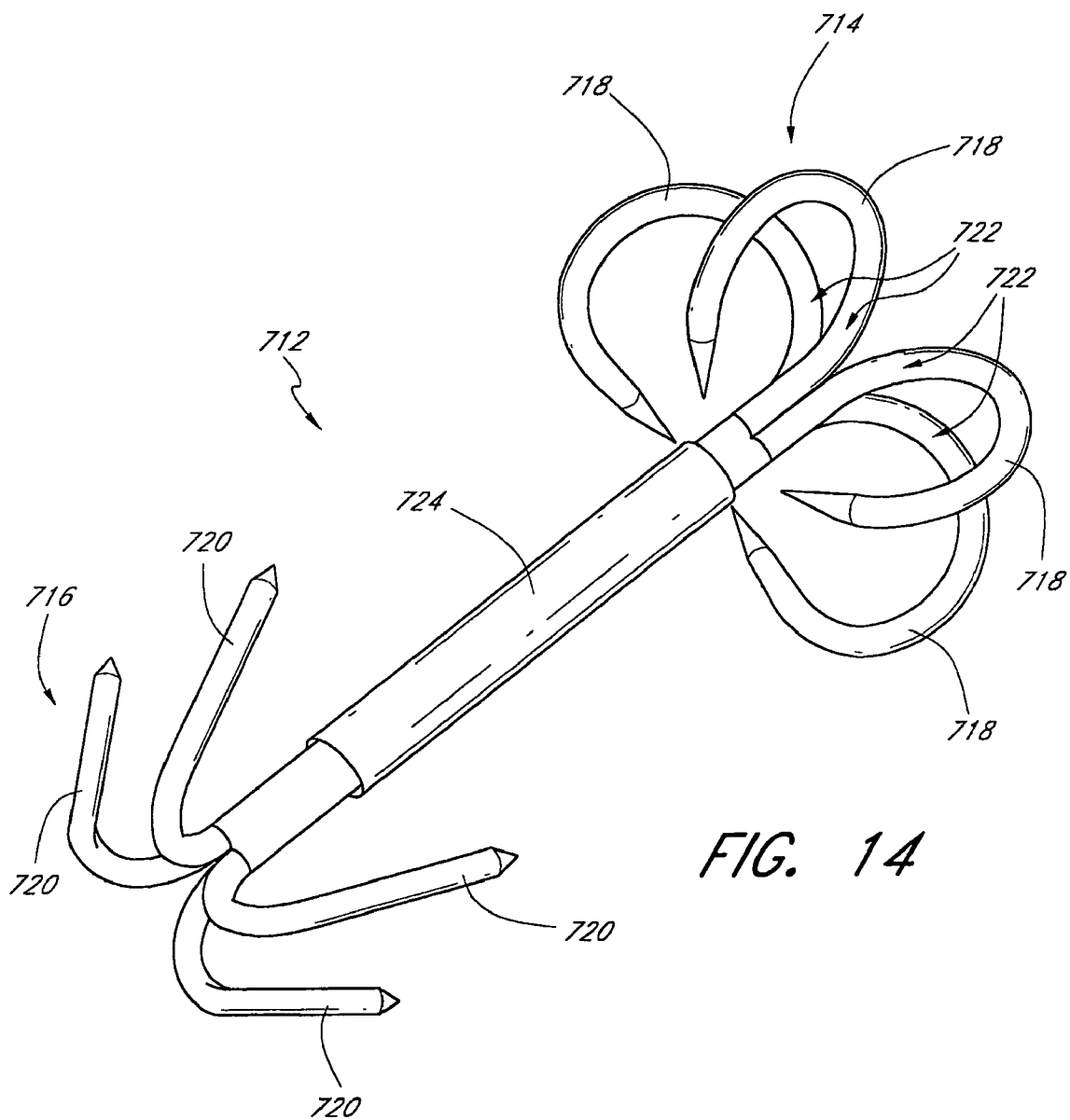
FIG. 14 is an isometric elevational view of another embodiment of the invention comprising a tissue anchor.

FIGS. 5A and 5B illustrate one embodiment of a tether with dual tissue anchors 46, 48 used to collapse a cavity 702. FIG. 14 depicts an alternative embodiment of the invention, comprising a tissue anchor 712 having a distal tissue-engaging member 714 and a proximal tissue-engaging member 716 but lacking a tether or a flexible member between the two tissue-engaging members 714, 716. Each tissue-engaging member 714, 716 may comprise at least one deployable barb 718, 720, and preferably a plurality of barbs 718, 720. Each barb may have the same or different size, shape or material composition compared to the other barbs in the tissue anchor 712.

Figure 15A:
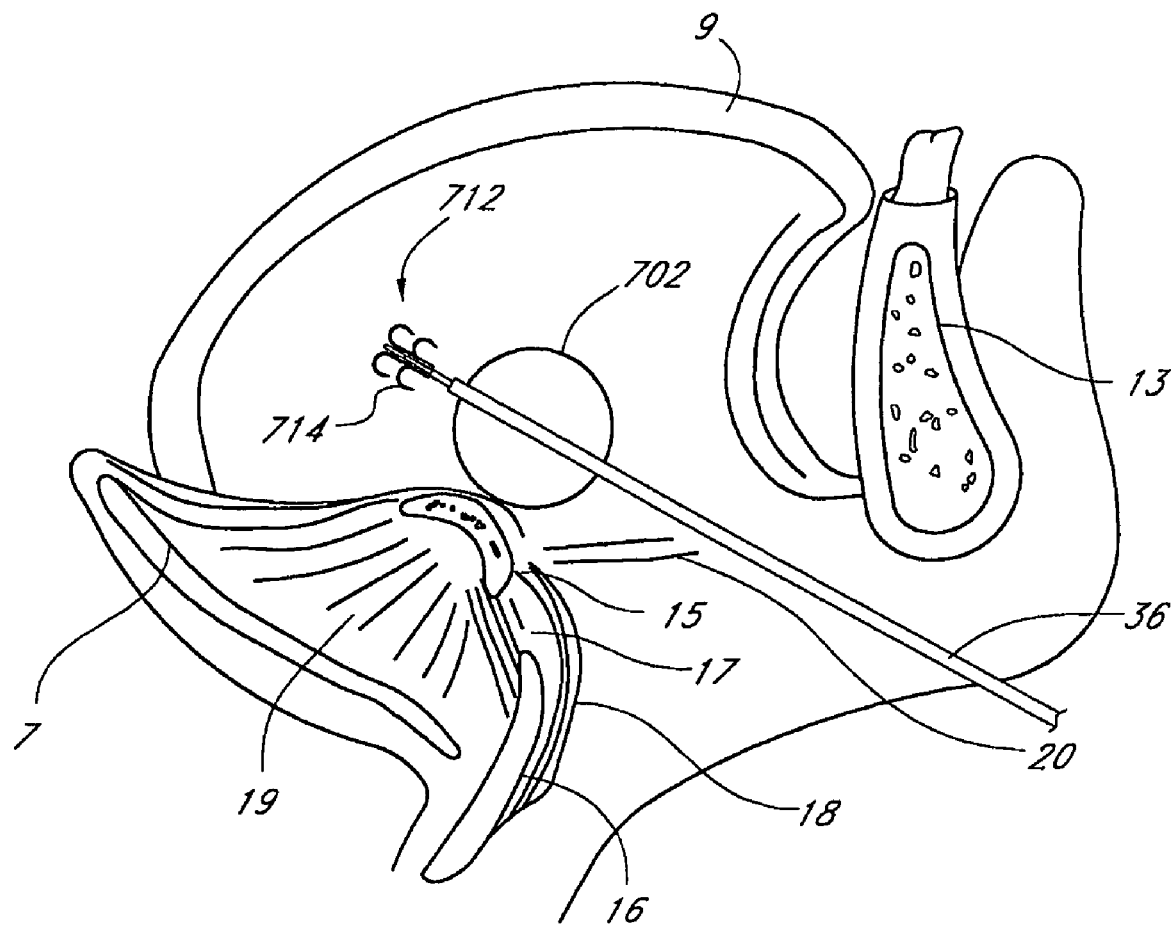
FIGS. 15A to 15C depict the implantation of the tissue anchor in FIG. 14 into a tongue with a cavity.
Figure 15B:
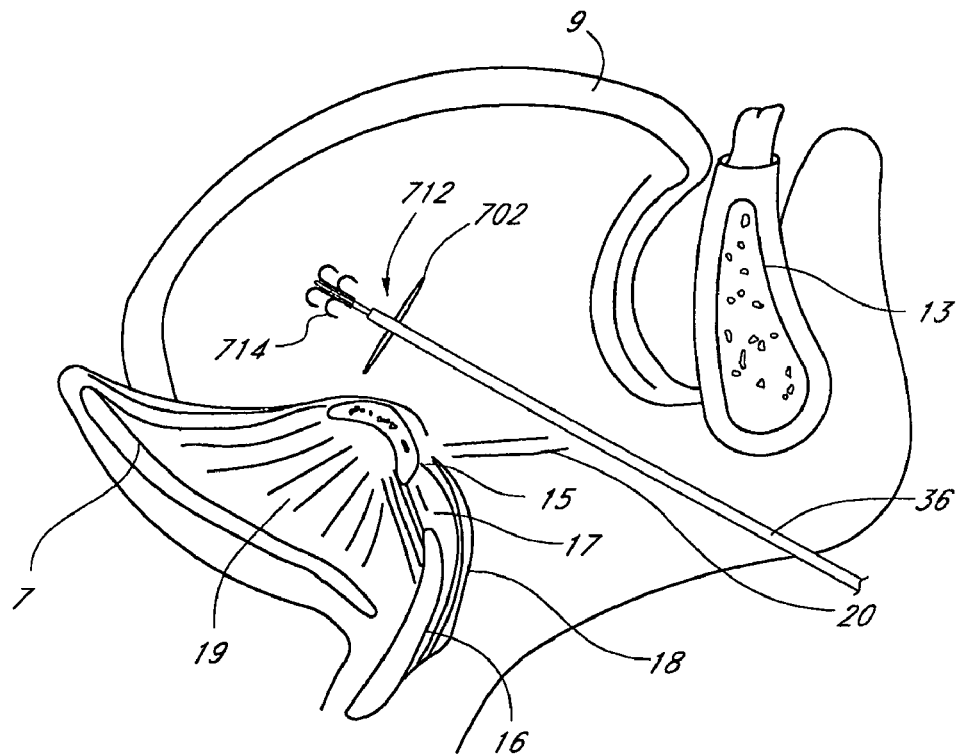
Figure 15C:
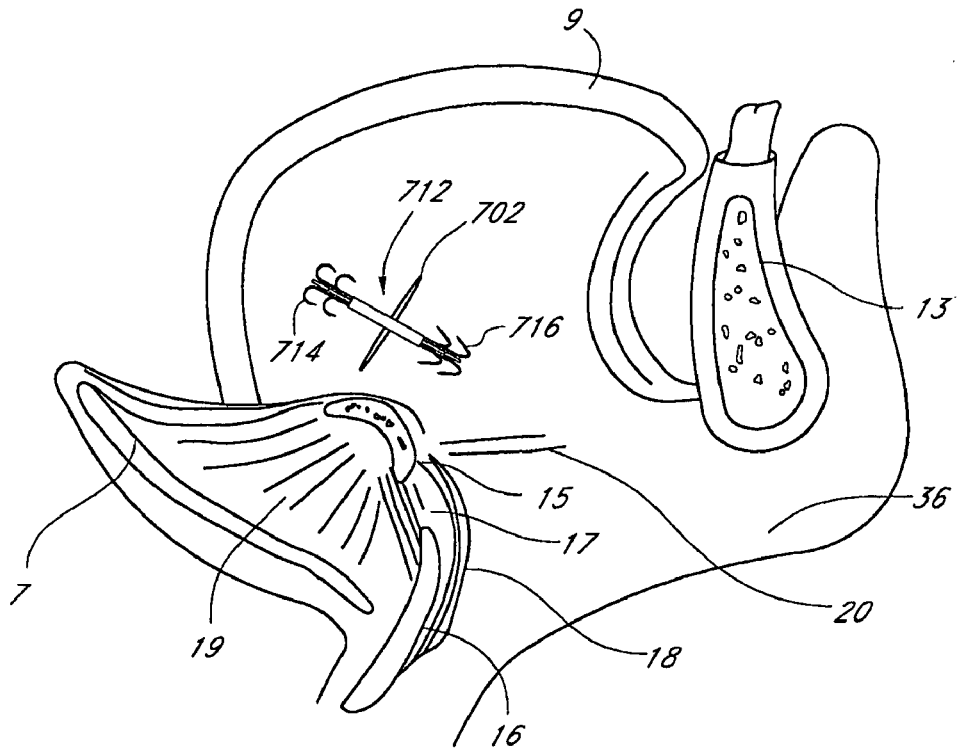

In the particular embodiment depicted in FIG. 14, the distal tissue-engaging member 714 comprises a plurality of curved barbs 718 and the proximal tissue-engaging member 716 comprises a plurality of straight barbs 720. This particular arrangement of curved and straight barbs 718, 720 may facilitate loading and implantation of the tissue anchor 712 with respect to the tubular delivery tool 36, as the tips of the straight barbs 720 have a delivery configuration where the tips present a flatter angle to the inner surface of the delivery tool lumen compared to the tips of the curved barbs 720, thereby presenting less resistance to loading and delivery. This particular tissue anchor 712 comprises four identical anchor elements 722, each with a curved barb 718 at one end and a straight barb 720 at the other end, with the four anchor elements joined in a radially spaced arrangement and optionally covered at their middle segments by a sleeve 724. The middle segments may be stiff or compliant. The length of the middle segments may also vary, depending upon patient anatomy or pathology. This and other embodiments of the invention, however, are not limited to this configuration or functionality. Referring to FIGS. 15A to 15C, the tissue anchor 712 may be deployed by inserting a delivery tool 36 loaded with the tissue anchor 712 through a cavity 702 and then releasing the distal tissue-engaging member 714 to engage the tongue tissue just distal to the cavity 702. The delivery tool 36 is then partially withdrawn proximally, as shown in FIG. 15B, to collapse the cavity 702, before releasing the proximal tissue-engaging member 716.

Figure 6A:
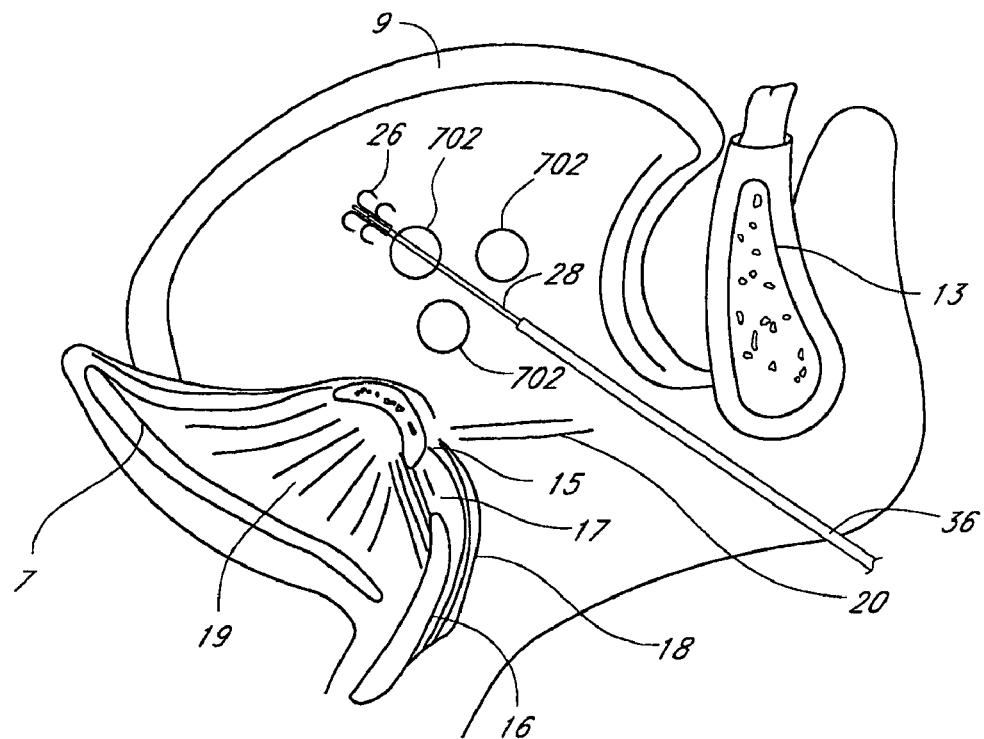
FIGS. 6A and 6B are schematic sagittal views of another embodiment of the invention illustrating tongue remodeling.
Figure 6B:
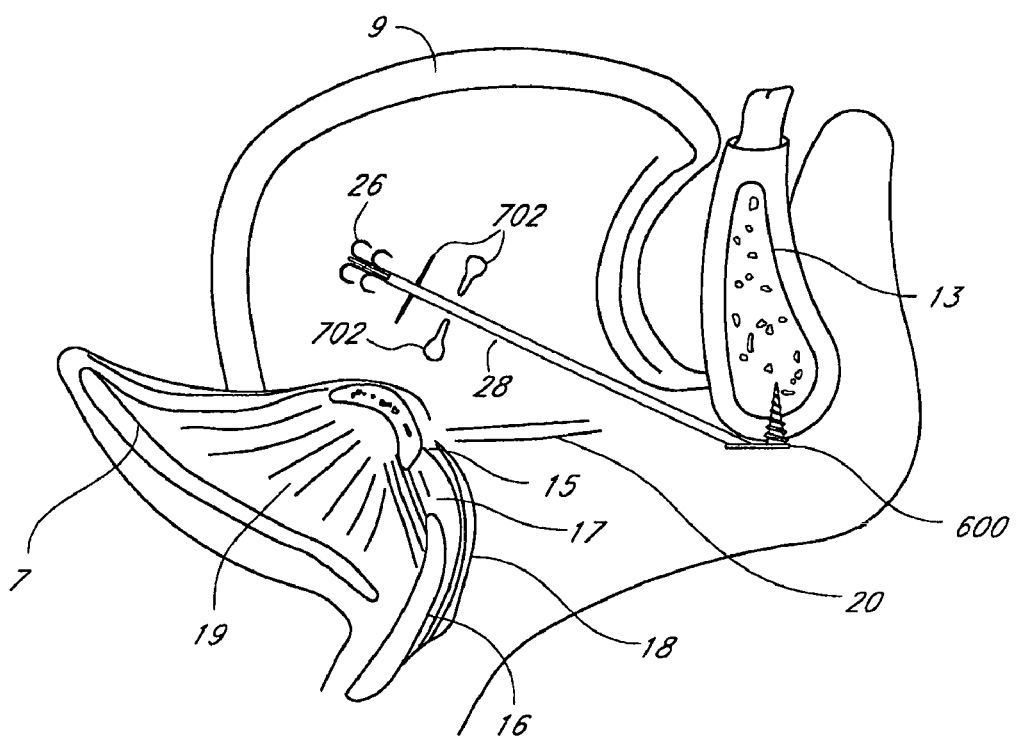
Figure 7A:
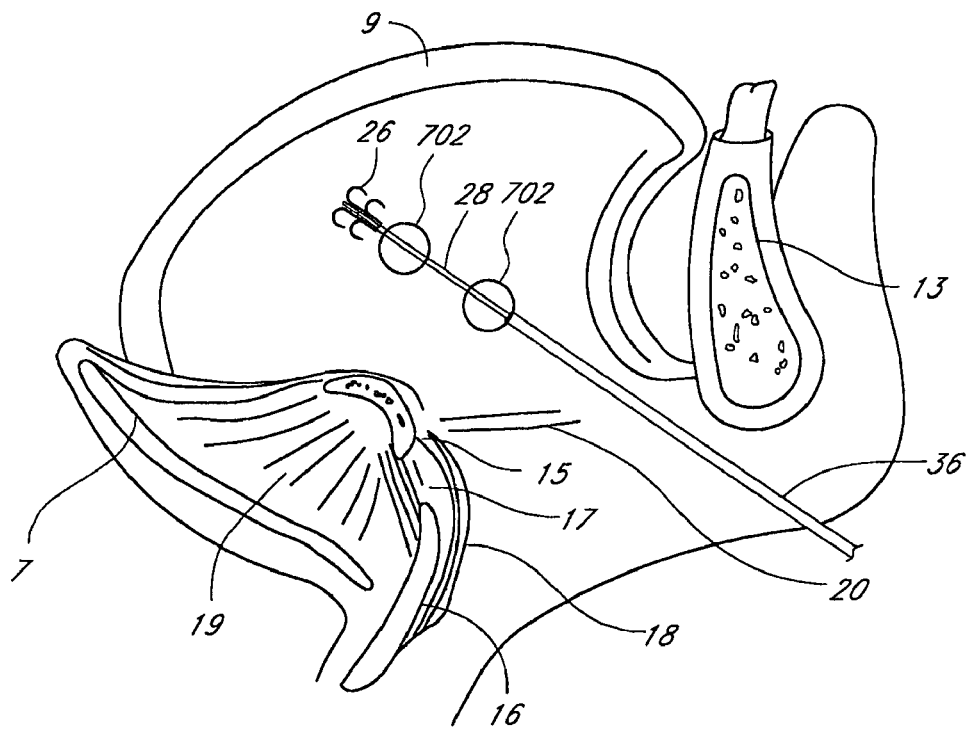
FIGS. 7A and 7B are schematic sagittal views of another embodiment of the invention illustrating tongue remodeling.
Figure 7B:
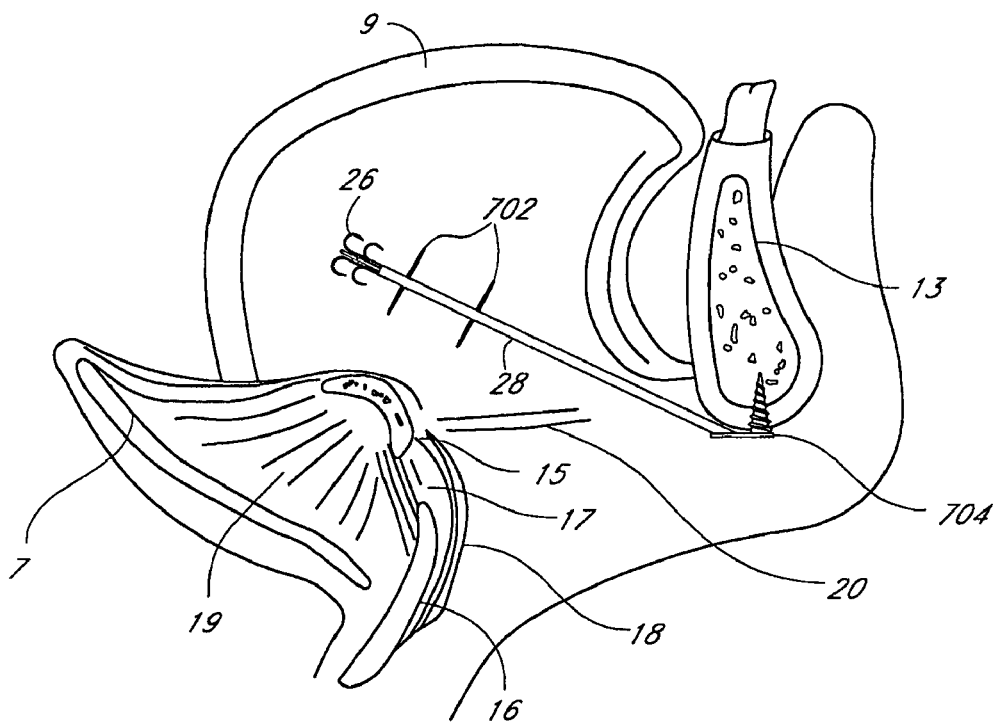
Figure 8A:
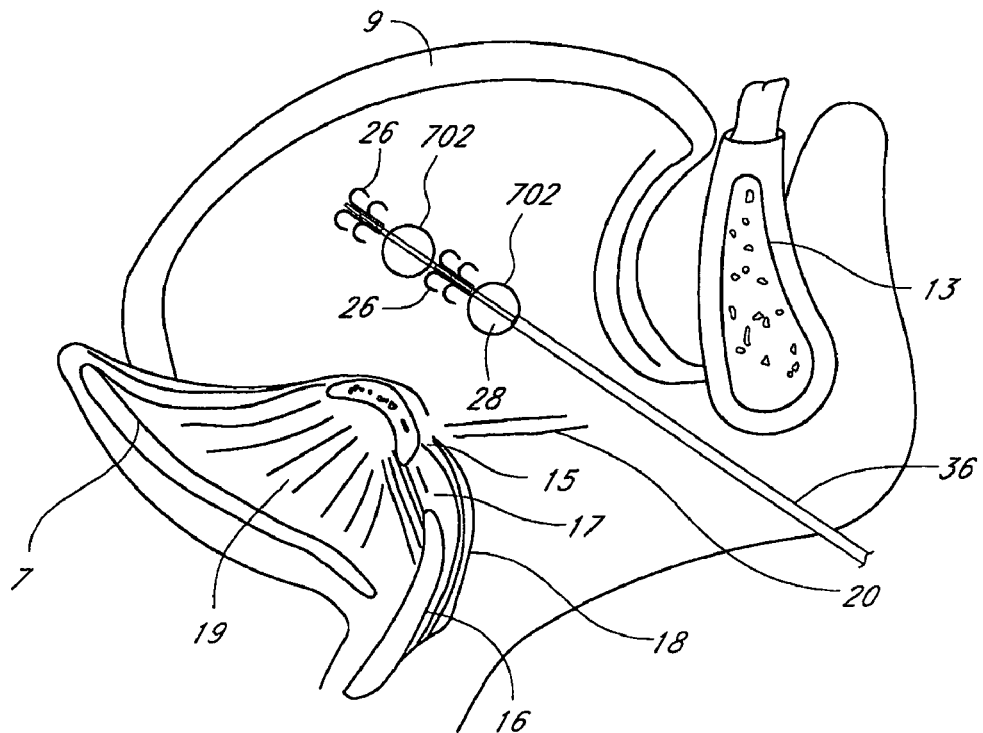
FIGS. 8A and 8B are schematic sagittal views of another embodiment of the invention illustrating tongue remodeling.
Figure 8B:
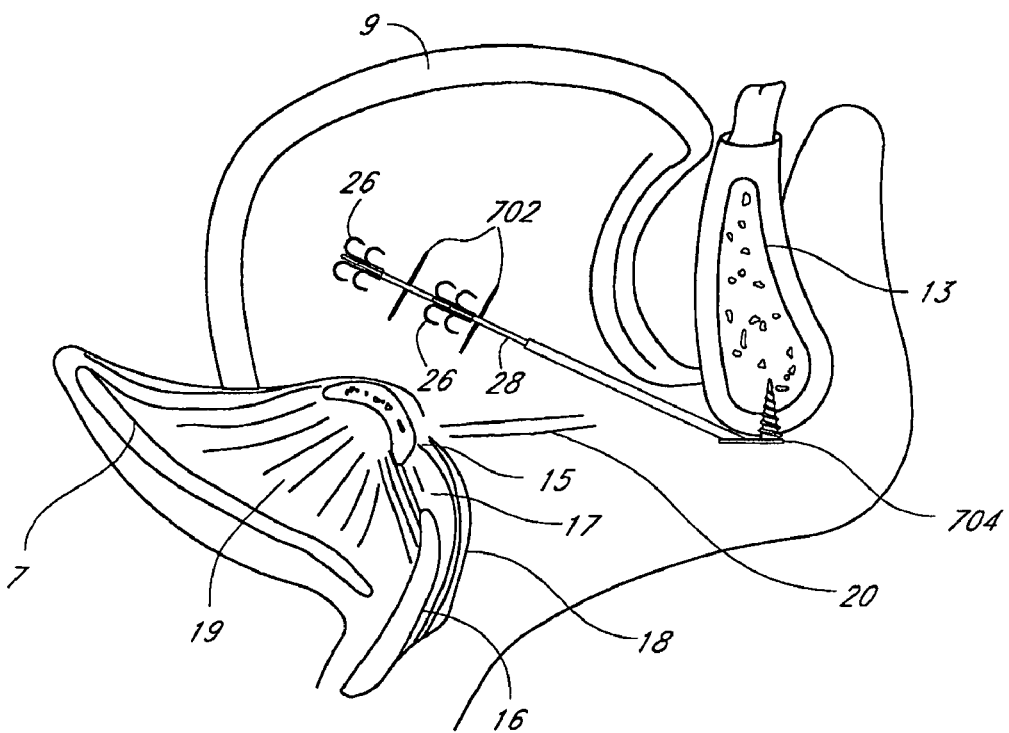

FIGS. 6A and 6B illustrate one embodiment of a tethered tissue anchor 26 implanted in a tongue 9 having multiple cavities 702. All, some or none of the cavities 702 may be penetrated by the tether 28 of the tethered tissue anchor 26. For example, in FIGS. 7A and 7B, a tethered tissue anchor 26 is implanted in a tongue 9 having multiple cavities 702, wherein anchor is inserted through multiple cavities 702. In a further embodiment shown in FIGS. 8A and 8B, a tether 28 having multiple anchors 26 arranged in a serial configuration along the tether 28 may be used to distribute the collapse force of the anchoring system at multiple sites, rather than a single site at the distal most end of the tether 28.

Figure 9A:
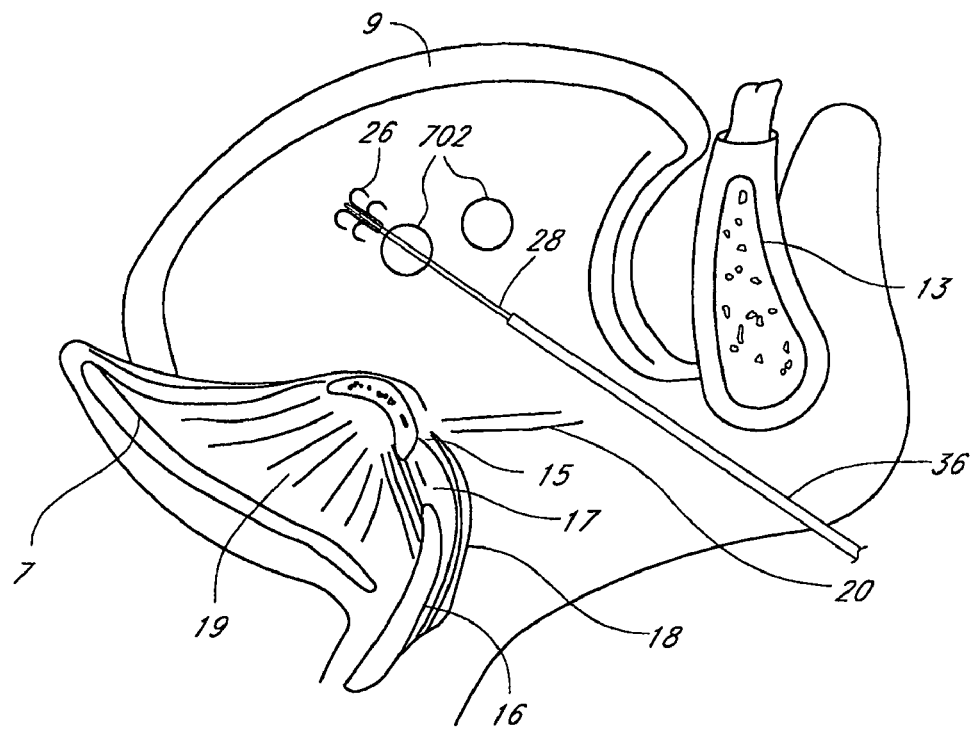
FIGS. 9A and 9B are schematic sagittal views of another embodiment of the invention illustrating tongue remodeling.
Figure 9B:
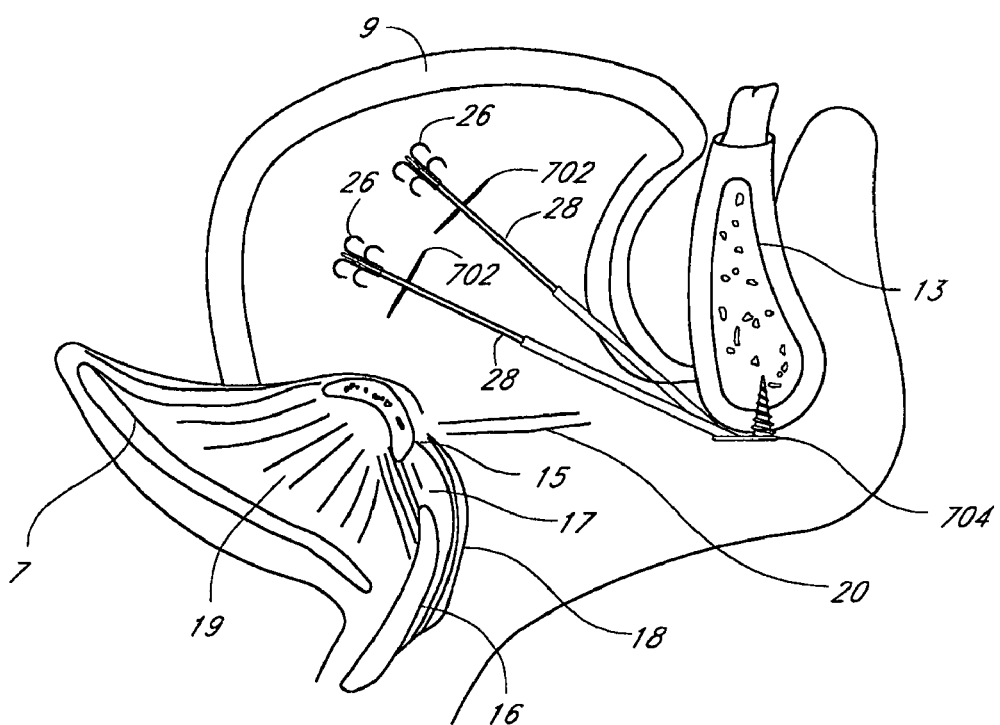

FIGS. 9A and 9B illustrate one embodiment of the invention comprising multiple cavities 702 and multiple tethered anchors 26, where the anchors 26 share the same anchoring site 704. Each cavity and each anchor, however, need not be identical in shape or configuration. Each anchor may have the same or a different anchoring site.

Figure 10A:
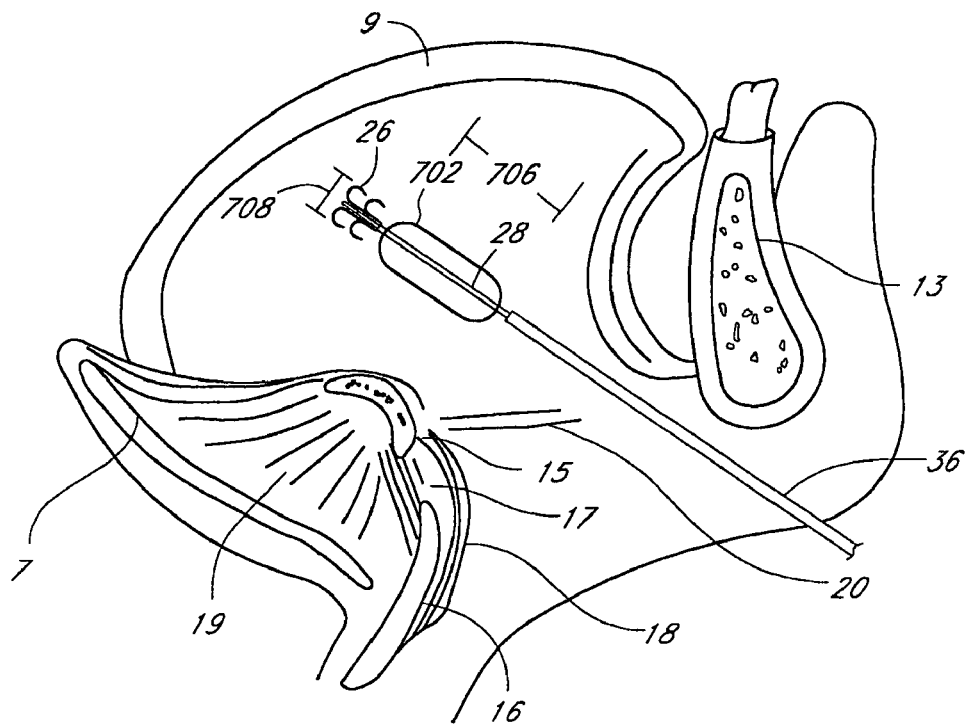
FIGS. 10A and 10B are schematic sagittal views of another embodiment of the invention illustrating tongue remodeling.
Figure 10B:
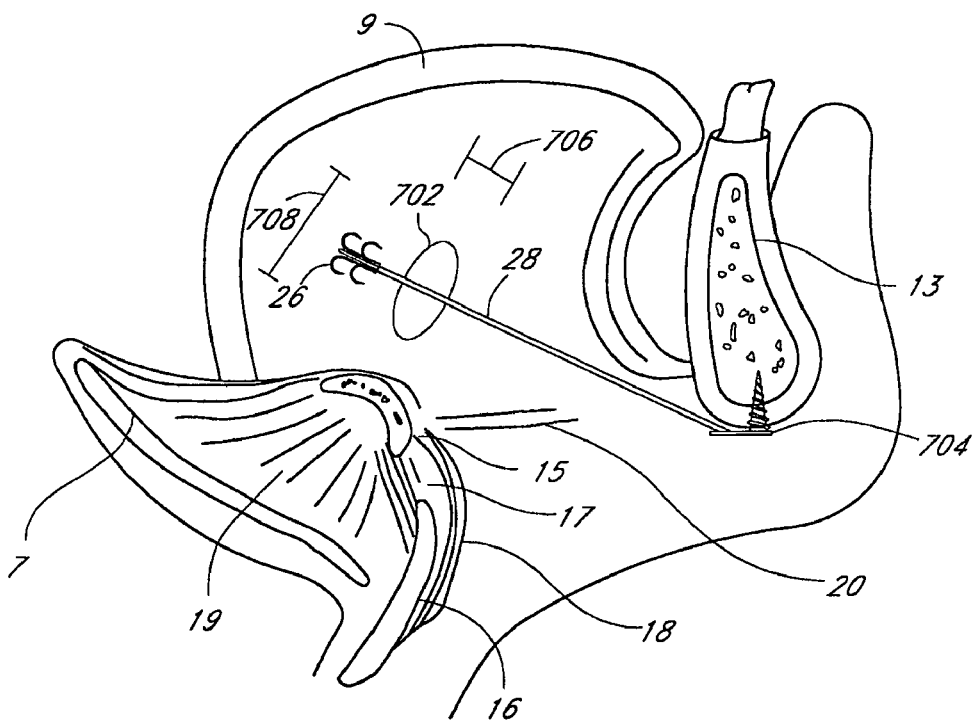

FIGS. 10A and 10B illustrate one embodiment of the invention wherein the cavity 702 formed in the tongue 9 need not be spherical. The cavities formed in the tongue may be any of a variety of three-dimensional shapes and one cavity need not be identical to other cavities in terms of size or shape. Furthermore, the combination of using volumetric tongue reduction with tongue anchoring need not result in a collapse or volume reduction of the cavity to achieve its effect. For example, the oblong cavity 702 depicted in FIG. 10A may reduce its dimension. 706 along the insertion pathway, but may increase its dimension along an axis 708 transverse to the insertion pathway upon deformation by the tethered tissue anchor 26, as shown in FIG. 10B, thereby maintaining or even increasing its volume in some cases while still relieving or reducing airway obstruction.

Figure 11A:
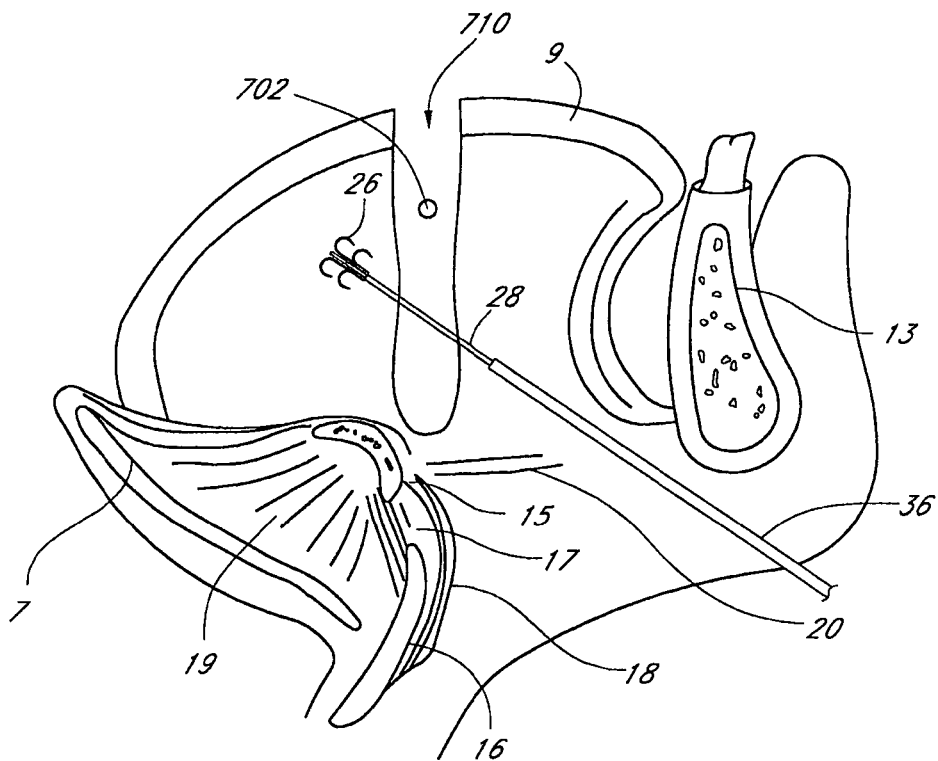
FIGS. 11A and 11B are schematic sagittal views of another embodiment of the invention illustrating tongue remodeling.
Figure 11B:
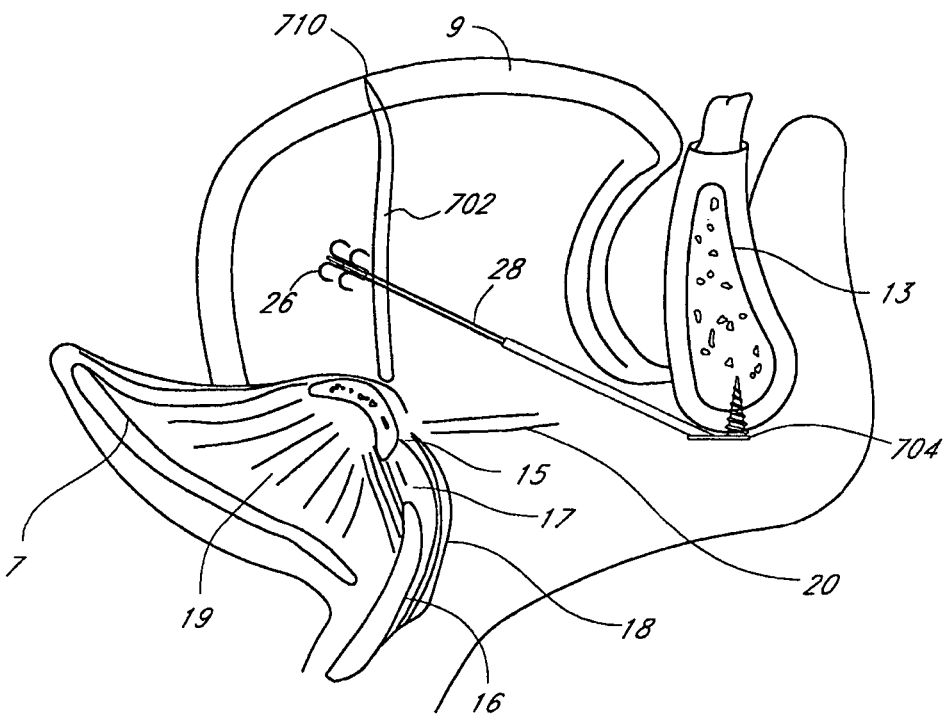

FIGS. 11A and 11B illustrate one embodiment of the invention whereby an exposed cavity 702 is collapsed using a tethered anchor 26. The opening 710 of the cavity 710 to the oropharynx 2 may be closed by a separate suture or may be sufficiently collapsed by the tethered tissue anchor 26 and therefore not require additional closure methods.

Figure 12A:
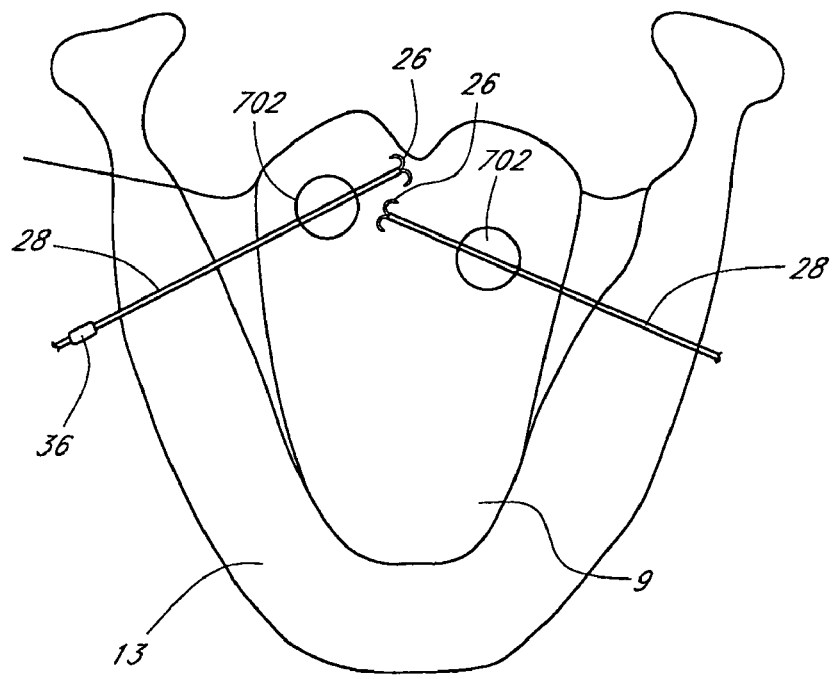
FIGS. 12A and 12B are schematic sagittal views of another embodiment of the invention illustrating tongue remodeling.
Figure 12B:
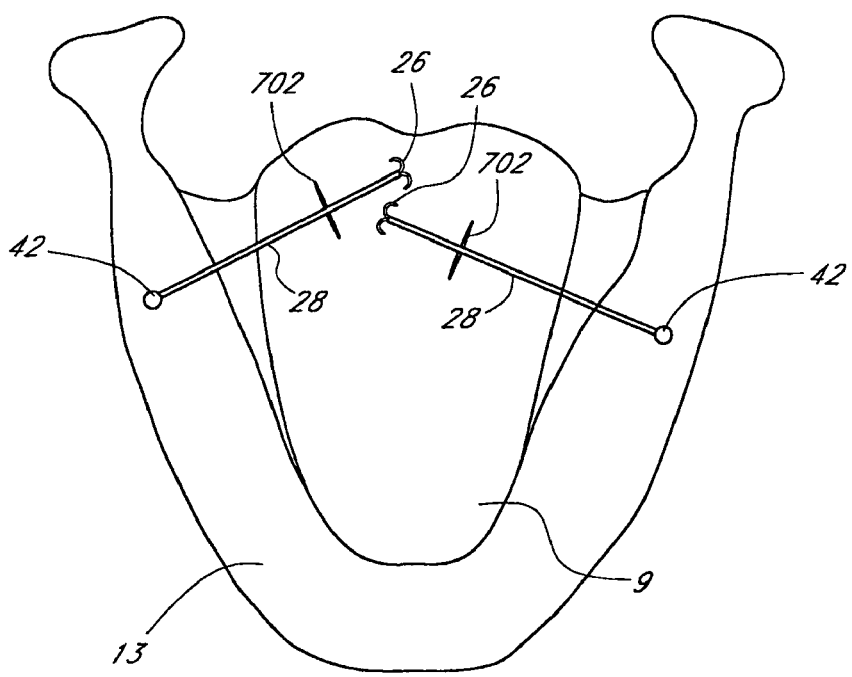

Although the preceding embodiments depict the implantation of the tethered tissue anchor in a general posterior-superior direction from the anterior mandible, other angles and orientations of the tethered tissue anchor and/or tongue cavities are possible. For example, FIGS. 12A and 12B illustrate one embodiment of the invention having multiple anchors 26 where each is inserted from the lateral mandible 13 to collapse separate cavities 702. The separate anchors 26 are attached to opposite sections of the mandible 13 using separate securing assemblies 42, but in other embodiments may be to the same section or even the same securing assembly 42. The anchors 26 do not need to be implanted symmetrically in the tongue or anchored symmetrically on the mandible 13.

Figure 13A:
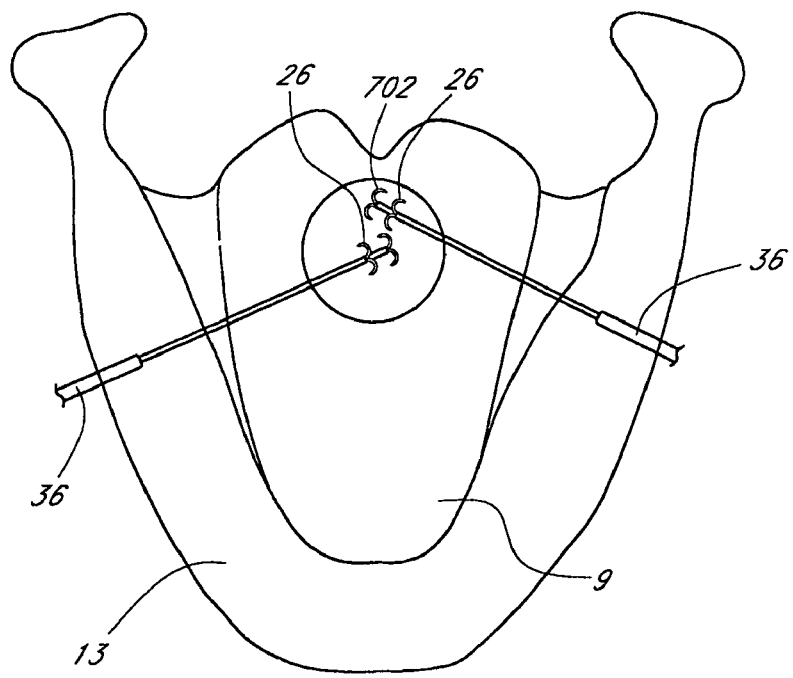
FIGS. 13A and 13B are schematic sagittal views of another embodiment of the invention illustrating tongue remodeling.
Figure 13B:
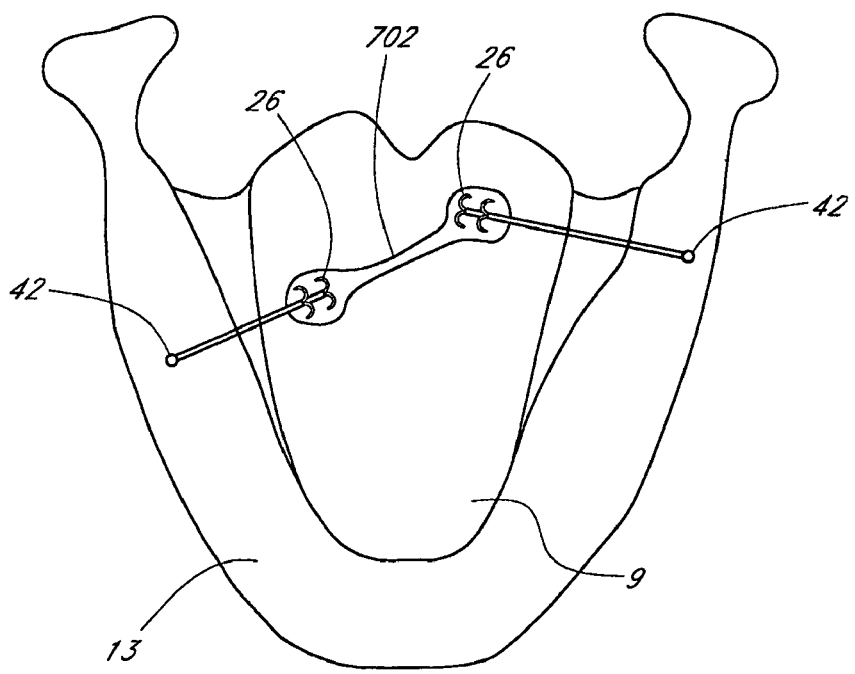

In another example, FIGS. 13A and 13B depict one embodiment of the invention using multiple tethered tissue anchors 26 having separate securing assemblies 42 and each is inserted from the lateral mandible 13 to collapse the same cavity 702. FIGS. 13A and 13B also illustrate how a tethered tissue anchor 26 may be implanted inside a pre-formed cavity 702 of the tongue 9 and still deform it to reduce tongue volume.

Additional Glossoplasty and Tongue-Reshaping Implants

FIGS. 16A-C illustrate top views of embodiments of tongue-reshaping devices 802. The shaded area 800 of FIG. 16A represents one preferred area in which the tongue-reshaping device 802 may be advantageously placed at the base of the tongue 9. The tongue-reshaping device 802 may comprise one or more implants 802. The implants 802 may be made of silicone, a polymer, a collagen-based material, or other material as described elsewhere in the application. In one embodiment, shown in FIG. 16B, implants 802 are placed vertically down the base of the tongue 9 to create a substantially U-shaped concave depression. Suppose the tongue 9 falls back into the posterior oropharynx, as is often the case for a sleeping patient with obstructive sleep apnea. The concave configuration of the implant 802 in the base of the tongue will prevent airway obstruction as shown, improving airflow and therefore oxygenation. In another embodiment, shown in FIG. 16C, a pre-shaped wire 804 may also be implanted within the tongue 9 tissue as another means of creating the substantially U-shaped concave configuration. In other embodiments, the shaped wire 804 may be engaged within the tongue 9 in a first configuration to facilitate placement and then later expanded to a second configuration. In some embodiments, the shaped wire 804 may comprise a shape memory material, such as Nitinol.

FIGS. 16D-16F show other various embodiments of tongue-reshaping devices that are surface area-increasing elements 805 for connecting to tether loops 808 at the tongue 9 base. Surface-area increasing elements 806, 810, 812 illustrated in FIGS. 16D-16F are some non-limiting examples of structures that can be placed at 805 for connecting to tether loops, according to some embodiments of the invention. FIG. 16D illustrates a surface area-increasing element that comprises a balloon 806. The balloon 806 may optionally have a porous portion or covering to facilitate tissue ingrowth. FIG. 16E depicts a substantially tubular structure 810. The tubular structure 810 is expandable in situ from a first configuration to at least a second configuration to increase surface area at the tongue base. FIG. 16F depicts a surface area-increasing element 812 that includes an expanding structure that may further comprise an attached membrane 813. The membrane 813 may be either porous or solid. The membrane 813 may also be deployed in a radially contracted state and transformed into a radially expanded state after deployment. Surface area-increasing element 813 may also include a wire 804 that can be as described in connection with FIG. 16C.

FIG. 17 illustrates another embodiment of a tongue-reshaping device that comprises a chronically adjustable implant 814. A chronically adjustable implant 814 can be a balloon in some embodiments. The implant 814 is preferably installed within the base of the tongue 9. The implant 814 is also configured to be connected to a pump 816 that may add or remove a filler material from the implant 814 in order to adjust the implant's shape. The implant 814 can be chronically adjusted to a greater or lesser size by adding or removing filler material, either at implantation or anytime postimplantation.

FIG. 18 illustrates another embodiment of a tongue-reshaping device comprising a plurality of tissue anchors 816, 820 connected therebetween by an elastic member 818. The elastic member 818 may be a spring, bungee-type cord, and the like. After deployment of the distal tissue anchor 816, the proximal anchor 820 may be drawn away from the distal anchor 816 to extend the elastic member 818 to a length greater than the length of the elastic member 818 at rest. The proximal anchor 820 is then deployed. The extended elastic member 818 will thus place the two tissue anchors 816, 820 in compression.

Figure 19A:
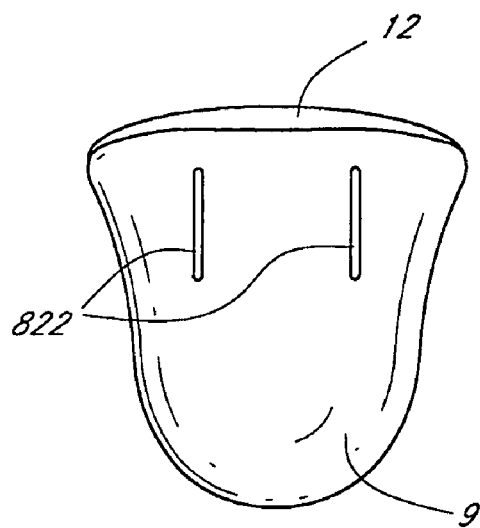
FIGS. 19A-C illustrate an embodiment of a tongue suspension device. In this embodiment, one or more implants are placed within a tissue.
Figure 19B:
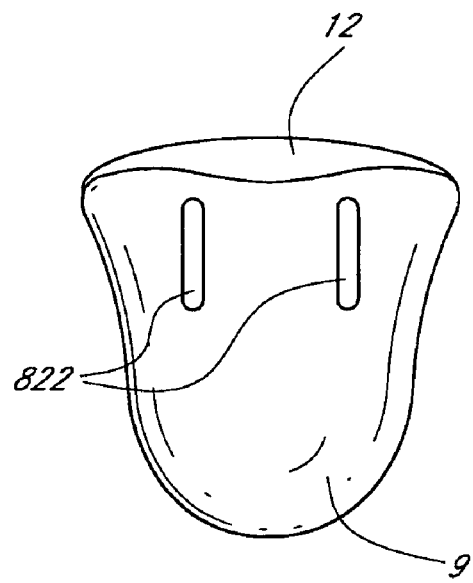
Figure 19C:
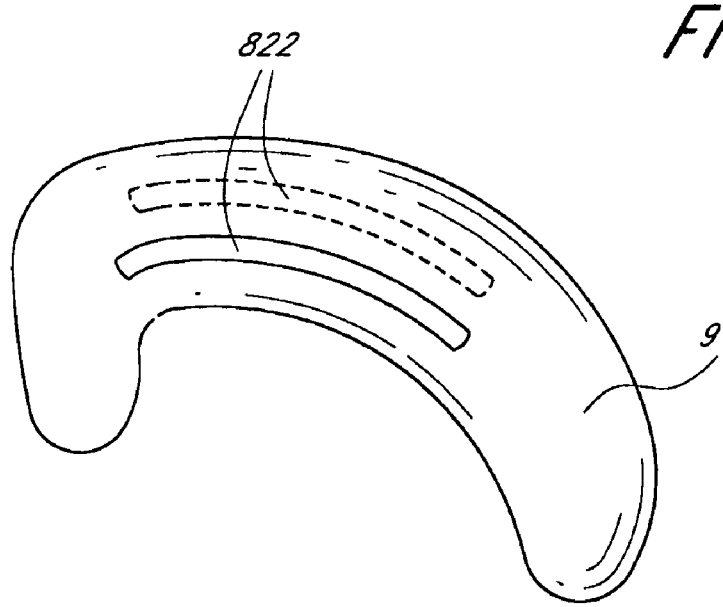

FIGS. 19A-C illustrate an embodiment of a tongue suspension device. In this embodiment, one or more implants are placed within a tissue. Preferably, the implant is a balloon 822 and the tissue is the posterior tongue 9. In the preferred embodiment shown, balloons 822 are offset from the midline of the tongue. The balloons 822 are preferably inserted in a deflated state, as shown schematically in FIG. 19A, and inflated with a filler material, such as saline. The inflated balloons 822, shown schematically in FIG. 19B, will alter the configuration of the tongue 9 and advantageously prevent the tongue 9 from collapsing against the posterior pharyngeal wall 12. FIG. 19C shows a side view of FIG. 19B. In some embodiments, the balloons 822 described in connection with FIGS. 19A and 19B above are preferably long and cylindrical in shape as shown. The balloons 822 may be deployed through a curved hypotube to follow the curvature of the base of the tongue 9 in the posterior pharynx 12 where airway collapse may be occurring, and inflated as described above to preferably push the tongue 9 away from the posterior pharyngeal wall 12 and thus prevent collapse.

Figure 20A:
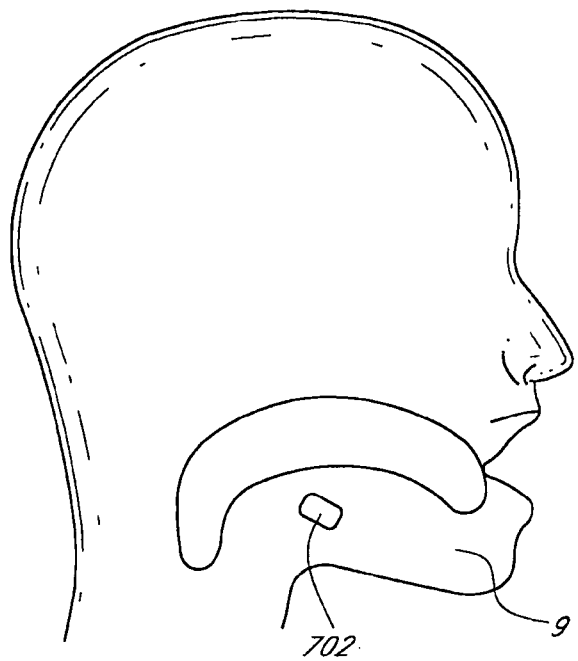
FIGS. 20A-D illustrate schematically methods for removing a volume of tissue.
Figure 20B:
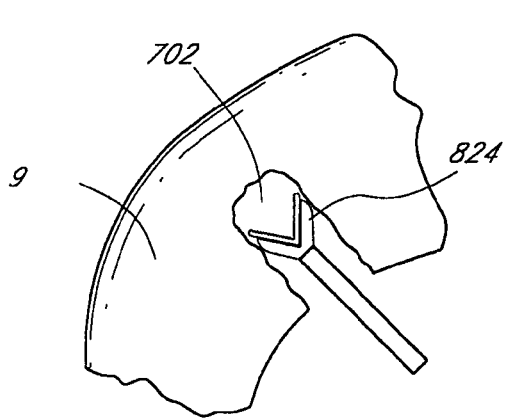
Figure 20C:
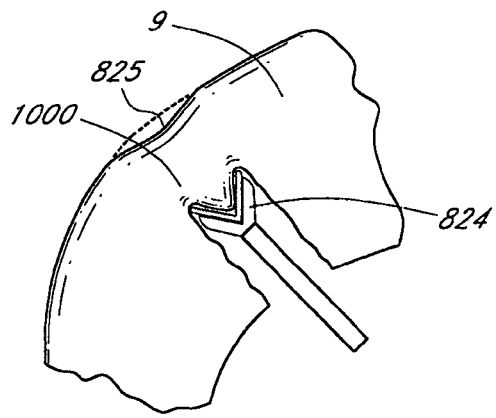
Figure 20D:
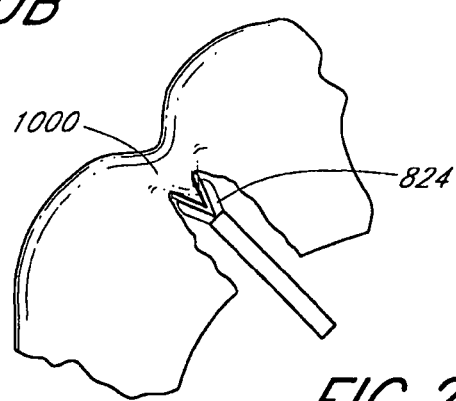

FIGS. 20A-D illustrate schematically methods for removing a volume of tissue, preferably from the tongue 9 (glossoplasty), more preferably from the genioglossus muscle. FIG. 20A is a schematic of a tissue void 702 after removal of tissue. A tissue space or void as referred to herein is most preferably an artificially created space. The tissue may be removed via a scalpel, electrocautery, laser, or other cutting means. Chemical or high-frequency ultrasound ablation may also be used to form spaces in the tongue. After tissue removal, the space 702 created can be closed in order to draw the tissue in a desired direction. Thus, the tongue 9 can be advanced forward when the space 702 is closed by a suture, clip, or the like. In some embodiments, a clipping element 824, shown as a titanium clip, is provided and delivered to the tissue void 702, as shown in FIG. 20B. Engaging the clip 824 with the distal tissue will alter configuration of the distal tongue tissue 1000 and advance the tongue 9 anteriorly (at indentation 825 that is anterior with respect to shown dotted line) as shown in FIG. 20C. Clamping will pull the tongue tissue 1000 toward the clip 824, preferably in an anterior direction. FIG. 20I) illustrates retraction of the posterior tongue 9 upon closure of the clip 824.

Figure 21A:
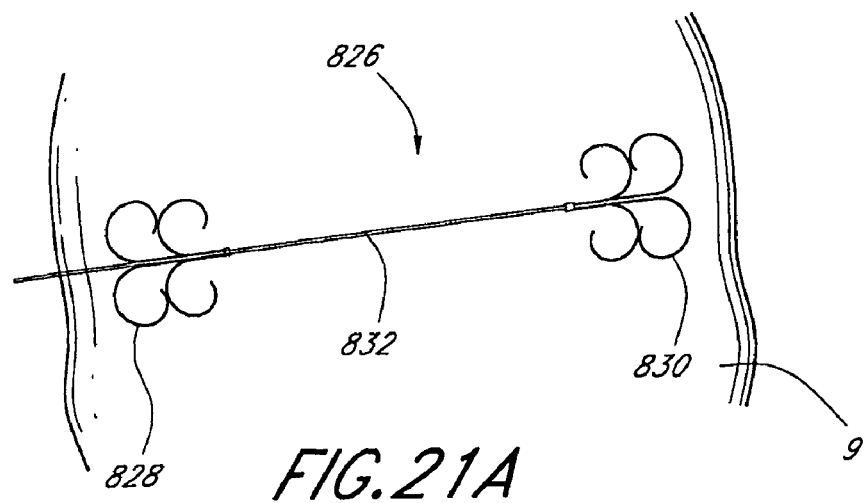
FIGS. 21A-E are schematic diagrams of an embodiment of a double-ended anchoring device that may be implanted within the tongue for tongue remodeling.

FIGS. 21A-E are schematic diagrams of an embodiment of a double-ended anchoring device 826 that may be implanted within the tongue 9 for tongue remodeling. Shown in FIGS. 21A is a first (proximal) anchor 828, and a second (distal anchor) 830 connected by a tether 832 which is preferably fixed to the distal anchor 830 and extends proximally through the proximal anchor 828 as shown. The distal anchor 830 may be as described above in the application, and may comprise a hub. The proximal anchor 828 preferably comprises a hollow core configured to receive and pass a tether 832 therethrough, and a hub on the proximal end. The device is preferably implanted within the genioglossus muscle of the tongue 9, although other locations within the tongue 9 are also envisioned.

A method for deploying the double-ended anchoring device 826 within the tongue 9 and adjusting the tension (and length) of the device 826 is also disclosed. The device 826 is first delivered via a delivery tube, and the distal anchor 830 is preferably deployed out of the tube into the genioglossus muscle. The tube is then retracted a desired distance and the proximal anchor 828 is then deployed.

Figure 21B:
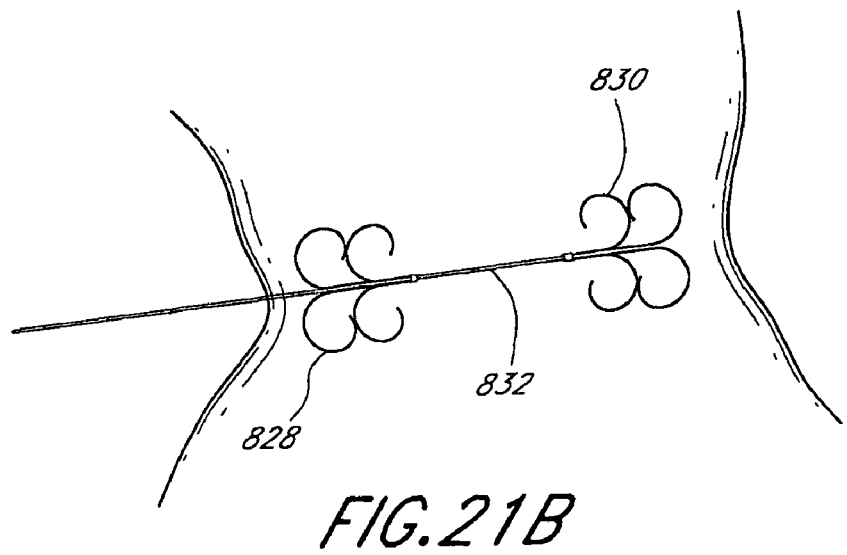
Figure 21C:
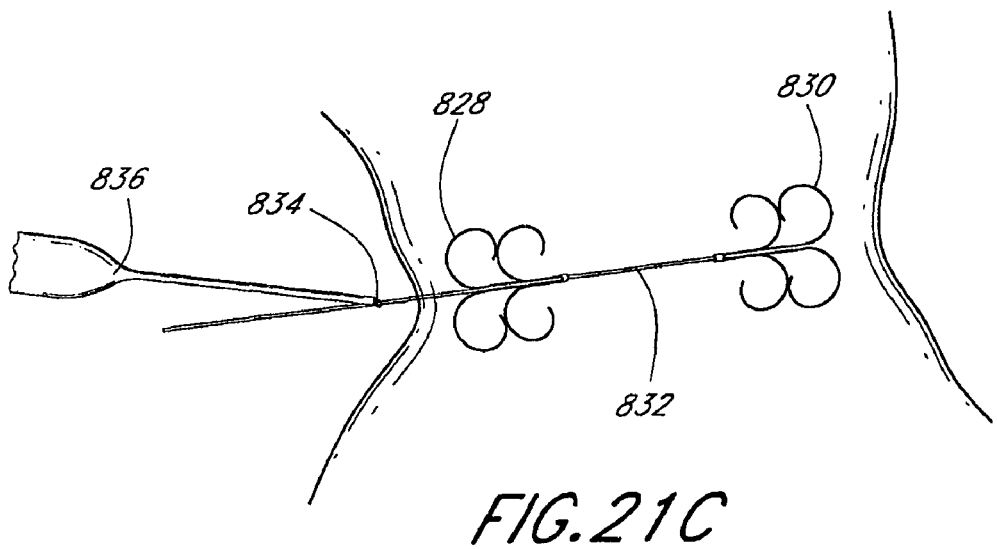
Figure 21D:
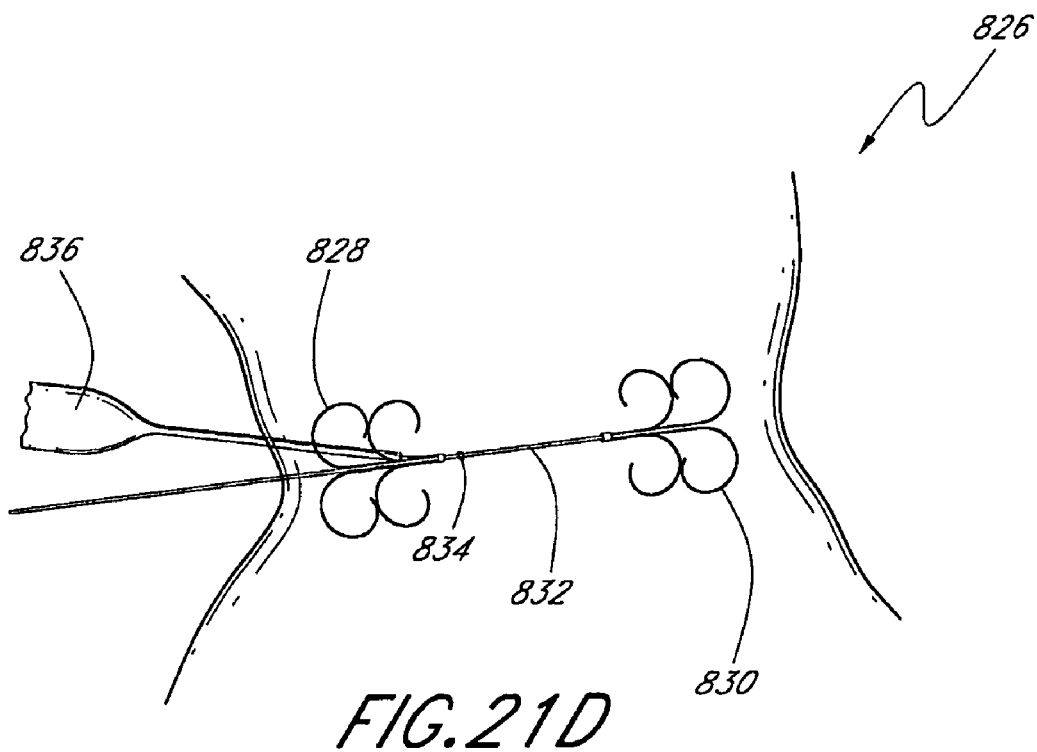
Figure 21E:
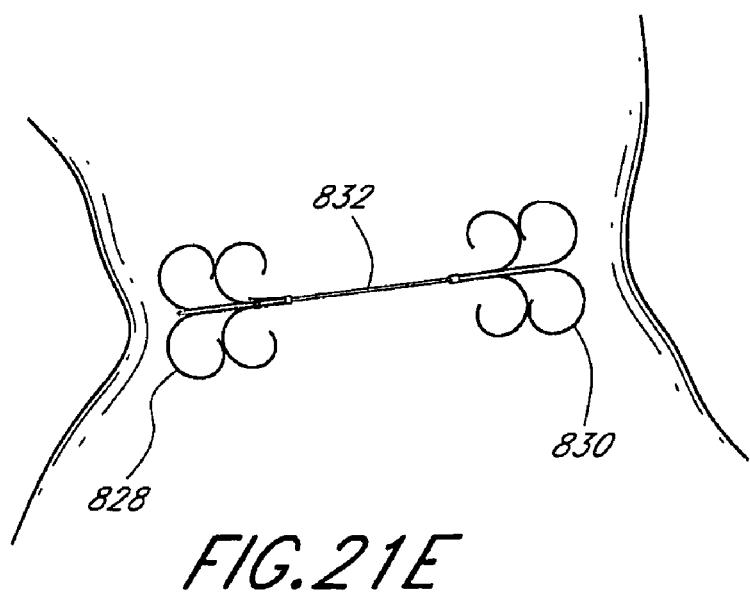

As in FIG. 21B, the tension of the tether 832 is adjusted proximally to the proximal anchor 828. Next, a sliding knot 834 is tied by an operator, and advanced toward the proximal anchor with a knot pusher or clip applier (e.g., a tether clip or ligating clip) as shown in FIG. 21C. Next, the knot 834 is made snug at the hub of the proximal anchor 828, or alternatively, clamped with a tether clip 836 as shown in FIG. 21D. Finally, the tether line 832 is cut with a scalpel or other cutting means just proximal to the proximal anchor 828, as shown in FIG. 21E.

Figure 22A:
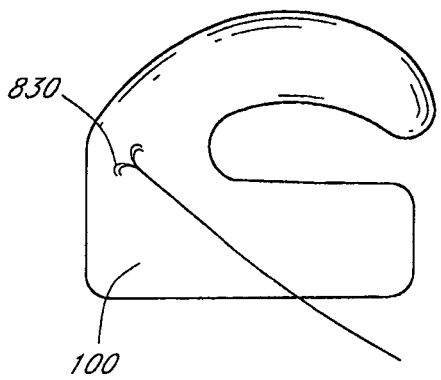
FIGS. 22A-E illustrate a method for deploying a tissue anchoring system, according to another embodiment of the invention.
Figure 22B:
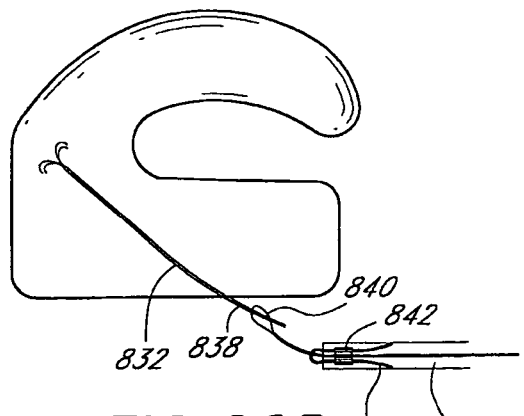
Figure 22C:
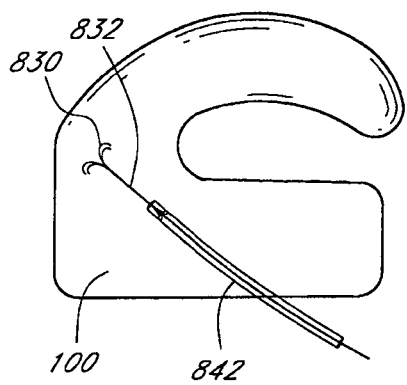
Figure 22D:
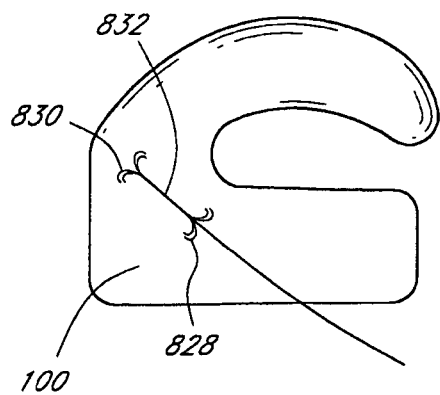
Figure 22E:
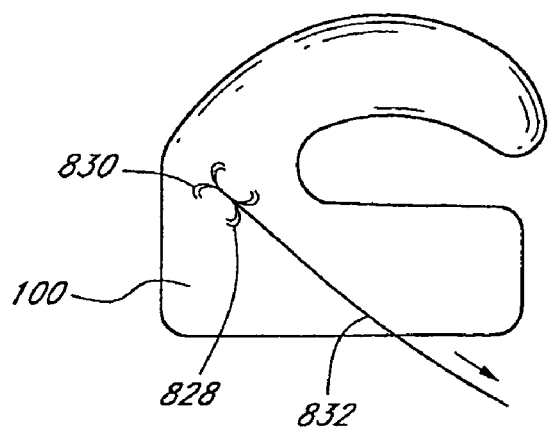

Next, another method for deploying a double-ended anchoring device 826 (such as the device described in connection with FIG. 21) within the tongue 9 is described. First, the distal anchor 830 is engaged within the genioglossus muscle 100 as depicted in the schematic FIG. 22A. Delivery of the distal anchor 830 may be done as described elsewhere in the application, for example, as with FIG. 21 above. Next, a proximal tether end 838 is accessed, such as with a snare 840. The proximal tether end 838 is then loaded through the hollow core of the proximal anchor 828 into a delivery tube 842 as shown in FIGS. 22B-C. The tube 842 is then tracked back over the tether 832 to the desired depth. Next, the proximal anchor 828 is pushed out of the delivery tube 842. Preferably, this is done with no tension on the tether 832 to advantageously achieve maximum tissue tension, as shown in FIG. 22D. The delivery tube 842 may then be removed. Next, the tether 832 is tensioned and the proximal anchor 828 pushed posteriorly to achieve compression of the tongue tissue 9, as shown in FIG. 22E. The tether 832 may then be tied, clipped, or secured to the proximal anchor 828 as described elsewhere in the application.

Figure 23A:
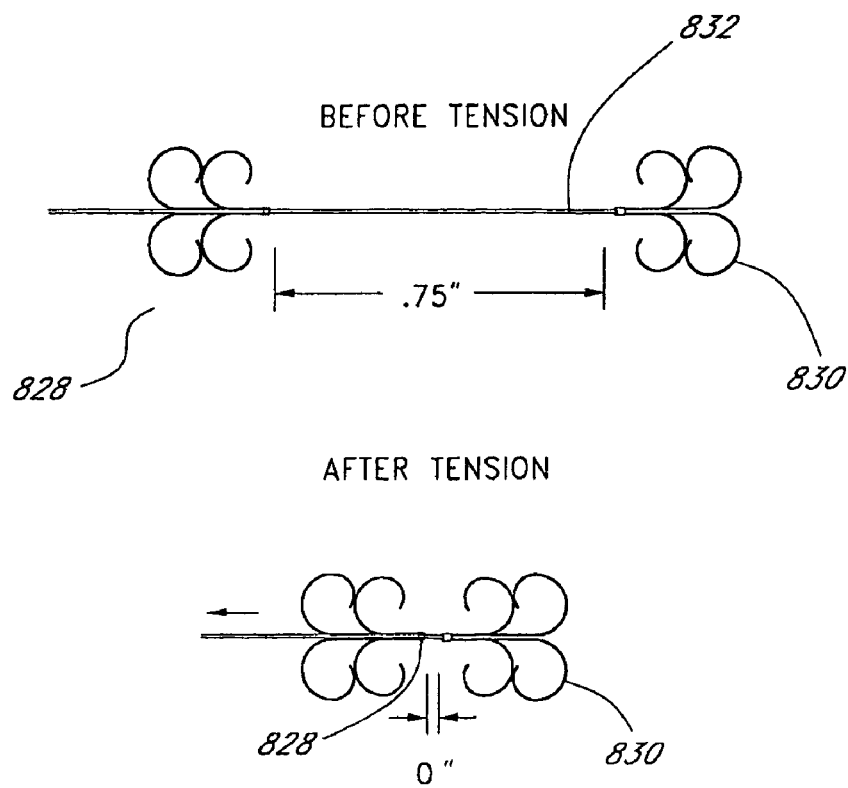
FIG. 23A depicts another embodiment of a double-ended anchoring device.

The method described in association with FIGS. 21-22 above were used to deploy a double-ended anchoring device 826 into a bovine tongue. The two anchors 828, 830 shown in FIG. 23A before tension are about 0.75 inches apart from hub tip to hub tip. After tensioning the tether 832, the proximal anchor hub 828 and distal anchor hub 830 are drawn together as shown. Next, several overhand knots were thrown and pushed down to the proximal anchor 828 until secured. Even though the anchor 828 was about 0.5 to about 0.75 inches below the tissue surface (not shown), the tissue remained easily compressible and the knots were readily pushed down to the anchor 828.

Figure 23B:
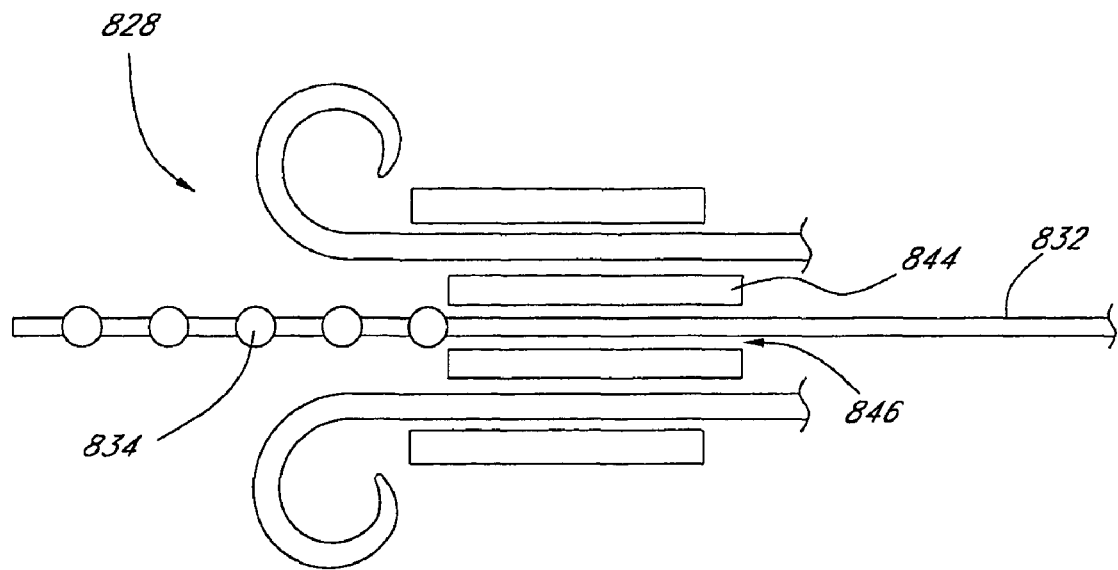
FIG. 23B shows an embodiment of an anchor with a tether locking insert.
Figure 23C:
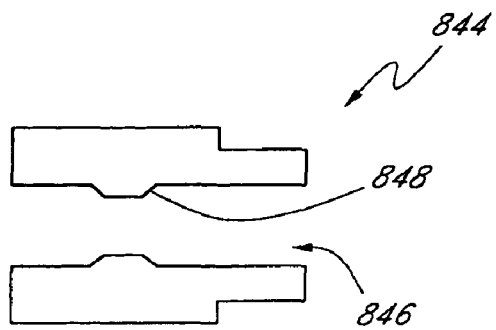
FIGS. 23C-D show embodiments of channel configurations for an anchor with a tether locking insert.
Figure 23D:
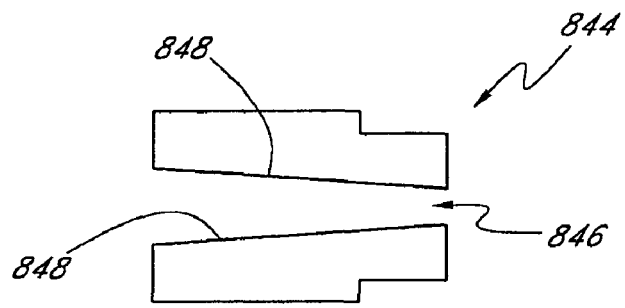

As noted elsewhere in the application, the proximal anchor 828 may be locked to the tether 832 by providing a tether locking insert 844 within the anchor, which is preferably a substantially tubular structure with a channel 846 therein, as shown in FIG. 23B. The tether locking insert 844 is preferably made of titanium, although other metals and non-metallic materials can also be used. As noted, the tether knots 834 most preferably have a larger outside diameter than the inside diameter of the channel 846 of the tether locking insert 844 in order to prevent squeezing or slippage of the tether 832 into the inside diameter of the insert 844. In other embodiments, the tether locking insert 844 may comprise a frictional surface to further reduce slippage of the knot 834. FIGS. 23C-D show other non-limiting examples of usable channel configurations. FIG. 23C illustrates an embodiment where the protruding surface 848 is a chamfer. FIG. 23D shows an embodiment where the internal channel 846 is a gradual taper 848.

Figure 24A:
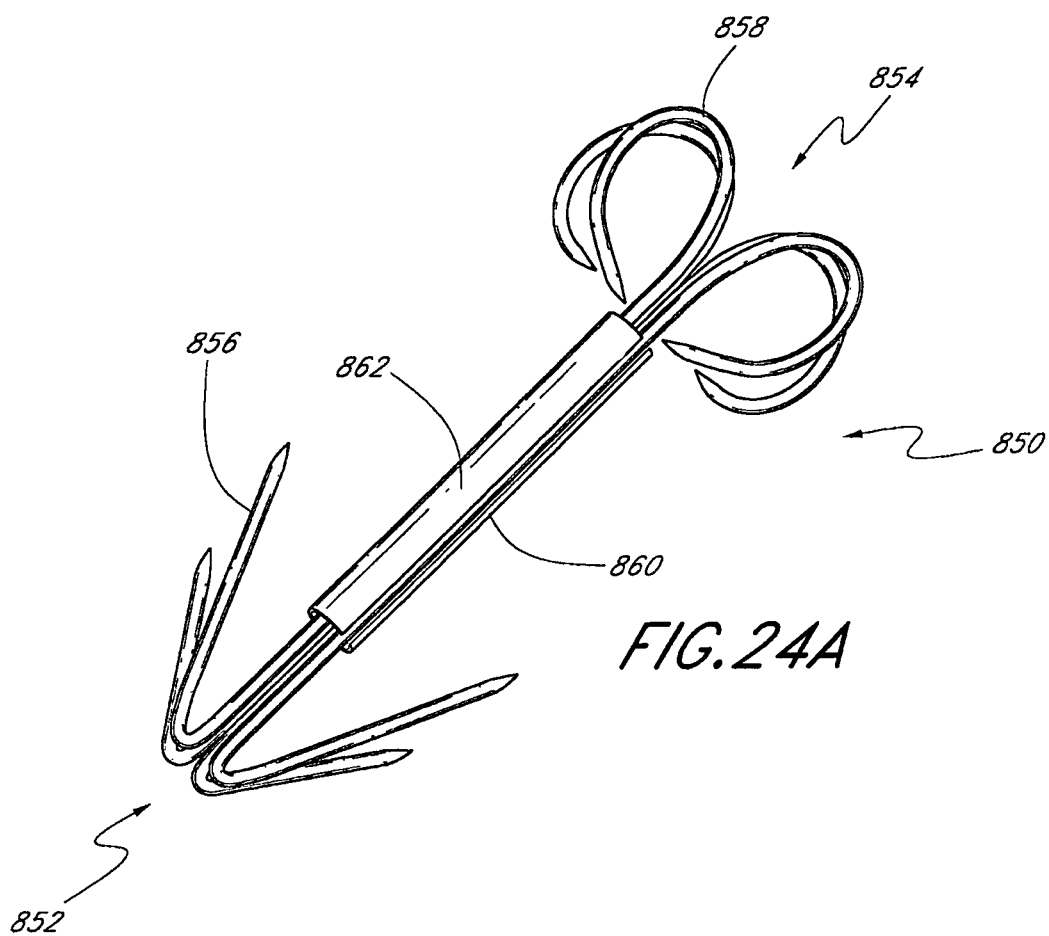
FIGS. 24A-D show various views of an implant that can be used to compressed tissue together in a localized region.

FIGS. 24A-D show an embodiment of an implant 850 that can be utilized to compress tissue together in a localized region, for example, the genioglossus muscle 100, that will promote suspension of the tongue 9. FIG. 24A shows a perspective view of an embodiment of an implant 850 in a double-ended grappling hook configuration. The implant 850 shown comprises a proximal hook portion 852 with a plurality of hooks 856, a distal hook portion 854 with a plurality of hooks 858, and an elongate body 860 connecting the proximal 852 and distal portions 854. The elongate body 860 may comprise a sleeve 862 as shown. While the distal hooks 858 are depicted as more rounded than the proximal hooks 856, a wide variety of other hook configurations as described elsewhere in the application can readily be used as well.

Figure 24B:
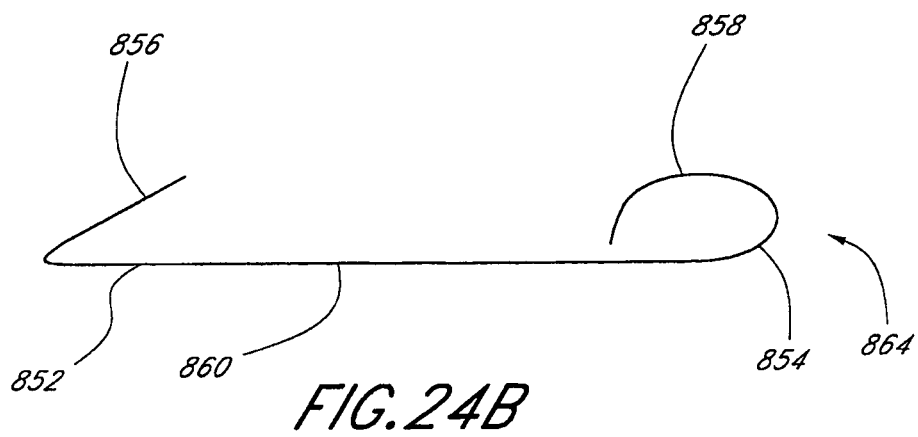
Figure 24C:
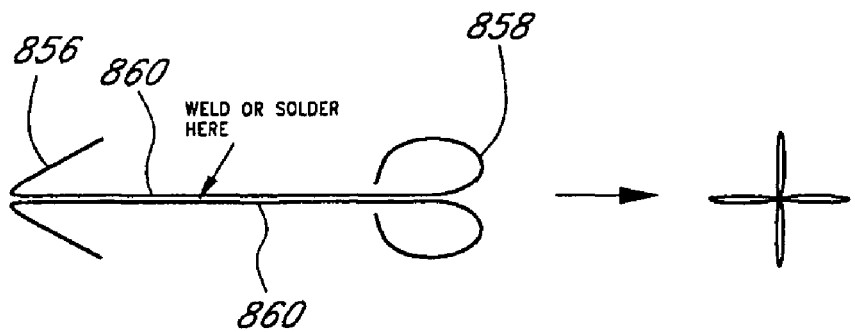
Figure 24D:
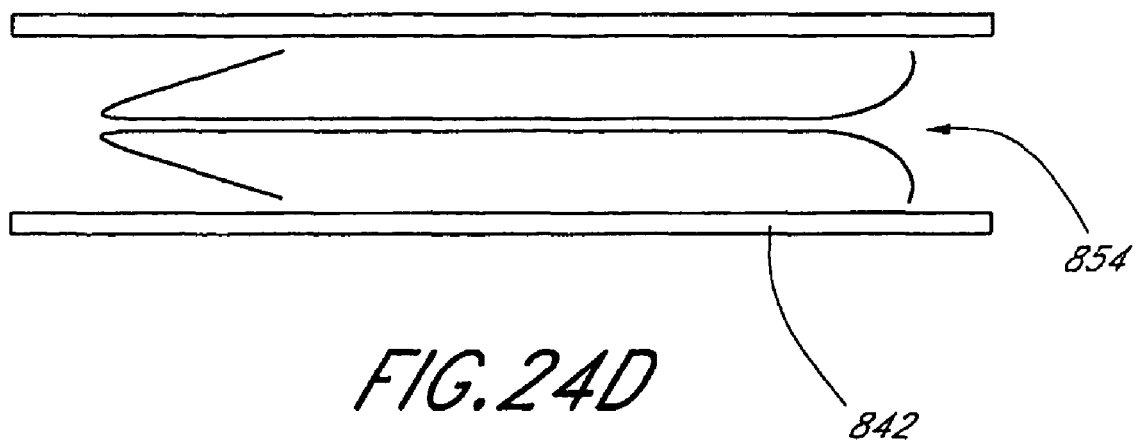
Figure 25A:
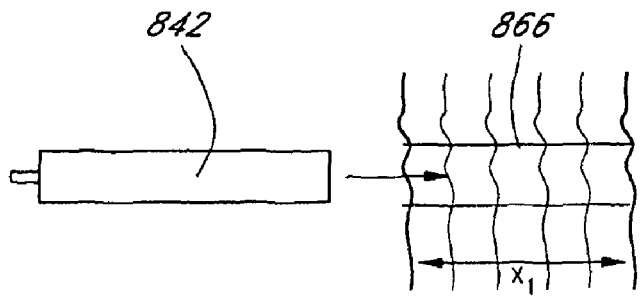
FIGS. 25A-E illustrate a method of deploying a double-ended grappling hook anchoring device into a tissue.
Figure 25B:
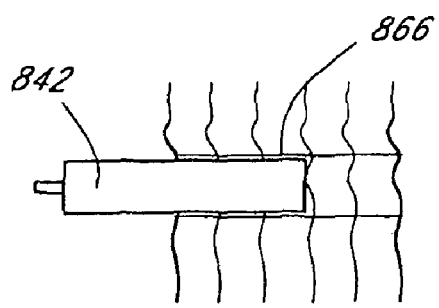
Figure 25C:
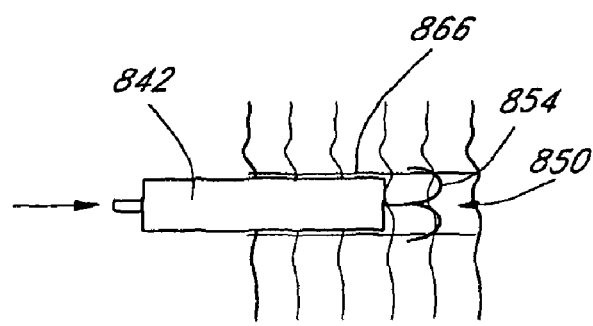
Figure 25D:
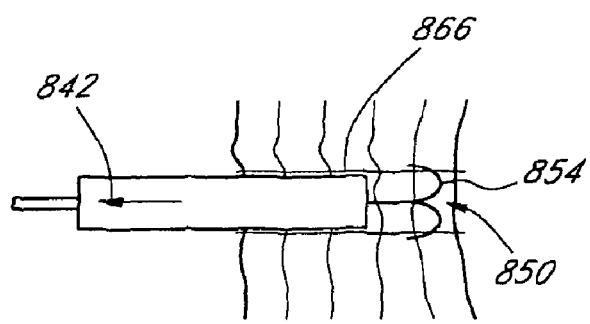
Figure 25E:
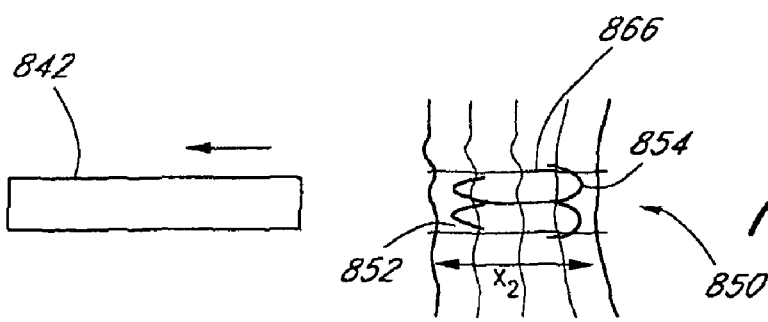

A method of assembling a double-ended grappling hook anchoring device 850 will now be described, in conjunction with FIGS. 24B-D. First, a hook element 864 with a proximal 852 and distal end 854, and an elongate body portion 860 therebetween is provided. The proximal 852 and distal ends 854 both comprise hooks 856, 858 as shown in FIG. 24B. Next, the elongate body portions 860 of two or more hook elements 864 may be soldered, welded, or attached together by other means as known in the art, as shown in FIG. 24C. In one preferred embodiment, four hook elements 864 are attached together at substantially right angles as shown. However, two, three, five, six, or more hook elements 864 may be attached together in other embodiments to form a double-ended grappling hook anchoring device 854. The anchoring device 854 may then be loaded inside a delivery element 842, such as a hypotube, as shown in FIG. 24D.

FIG. 25 illustrates a method of deploying a double-ended grappling hook anchoring device 850 into a tissue, such as the device shown in FIGS. 24A-D. First, an introducer/trocar (not shown) is delivered into the desired tissue plane, creating a track 866. The delivery element 842 including the device 850 is delivered along the track 866 created by the introducer/trocar, as shown schematically in FIG. 25A. Distance $X_1$ represents a distance between two points of the tissue. FIG. 25B shows the delivery element 842 at a desired depth within the tissue. Next, the device 850 is pushed out of delivery tube 842 sufficiently such that the distal anchor 854 captures tissue, as shown in FIG. 25C. The delivery element 842 and distal anchor 854 are then retracted proximally, as depicted in FIG. 25D (friction between the anchor 854 and the hypotube 842 will provide traction on the tissue or a releasable connector may be required to provide adequate compression of the tissue) and then the proximal anchor 852 will then be deployed. Next, the delivery element 842 is fully removed while the device 850 is tensioned, as in FIG. 25E. Because the device 850 is deployed under tension, the tissue is compressed. This is shown by Distance $X_2$, the distance between two points after placement of the anchoring device 850. Distance $X_2$ shown is shorter than Distance $X_1$.

FIGS. 26-27 illustrate embodiments of a double-ended grappling hook anchoring device 868 comprising various adjustment elements. FIG. 26 depicts an embodiment of a double-ended grappling hook device 868 similar to the embodiment described in connection with FIG. 24, except that the elongated body portion comprises an adjustment element 870. The adjustment element shown is a ratchet 870. The ratchet 870 may be a one way ratchet that can include a disengagement tool to facilitate removal of the anchoring device 868 when needed. In other embodiments, the adjustment element 870 may comprise a two-way ratchet. In still other embodiments, the adjustment element 870 may be a zip tie, and the like. The proximal anchor 852 shown includes a hub 872 configured to engage the ratchet. Applying a force on the proximal anchor 852 in the direction of the distal anchor 854 will facilitate ratcheting and compression of the tongue tissue.

FIG. 27 shows another embodiment of an anchoring device 874 where the adjustment element 870 is a pulley. The proximal 852 and distal 854 anchors may be generally as described elsewhere in the application. The pulley 870 includes a friction knot or one-way lock, and engages a tether 870. The pulley also includes a cleat or friction feature (not shown) to lock the tether once the device is adjusted to compress tissue at a desired location.

FIG. 28 illustrates another embodiment of a tongue-reshaping device 874 comprising a plurality of tissue anchors 852, 854 connected therebetween by an elastic member 876. The elastic member 876 may be a spring, bungee-type cord, and the like. After deployment of the distal tissue anchor 854, the proximal anchor 852 may be drawn away from the distal anchor 854 to extend the elastic member 876 to a length greater than the length of the elastic member 876 at rest. The proximal anchor 852 is then deployed. The extended elastic member 876 will thus place the two tissue anchors 852, 854 in compression.

FIG. 29 depicts an embodiment of an adjustment mechanism 886 with a plurality of tissue anchors 852, 854 connected therebetween by a tether 878. A distal anchor 854 is preferably attached in the tongue base, at the tip of the genioglossus muscle. The distal anchor 854 may have a plurality of hook elements 880, 882 as shown. A proximal anchor 852 has a central lumen extending through the anchor. The proximal anchor 852 may be anchored in tissue of the tongue as described above. The lumen is configured to receive the tether 878. The proximal anchor 852 may further include an adjustment mechanism 884, such as a gripping collar 884 at the proximal end of the anchor 852 to hold the tether 878 position under tension once the desired tension has been established. In other embodiments, a spooling mechanism, such as those described elsewhere in the application may be substituted for a gripping collar 884 to allow for tether 878 adjustment. Other non-limiting suitable adjustment mechanisms 884 are described, for example, in connection with FIGS. 37-39.

FIG. 30 depicts an embodiment of an adjustment mechanism 888 that is similar to the embodiment shown in FIG. 29. In this embodiment, the proximal tissue anchor 852 (which may be implanted in relative proximity to the mandible) is larger in size than the distal tissue anchor 854. A relatively small distal tissue anchor 854 relative to a proximal tissue anchor 852 may be advantageous in optimizing patient comfort as a distal tissue anchor 854 is preferably implanted in a relatively superficial layer with respect to the surface of the tongue. In contrast, a larger proximal anchor 852, which is preferably implanted in a relatively deeper layer with respect to the surface of the tongue, is less likely to cause patient discomfort.

FIGS. 31A-F illustrate various embodiments of adjustment mechanisms that may be used in conjunction with a tongue remodeling system that is not secured to a bony structure. FIG. 31A illustrates a tongue remodeling system 890 with a plurality of tissue anchors 852, 854 connected therebetween by a tether 892. The tether 892 shown comprises a plurality of beads 894. The beads 894 may be a variety of other shapes, and need not be substantially annular as shown. In other embodiments, the tether 892 shown may comprise a plurality of knots. An adjustment mechanism may comprise a clamping element (not shown in FIG. 31A) that may be attached, preferably proximally to the proximal tissue anchor 852. FIG. 31B illustrates an embodiment of a clamping element 894 that further comprises a spring-loaded slider 896. Actuating the slider 896 in an appropriate direction will open or close a lumen 898 (that is configured to receive the beaded tether) 892 on the clamping element 894 and facilitate adjustment of the beaded tether 892. FIG. 31C is another embodiment of a clamping element 900 similar to that shown in FIG. 31B, except that the actuator is a spring-loaded clip 902.

FIGS. 31D-E illustrate variations of a lumen 898 such as described in connection with FIGS. 31B-C to receive a tether, such as one having beads. The lumen may be formed from an inner tube 906 (shown in FIG. 31E) and outer tube 904 (shown in FIG. 31D). The inner 906 and outer tubes 904 each further include an eccentricity plate 910, 908. The eccentricity plates 910, 908 have a substantially annular outer rim and are configured to fit at an end of the inner 906 and outer tubes 904, the plate of the inner tube 906 positioned adjacent to the plate of the outer tube 904. The eccentricity plates 910, 908 also have an aperture preferably displaced from the center of the plate as shown. FIG. 31F illustrates that turning the inner tube 906 in an appropriate direction will result in a "Venn-diagram" like overlap of the eccentricity plates 910, 908 and decrease the overall aperture size of the lumen 898 and clamping the beaded tether. A skilled artisan will readily appreciate that the adjustment mechanisms of FIGS. 31B-F can be readily adapted to function in conjunction with a bone anchor as well.

FIGS. 32A-B illustrate an embodiment of an adjustment mechanism 912 that comprise a spool 914. The spool 914 shown in FIG. 32A has a long distal nose portion 916 as shown that can abut a tissue anchor hub 918. While the spool 914 may be attached to a bony or other securing structure, it is preferably free-floating. FIG. 32B is an embodiment of an adjustment mechanism 920 similar to that shown in FIG. 32A except the spool 914 may adjust the tension and/or length of a tether axially by an axial adjusting element 924.

FIG. 32C illustrates another embodiment of an adjustment mechanism 924 operably connected to an anchor 922. The adjustment mechanism 924 comprises an elongate element 926 with a threaded channel configured to receive a threaded screw 928. The threaded screw 928 comprises a central lumen in which a tether 930 may pass therethrough. Rotating the screw 928 in an appropriate direction may facilitate trapping of the tether 930 within the elongate element 926, thus serving as a locking, tension or length-adjusting mechanism for the tether 930.

FIGS. 33A-C show another embodiment of an adjustment mechanism that may be engaged within tissue, such as muscle fascia. FIG. 33A is a schematic illustrating a beaded tether 892 connected to an adjusting plate 932 embedded within a tissue plane 934. FIG. 33B shows a front view of the adjusting plate 932. The adjusting plate 932 comprises an aperture 936 configured to receive a beaded tether 892. The plate 932 also includes an actuating element 938 (e.g., a squeezable portion as shown) that will facilitate release of a bead 894 on the beaded tether 892. The adjusting plate 932 may optionally include tether holes 940 to facilitate attachment of the adjusting plate 932 to tissue. FIG. 33C shows a side view of the adjusting plate 932 shown in FIG. 33B. The adjusting plate 932 may further include spikes or barbs 942 as shown to stabilize the adjusting plate 932 to tissue.

Figure 34:
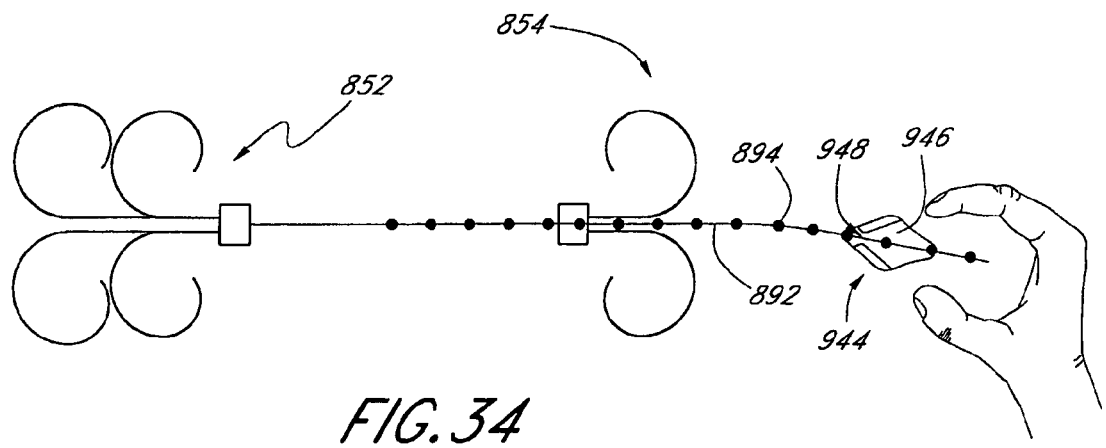
FIGS. 34-35 depict embodiments of an adjustment mechanism that may be adjusted with mechanical pressure.

FIG. 34 illustrates yet another embodiment of an adjustment mechanism 944 that has a luminal portion 946 that decreases in diameter to a narrow apex point 948 before increasing in diameter. A beaded tether 892, and plurality of anchors 852, 854 is also shown, described in more detail elsewhere in the application. The narrow apex portion 948 has a cross-section that is smaller than that of a bead 894. In order for tension on the beaded tether 892 to be adjusted, the beads 894 need to overcome the small cross-section of the narrow apex portion 948 within the adjustment mechanism 944. This may be accomplished by squeezing the adjustment element 944 in a first direction (e.g., manually with a thumb and forefinger) while applying countertraction on the beaded tether 892 in a second direction generally opposite to the first direction.

Figure 35:
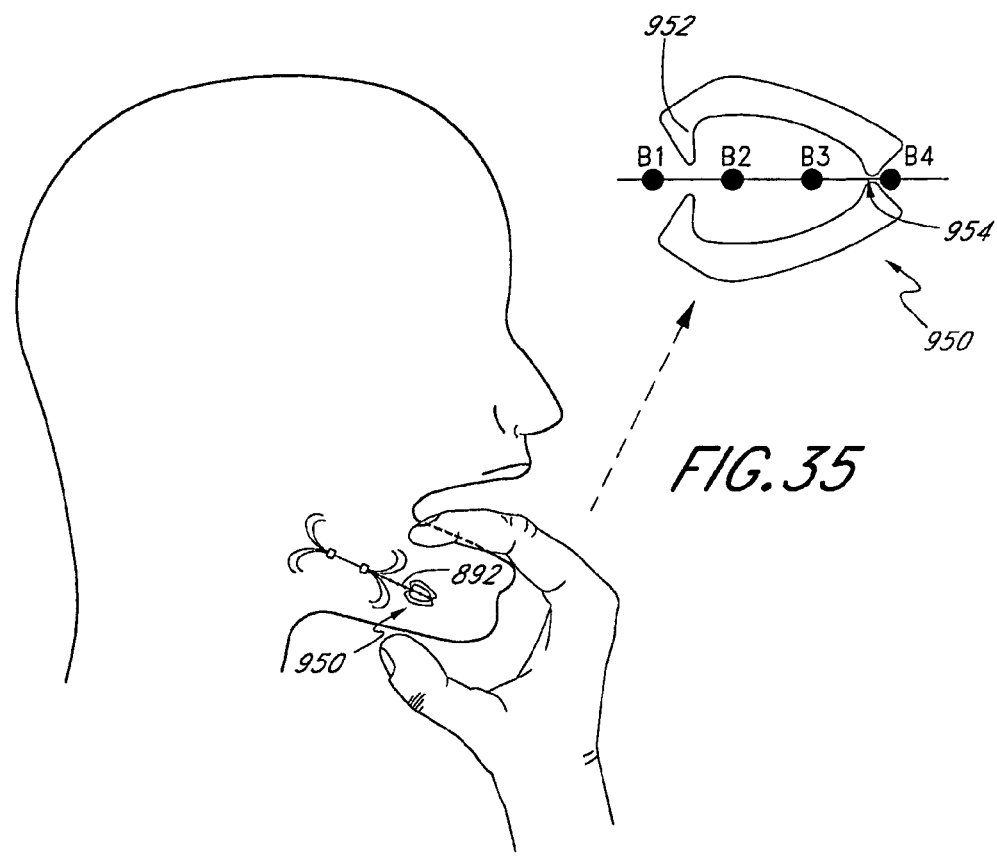

FIG. 35 illustrates an embodiment of an adjustment mechanism 950 similar to that described in connection with FIG. 34. In this embodiment, the adjustment mechanism 950 has a proximal portion 952 and a distal portion 954 and is configured to receive a tether 892, which is shown as a beaded tether in FIG. 35. The mechanism 950 may advantageously be adjusted transdermally, obviating the need for an incision post-implantation. Squeezing the adjustment element 950 externally will cause the jaw-like elongated portions 952 of the adjustment element 950 to elongate further and "trap" a bead (labeled B1) that is initially outside the adjustment mechanism 950 within the adjustment mechanism 950, while another bead (labeled B3) that is within the adjustment mechanism will move outside of the adjustment mechanism 950. The narrow distal-outlet portion 954 of the adjustment mechanism 950 will prevent the bead (B3) from re-entering the adjustment mechanism 950. Interaction of the beads B1, B2, B3, B4 with the adjustment mechanism 950 as described above will thus tension the tether 892.

Figure 36:
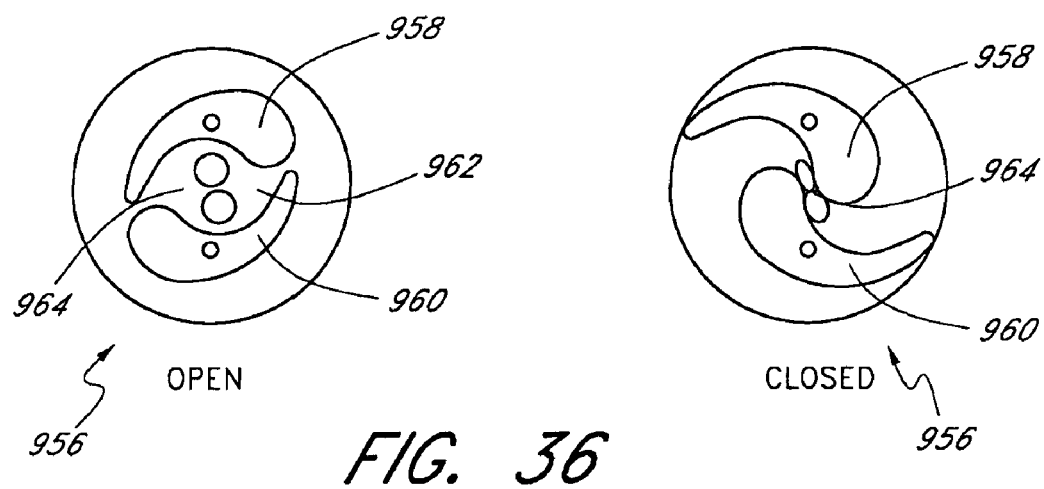
FIG. 36 is a vertical sectional schematic view of an adjustment mechanism comprising a cam lock, according to some embodiments of the invention.

FIG. 36 illustrates an embodiment of a vertical sectional schematic view of an adjustment mechanism that comprises a cam lock 956. The cam lock 956 may be joined with a section of an anchor. In other embodiments, the cam lock 956 may comprise a free-floating intermediate adjustment mechanism. The cam lock 956 includes two moving plates 958, 960 (cams) shaped such that the central inside diameter formed in a space 962 between the plates 958, 960 is open in a first configuration and closed (or at least decreased) in a second configuration. The space 962 is configured to receive a tether 964. One of ordinary skill in the art will appreciate that the length of the tether 964 can be readily adjusted by opening the cam lock 956.

Figure 37A:
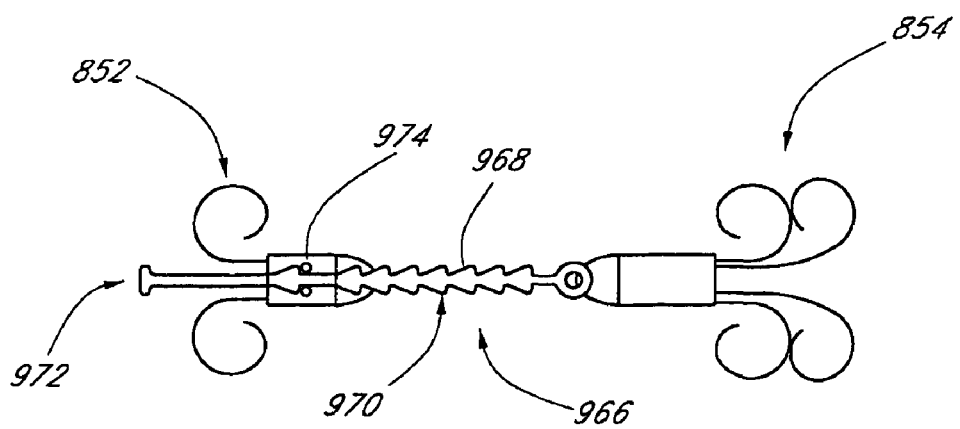
FIGS. 37A-B depict various views of adjustment mechanisms that comprise a zip tie, according to some embodiments of the invention.
Figure 37B:
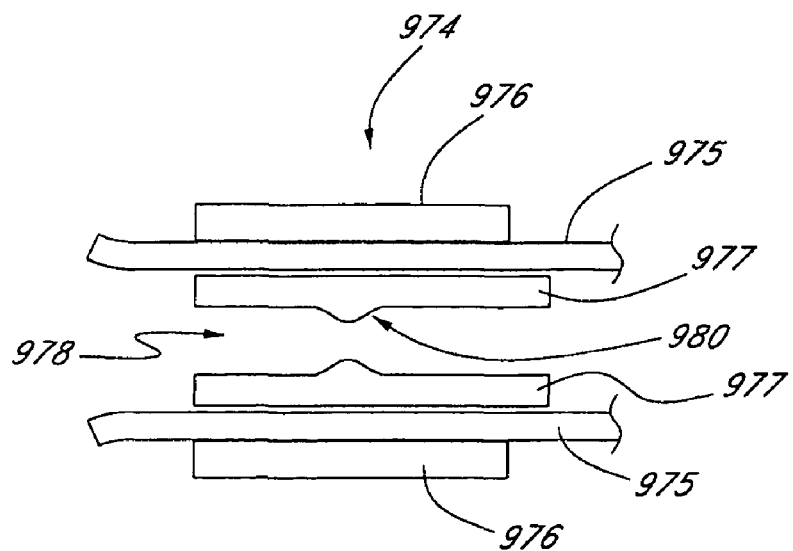

FIG. 37A depicts an embodiment of an adjustment mechanism 966 that comprises a zip tie 968. The zip tie 968 is preferably molded. The zip tie 968 includes one-way or two-way ramps 970 as shown depending on the type of adjustment desired. The zip tie 968 is shown attached to both a proximal anchor 852 and a distal anchor 854. The zip tie 968 also includes an elongated proximal end 972 that may be used for grasping and pulling in order to adjust the tension of the system. The proximal anchor 852 shown includes a ratcheting element 974 (shown within the square box) to facilitate ratcheting of the zip tie 968. FIG. 37B is a detailed view of the ratcheting element 974 shown in FIG. 37A. Shown is an outer sleeve 976 and barbs 975 of the proximal anchor 852. The internal walls of the inner sleeve 977 define a channel 978 configured to receive the zip tie 968 therethrough. The walls contain a plurality of protruding surfaces ("bumps") 980 configured to inhibit sliding of the zip tie 968 when the system is implanted within the tongue. However, the frictional forces of the protruding surfaces 980 may be overcome to adjust the tension between the anchors 852, 854, such as by pulling on the elongated proximal end 972 of the zip tie 968 to facilitate ratcheting.

Figure 38:
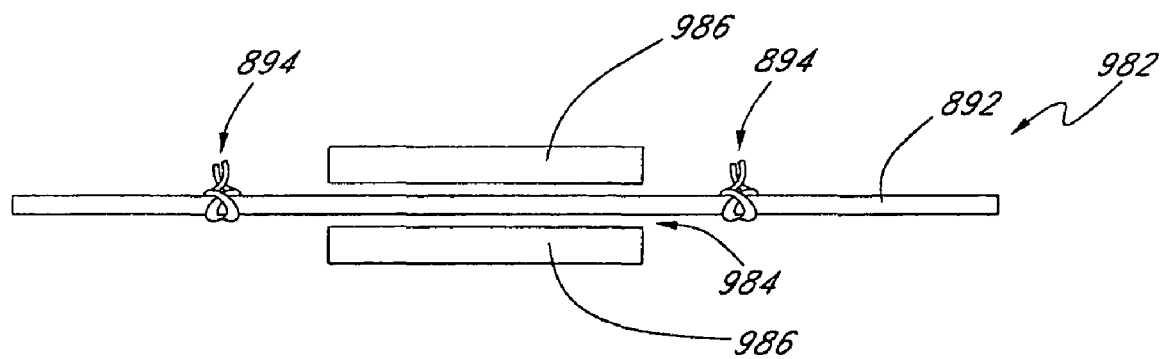
FIG. 38 shows an adjustment mechanism that comprises a beaded tether, according to some embodiments of the invention.

FIG. 38 shows another embodiment of an adjustment mechanism comprising a beaded tether 892. In some embodiments, the beads are a plurality of overhand knots 894 interspersed at a substantially similar distance from one another along the tether 892. An adjustment element 982 shown is a channel 984 defined by two walls 986 of a center of a tissue anchor. In some embodiments, the walls 986 preferably are made of titanium. The inside diameter of the channel 984 is smaller than the outside diameter of the knot 894 or bead. The channel 984 is preferably sized to precisely tune the force required to overcome the knot or bead 894 and provide the ratcheting effect. When the force is applied, the knot 894 deforms sufficiently to pass through the smaller inside diameter of the channel 984 of the tissue anchor center. In one preferred embodiment, the tether 892 is a Dyneema 2-0 thread with an outside diameter of about 0.017 inches and a single overhand knot with an outside diameter of about 0.033 to about 0.035 inches. The channel 984 has an inside diameter of about 0.029 inches. In another preferred embodiment, the tether 892 is a Force Fiber 20 material with a first cross-sectional length of about 0.016 inches and a second cross-sectional length of about 0.010 inches. A double overhand knot 894 has an outside diameter of preferably about 0.034 to 0.036 inches. The channel 984 has an inside diameter of about 0.029 inches. One of ordinary skill in the art will note that a wide range of tethers 892, knots 894, and channel 984 diameter combinations can be utilized.

FIG. 39 shows another embodiment of a part of an adjustment mechanism 986 with a channel 984 in which the tether line may pass therethrough. In some embodiments, the channel 984 may have dimensions as described above in connection with FIG. 38. However, the channel 984 diameter may be readily modified to accommodate a wide range of tethers and knots as noted above.

FIGS. 40A-B show various embodiments of an adjustment mechanism that comprises a beaded tether 892. In these embodiments, in lieu of knots 894 as shown in FIG. 38, the beads 986, 988, 990, 992, 994, 998 are preferably molded balls or beads. As with the various other beaded embodiments described elsewhere in the application, the beads will act as a friction lock between the outside diameter of the bead and the inside diameter of the channel. Shown in FIG. 40A are various bead shapes including sphere 986, bowtie 988, football 990, disc 992, and arrow 994 configurations. However, a multitude of other shapes for use with the present invention can readily be envisioned. In the embodiment shown in FIG. 40B, the tether 996 comprises a metal wire or ribbon. The wire or ribbon preferably comprises a shape memory material, such as Nitinol, or a deformable wire, such as a stainless steel wire. Bead-like protrusions 998 of various configurations may be created by deforming the wire or ribbon 996 with a die, creating flattened areas that interact as a friction lock in a similar manner as beads or knots. The wire 996 may be formed in a zig-zag shape to deform a friction lock. Applying a source of heat or cold may transform the shape memory material. In one embodiment, the protrusion portion may have a horizontal sectional diameter of about 0.020", a narrow portion 1000 may have a horizontal section diameter of about 0.010", and the ribbon may have a vertical sectional diameter of about 0.015".

Figure 41A:
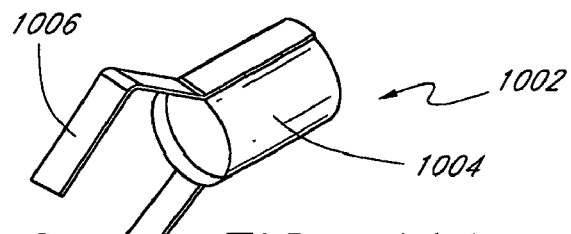
Figure 41B:
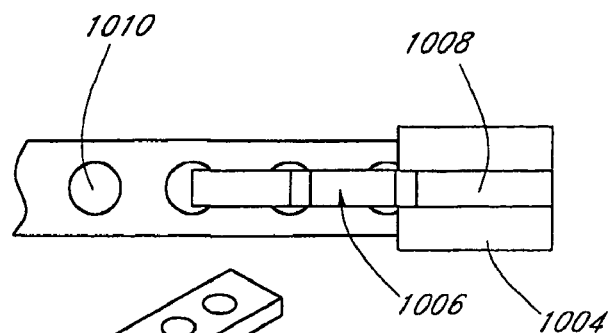
Figure 41C:
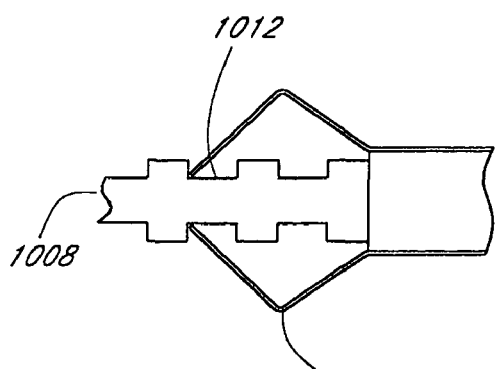

FIGS. 41A-F illustrate another embodiment of an adjustment mechanism 1002 that comprises a sleeve 1004, which may be part of a tissue anchor as described above. As shown in FIG. 41A, the sleeve 1004 is preferably a hypotube made of Nitinol. The Nitinol sleeve 1004 further includes a plurality of attached V-shaped flanges 1006 ("fingers") that may be shaped, for example, by laser cutting. FIG. 41B shows an embodiment where the flanges of the sleeve 1006 (also described herein as a "fingered sleeve") is engaged with a tether 1008, shown here as a zip tie or rectangular bar. The zip tie or rectangular bar 1008 have a plurality of holes 1010. The sleeve 1004 also preferably comprises a friction lock to facilitate ratcheting. The flanges 1006 of the sleeve 1004 may ratchet over the holes 1010 to facilitate adjustment of the tension of tether 1006. FIG. 41C shows another embodiment where the fingered sleeve 1006 is ratcheting over indentations of a corrugated tether 1008. During ratcheting, the fingers 1006 spring outward as shown, but then are configured, such as by elastic recoil properties in the fingers 1006, to move inward and engage with another indentation 1012 of the corrugated tether 1008. FIG. 41D shows a side view of the fingered sleeve 1006 attached to the proximal anchor 852. A closeup view of the area near the finger 1006 ends highlighted by the arrow in FIG. 41D is provided in FIG. 41E. FIG. 41E illustrates an end view of other embodiments where the fingered sleeves 1006 may have a double 1012 or single 1014 notch as shown. Shown below the fingers are tethers 1016 (e.g., zip ties) configured with complementary grooves 1018, 1020 to receive the respective fingers 1006 during ratcheting. FIG. 41F illustrates that an operator may advantageously adjust the device by applying pressure at a point 1022 removed from the finger 1006 ends without penetrating the tissue.

FIGS. 42-48 illustrate embodiments of adjustment mechanisms that may be used with a double-ended anchor that may used for tongue remodeling.

FIG. 42 shows an embodiment of a double-ended anchor 1024 with a first anchor 1026 containing a threaded channel 1028 configured to receive a threaded tether 1030. The threaded tether 1030 is a screw 1030 in the embodiment shown. The length of the double-ended anchor 1024 may be adjusted using an adjustment tool 1032, shown here as a screwdriver, to turn the head of the screw 1030 in an appropriate direction. A second anchor 1034 comprises a pivot 1036 engaged with a complementary structure of a screw 1030 as shown.

FIG. 43 shows an embodiment of an adjustable double-ended anchor with a spool 1040 attached to one of the anchors. The spool 1040 includes a magnetic portion 1042. An adjustment tool 1046 that also comprises a magnet 1044 can be used to facilitate alignment with the magnetic portion 1042 of the spool 1040 as shown. Thus, the magnets 1042, 1044 may advantageously assist an operator in locating the spool 1040 for adjustment post-implantation prior to creating an incision as well as when visualization is limited, for example, in a relatively small surgical field or incision.

Figure 44:
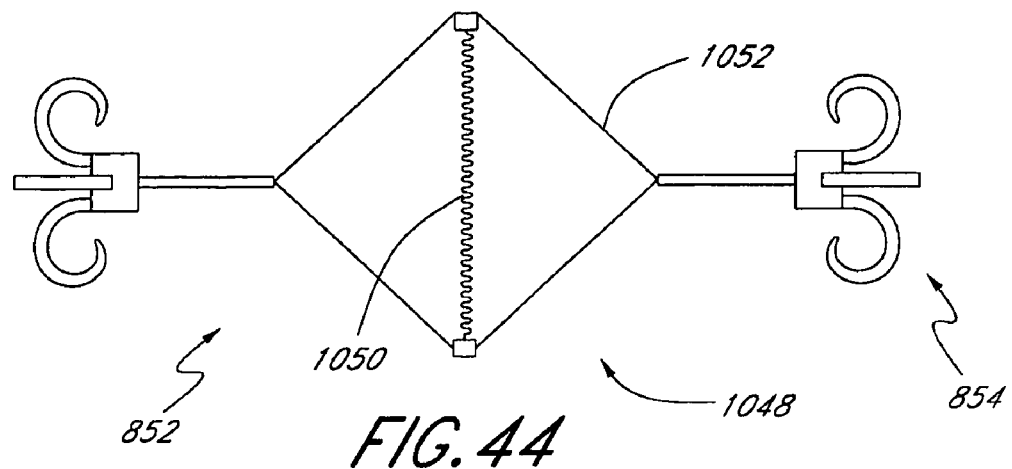
FIG. 44 shows an embodiment of an adjustment mechanism comprising an expansion element.

FIG. 44 shows an embodiment of an adjustment mechanism 1048 that comprises an expansion element 1050. The expansion element 1050 shown is attached to the tether 1052 at a plurality of locations. The expansion element 1050 is configured to increase or decrease in length in a direction substantially perpendicular to the long axis of a tongue remodeling system. Elongation of the expansion element 1050 in a direction as shown will serve to draw the proximal 852 and distal 854 anchors closer together and thus adjust tension on the tether 1052. Some non-limiting examples of expansion elements 1050 include a ratcheting jack or a shape memory material.

Figure 45:
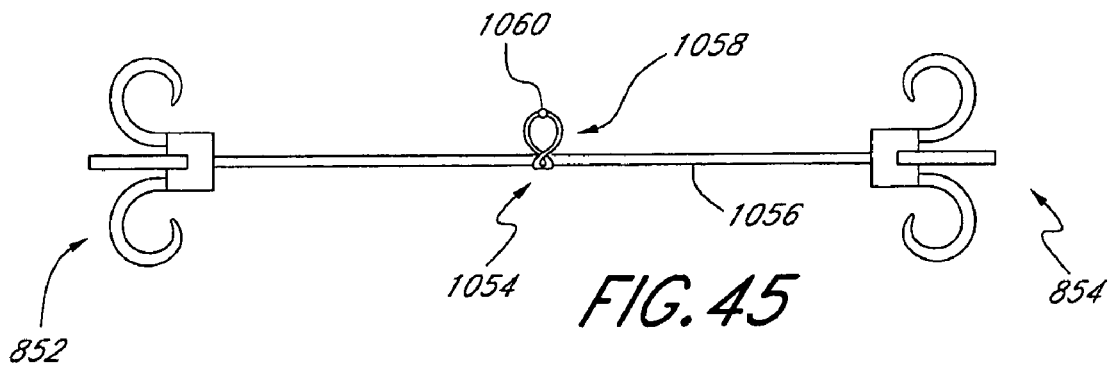
FIG. 45 shows an embodiment of an adjustment mechanism comprising a tether with an adjustable butterfly knot.

FIG. 45 shows an embodiment of an adjustment mechanism 1054 comprising a tether 1056 with an adjustable butterfly knot 1058. The knot 1058 includes a bead 1060 to aid dissection and facilitate the adjustability of the knot 1058. The bead 1060 advantageously assists an operator, who may locate the bead 1060 by palpation if it is not easily visualized within the tissue layer. In other embodiments, the bead 1060 may be any other structure with bulk to facilitate palpation. In still other embodiments, the bead 1060 may be a radioopaque element for visualization under fluoroscopy, or, alternatively, ultrasonically visible.

Figure 46:
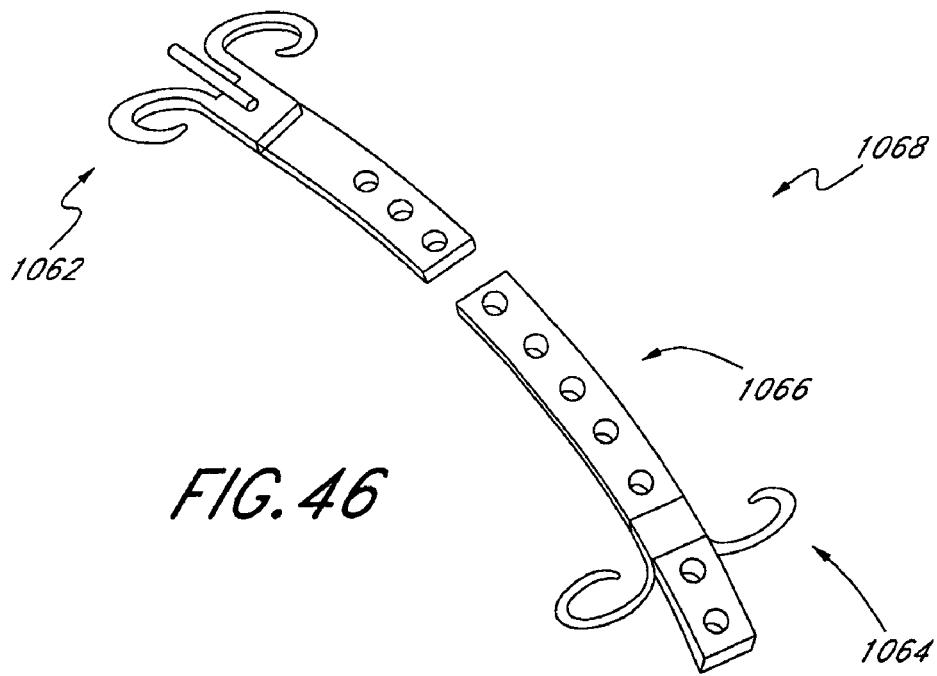
FIG. 46 shows an embodiment of a double-ended anchoring system connected by a tether.

FIG. 46 shows an embodiment of a double-ended anchoring system 1068 connected by a tether 1066 that is preferably a zip tie. The zip tie 1066 preferably has a rectangular cross-section, although square and other cross-sectional shapes are also contemplated. At least one of the anchors 1064 as shown is configured to ratchet down the zip tie 1066 in response to a force. In some embodiments, the anchoring system 1068 can be advantageously adjusted using manual manipulation without any incisions to move the anchors 1062, 1064 closer together using the semi-rigid connector.

Figure 47:
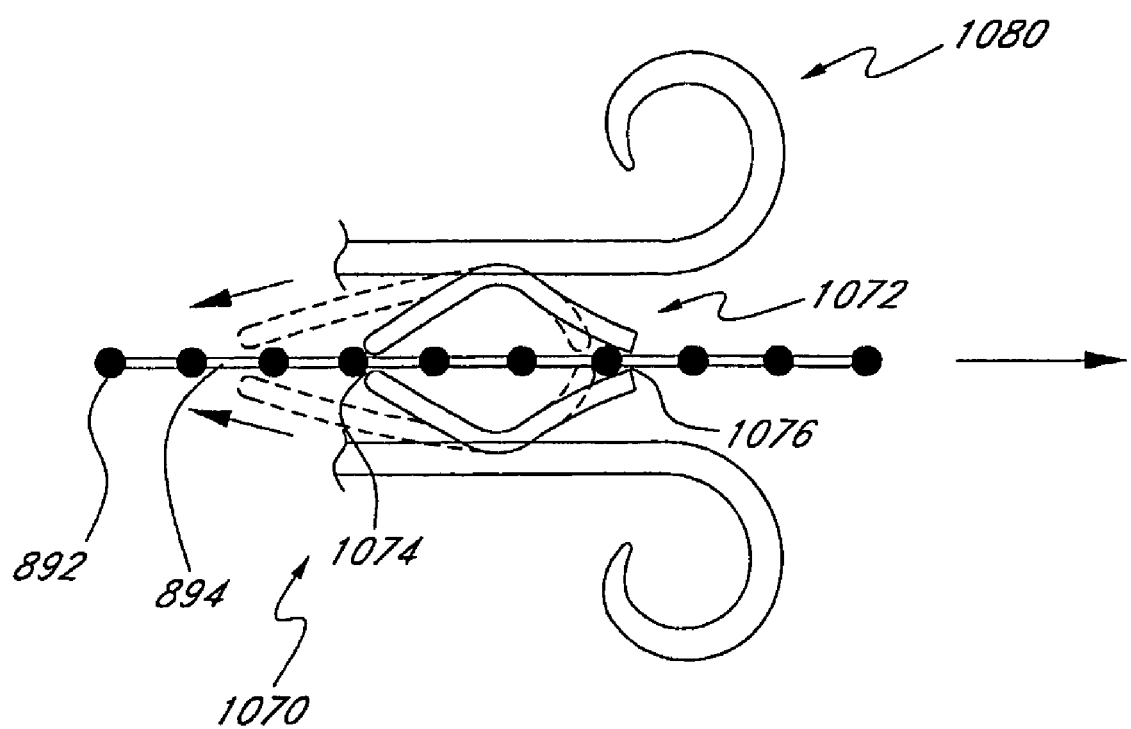
FIG. 47 shows an embodiment of an adjustment mechanism that may be manually adjusted.

FIG. 47 shows an embodiment of an adjustment mechanism 1070 that has a luminal portion 1072 that has a proximal 1074 and distal 1076 narrow apex point and a wider diameter middle portion 1078. A beaded tether 894 is also shown, described in more detail elsewhere in the application. In this embodiment, the adjustment mechanism 1070 is at least partially contained within an anchor 1080 as shown. The narrow apex portions 1074, 1076 have cross-sections that are smaller than that of a bead 892. In order for tension on the beaded tether 894 to be adjusted, the beads 892 need to overcome the small cross-section of the narrow apex portions 1074, 1076 within the adjustment mechanism 1070. This may be accomplished by squeezing the adjustment element 1070 in a first direction (e.g., manually with a thumb and forefinger) while applying countertraction on the beaded tether 894 in a second direction generally opposite to the first direction.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A tongue remodeling system, comprising:
a space creating means for creating a space in a tongue,
a mechanism comprising an expandable tissue anchor configured to collapse the space, wherein the mechanism comprises a soft-tissue anchor and a hard-tissue anchor tethered to the soft-tissue anchor and wherein the expandable tissue anchor comprises a plurality of expandable elements, each element being expandable from a generally linear first position to a curved, hook-shaped, second position.

2. The tongue remodeling system of claim 1, wherein the mechanism comprises a distal tissue-engaging member and a proximal tissue-engaging member.

3. The tongue remodeling system of claim 2, further comprising an adjustment assembly for adjusting at least one of the tension between the distal and proximal tissue-engaging members or the spacing between the distal and proximal tissue-engaging members.

4. The tongue remodeling system of claim 1, wherein the mechanism comprises an adjustment assembly.

5. The tongue remodeling system of claim 4, wherein the adjustment assembly is configured for attachment to a bony structure.

6. A mechanism for collapsing a space in a tongue, the mechanism comprising:
an expandable soft-tissue anchor comprising a plurality of outwardly expandable elements wherein the outwardly expandable elements comprise hook elements;
a hard-tissue anchor; and
a coupling member having a first end and an opposite second end, the first end being coupled to the soft-tissue anchor and the opposite second end being coupled to the hard-tissue anchor.

7. The mechanism of claim 6, wherein the coupling member comprises an adjustment assembly.

8. A mechanism for closing a space in a tongue, the mechanism comprising:
an expandable distal tissue-engaging member wherein the expandable distal tissue-engaging member comprises a plurality of expandable elements, each element being expandable from a generally linear first position to a curved, hook-shaped, second position; and
a proximal tissue-engaging member coupled to the distal tissue-engaging member via a coupling member,
wherein the coupling member comprises an adjustment assembly for adjusting at least one of the tension between the distal and proximal tissue-engaging members or the spacing between the distal and proximal tissue-engaging members.

9. The mechanism of claim 8, wherein the adjustment assembly is configured for attachment to a bony structure.

10. The mechanism of claim 8, wherein the adjustment assembly is adapted to selectively vary the spacing between the expandable soft-tissue anchor and the hard-tissue anchor.

* * * * *